(12) United States Patent
Kimura

(10) Patent No.: US 8,192,740 B2
(45) Date of Patent: Jun. 5, 2012

(54) PHARMACEUTICAL COMPOSITION COMPRISING ANTI-GRP78 ANTIBODY AS ACTIVE INGREDIENT

(75) Inventor: Naoki Kimura, Tokyo (JP)

(73) Assignee: Forerunner Pharma Research Co., Ltd., Tokyo (JP)

( * ) Notice: Subject to any disclaimer, the term of this patent is extended or adjusted under 35 U.S.C. 154(b) by 0 days.

(21) Appl. No.: 12/449,778

(22) PCT Filed: Feb. 27, 2008

(86) PCT No.: PCT/JP2008/053898
§ 371 (c)(1),
(2), (4) Date: Aug. 26, 2009

(87) PCT Pub. No.: WO2008/105560
PCT Pub. Date: Sep. 4, 2008

(65) Prior Publication Data
US 2010/0041074 A1 Feb. 18, 2010

(30) Foreign Application Priority Data
Feb. 27, 2007 (JP) ................. 2007-047534

(51) Int. Cl.
*A61K 39/395* (2006.01)
*A61K 39/00* (2006.01)
*C07K 16/00* (2006.01)
*C07K 17/00* (2006.01)
*C07K 17/14* (2006.01)
*C12P 21/08* (2006.01)
*G01N 33/53* (2006.01)

(52) U.S. Cl. ............. 424/141.1; 424/130.1; 424/138.1; 424/155.5; 424/178.1; 530/387.1; 530/388.1; 530/388.8; 530/391.1; 435/7.1

(58) Field of Classification Search ............. None
See application file for complete search history.

(56) References Cited

U.S. PATENT DOCUMENTS

| | | | |
|---|---|---|---|
| 7,420,030 B2 | 9/2008 | Arap et al. | |
| 7,452,964 B2 | 11/2008 | Pasqualini et al. | |
| 7,671,010 B2 | 3/2010 | Arap et al. | |
| 2005/0143291 A1* | 6/2005 | Lee | 514/8 |

FOREIGN PATENT DOCUMENTS

| | | |
|---|---|---|
| JP | 2004-515751 A | 5/2004 |
| WO | WO 01/19858 A2 | 3/2001 |
| WO | WO 02/20722 A2 | 3/2002 |
| WO | WO 2004/020999 A1 | 3/2004 |
| WO | WO 2005/085862 A1 | 9/2005 |
| WO | WO 2006/039173 A2 | 4/2006 |

OTHER PUBLICATIONS

Gonzalez-Gronow, Cuchacovich, Llanos, Urzua, Gawdi, and Pizzo. Prostate cancer cell proliferation in vitro is modulated by antibodies against glucose-regulated protein 78 isolated from patient serum. Cancer Research, 2006. vol. 66, pp. 11424-11431.*
Paul, Fundamental Immunology, 3rd Edition, 1993, pp. 292-295, under the heading "Fv Structure and Diversity in Three Dimensions".*
Rudikoff, Giusti, Cook, and Scharff. Single amino acid substitution altering antigen-binding specificity. Proceedings of the National Academy of Sciences, 1982. vol. 79, pp. 1979-1983.*
Colman. Effects of amino acid sequence changes on antibody-antigen interactions. Research in Immunology, 1994. vol. 145, pp. 33-36.*
Mac Callum, Martin, and Thornton. Antibody-antigen interactions: contact analysis and binding site topography. Journal of Molecular Biology, 1996. vol. 262, pp. 732-745.*
Campbell. Monoclonal Antibody Technology, 1984. pp. 1-32.*
Database Biosis on STN, 2005, Acc. No. 2005:529385 abstract (Pizzo et al., "Attenuation of mitogenesis and cellular proliferation in 1-LN prostate cancer cells treated with antibodies against GRP78, a surface binding protein of $\alpha$-2," FASEB Journal, Mar. 4, 2005, 19(4Supp2,Part1):A253).
Chatterjee et al., "Induction of M9r) 78,000 glucose-regulated stress protein in poly(adenosine diphosphate-ribose)polymerase- and nicotinamide adenine dinucleotide-deficient V79 cell lines and its relation to resistance to the topoisomerase II inhibitor etoposide," Cancer Research, 1994, 54(16):4405-4411.
Berger et al., "A lymphocyte cell surface heat shock protein homologous to the endoplasmic reticulum chaperone, immunoglobulin heavy chain binding protein BIP," Int. J. Cancer, 1997, 71:1077-1085.
Supplementary European Search Report dated Jan. 28, 2011, in corresponding EP 08721318.7, 8 pages.
Delpino et al., "The 78 kDa Glucose-regulated Protein (GRP78/BIP) is Expressed on the Cell Membrane, is Released into Cell Culture Medium and is Also Present in Human Peripheral Circulation," Bioscience Reports, Jun. and Aug. 2002, 22(3 and 4):47-420.
Kozutsumi et al., "Identification of immunoglobulin heavy chain binding protein as glucose-regulated protein 78 on the basis of amino acid sequence, immunological cross-reactivity, and functional activity," J. Cell Sci., Supplement, 1989, 11:115-137.
Delpino et al., "The 78 kDa Glucose-regulated Protein (GRP78/BIP) is Expressed on the Cell Membrane, is Released into Cell Culture Medium and is Also Present in Human Peripheral Circulation," Bioscience Reports, Jun. and Aug. 2002, 22(3 and 4):407-420.

\* cited by examiner

*Primary Examiner* — Anne M. Gussow
(74) *Attorney, Agent, or Firm* — Foley & Lardner LLP

(57) ABSTRACT

An object of the present invention is to provide novel pharmaceutical compositions using anti-GRP78 antibodies. More particularly, the present invention provides a novel method of cancer treatment using anti-GRP78 antibodies, novel cell growth inhibitors and anticancer agents that contain anti-GRP78 antibodies, as well as novel anti-GRP78 antibodies. The present inventor prepared antitumor antibodies to target GRP78, the localization of which in cancer cells changed to the cell membrane. The inventor successfully obtained an anti-GRP78 antibody that would bind specifically to the cell surface of cancer cells, leading to the accomplishment of the above-mentioned objects.

20 Claims, 16 Drawing Sheets

(A)

(B)

Blot: GA-20

(A)

(B)

(A)

(B)

SEQUENCE LISTING

```
<160> NUMBER OF SEQ ID NOS: 102

<210> SEQ ID NO 1
<211> LENGTH: 1965
<212> TYPE: DNA
<213> ORGANISM: Homo sapiens
<220> FEATURE:
<221> NAME/KEY: CDS
<222> LOCATION: (1)..(1965)

<400> SEQUENCE: 1 atg aag ctc tcc ctg gtg gcc gcg atg ctg ctg ctc agc gcg gcg        48
Met Lys Leu Ser Leu Val Ala Ala Met Leu Leu Leu Leu Ser Ala Ala
1               5                   10                  15 cgg gcc gag gag gag gac aag aag gag gac gtg ggc acg gtg gtc ggc    96
Arg Ala Glu Glu Glu Asp Lys Lys Glu Asp Val Gly Thr Val Val Gly
                20                  25                  30 atc gac ctg ggg acc acc tac tcc tgc gtc ggc gtg ttc aag aac ggc    144
Ile Asp Leu Gly Thr Thr Tyr Ser Cys Val Gly Val Phe Lys Asn Gly
            35                  40                  45 cgc gtg gag atc atc gcc aac gat cag ggc aac cgc atc acg ccg tcc    192
Arg Val Glu Ile Ile Ala Asn Asp Gln Gly Asn Arg Ile Thr Pro Ser
        50                  55                  60 tat gtc gcc ttc act cct gaa ggg gaa cgt ctg att ggc gat gcc gcc    240
Tyr Val Ala Phe Thr Pro Glu Gly Glu Arg Leu Ile Gly Asp Ala Ala
65                  70                  75                  80 aag aac cag ctc acc tcc aac ccc gag aac acg gtc ttt gac gcc aag    288
Lys Asn Gln Leu Thr Ser Asn Pro Glu Asn Thr Val Phe Asp Ala Lys
                85                  90                  95 cgg ctc atc ggc cgc acg tgg aat gac ccg tct gtg cag cag gac atc    336
Arg Leu Ile Gly Arg Thr Trp Asn Asp Pro Ser Val Gln Gln Asp Ile
                100                 105                 110 aag ttc ttg ccg ttc aag gtg gtt gaa aag aaa act aaa cca tac att    384
Lys Phe Leu Pro Phe Lys Val Val Glu Lys Lys Thr Lys Pro Tyr Ile
            115                 120                 125 caa gtt gat att gga ggt ggg caa aca aag aca ttt gct cct gaa gaa    432
Gln Val Asp Ile Gly Gly Gly Gln Thr Lys Thr Phe Ala Pro Glu Glu
        130                 135                 140 att tct gcc atg gtt ctc act aaa atg aaa gaa acc gct gag gct tat    480
Ile Ser Ala Met Val Leu Thr Lys Met Lys Glu Thr Ala Glu Ala Tyr
145                 150                 155                 160 ttg gga aag aag gtt acc cat gca gtt gtt act gta cca gcc tat ttt    528
Leu Gly Lys Lys Val Thr His Ala Val Val Thr Val Pro Ala Tyr Phe
                165                 170                 175 aat gat gcc caa cgc caa gca acc aaa gac gct gga act att gct ggc    576
Asn Asp Ala Gln Arg Gln Ala Thr Lys Asp Ala Gly Thr Ile Ala Gly
                180                 185                 190
```

```
cta aat gtt atg agg atc atc aac gag cct acg gca gct gct att gct       624
Leu Asn Val Met Arg Ile Ile Asn Glu Pro Thr Ala Ala Ala Ile Ala
        195                 200                 205 tat ggc ctg gat aag agg gag ggg gag aag aac atc ctg gtg ttt gac       672
Tyr Gly Leu Asp Lys Arg Glu Gly Glu Lys Asn Ile Leu Val Phe Asp
210                 215                 220 ctg ggt ggc gga acc ttc gat gtg tct ctt ctc acc att gac aat ggt       720
Leu Gly Gly Gly Thr Phe Asp Val Ser Leu Leu Thr Ile Asp Asn Gly
225                 230                 235                 240 gtc ttc gaa gtt gtg gcc act aat gga gat act cat ctg ggt gga gaa       768
Val Phe Glu Val Val Ala Thr Asn Gly Asp Thr His Leu Gly Gly Glu
                245                 250                 255 gac ttt gac cag cgt gtc atg gaa cac ttc atc aaa ctg tac aaa aag       816
Asp Phe Asp Gln Arg Val Met Glu His Phe Ile Lys Leu Tyr Lys Lys
            260                 265                 270 aag acg ggc aaa gat gtc agg aaa gac aat aga gct gtg cag aaa ctc       864
Lys Thr Gly Lys Asp Val Arg Lys Asp Asn Arg Ala Val Gln Lys Leu
        275                 280                 285 cgg cgc gag gta gaa aag gcc aaa cgg gcc ctg tct tct cag cat caa       912
Arg Arg Glu Val Glu Lys Ala Lys Arg Ala Leu Ser Ser Gln His Gln
290                 295                 300 gca aga att gaa att gag tcc ttc tat gaa gga gaa gac ttt tct gag       960
Ala Arg Ile Glu Ile Glu Ser Phe Tyr Glu Gly Glu Asp Phe Ser Glu
305                 310                 315                 320 acc ctg act cgg gcc aaa ttt gaa gag ctc aac atg gat ctg ttc cgg      1008
Thr Leu Thr Arg Ala Lys Phe Glu Glu Leu Asn Met Asp Leu Phe Arg
                325                 330                 335 tct act atg aag ccc gtc cag aaa gtg ttg gaa gat tct gat ttg aag      1056
Ser Thr Met Lys Pro Val Gln Lys Val Leu Glu Asp Ser Asp Leu Lys
            340                 345                 350 aag tct gat att gat gaa att gtt ctt gtt ggt ggc tcg act cga att      1104
Lys Ser Asp Ile Asp Glu Ile Val Leu Val Gly Gly Ser Thr Arg Ile
        355                 360                 365 cca aag att cag caa ctg gtt aaa gag ttc ttc aat ggc aag gaa cca      1152
Pro Lys Ile Gln Gln Leu Val Lys Glu Phe Phe Asn Gly Lys Glu Pro
370                 375                 380 tcc cgt ggc ata aac cca gat gaa gct gta gcg tat ggt gct gct gtc      1200
Ser Arg Gly Ile Asn Pro Asp Glu Ala Val Ala Tyr Gly Ala Ala Val
385                 390                 395                 400 cag gct ggt gtg ctc tct ggt gat caa gat aca ggt gac ctg gta ctg      1248
Gln Ala Gly Val Leu Ser Gly Asp Gln Asp Thr Gly Asp Leu Val Leu
                405                 410                 415 ctt gat gta tgt ccc ctt aca ctt ggt att gaa act gtg gga ggt gtc      1296
Leu Asp Val Cys Pro Leu Thr Leu Gly Ile Glu Thr Val Gly Gly Val
            420                 425                 430 atg acc aaa ctg att cca agg aac aca gtg gtg cct acc aag aag tct      1344
Met Thr Lys Leu Ile Pro Arg Asn Thr Val Val Pro Thr Lys Lys Ser
        435                 440                 445 cag atc ttt tct aca gct tct gat aat caa cca act gtt aca atc aag      1392
Gln Ile Phe Ser Thr Ala Ser Asp Asn Gln Pro Thr Val Thr Ile Lys
450                 455                 460 gtc tat gaa ggt gaa aga ccc ctg aca aaa gac aat cat ctt ctg ggt      1440
Val Tyr Glu Gly Glu Arg Pro Leu Thr Lys Asp Asn His Leu Leu Gly
465                 470                 475                 480 aca ttt gat ctg act gga att cct cct gct cct cgt ggg gtc cca cag      1488
Thr Phe Asp Leu Thr Gly Ile Pro Pro Ala Pro Arg Gly Val Pro Gln
                485                 490                 495 att gaa gtc acc ttt gag ata gat gtg aat ggt att ctt cga gtg aca      1536
Ile Glu Val Thr Phe Glu Ile Asp Val Asn Gly Ile Leu Arg Val Thr
            500                 505                 510
```

```
gct gaa gac aag ggt aca ggg aac aaa aat aag atc aca atc acc aat       1584
Ala Glu Asp Lys Gly Thr Gly Asn Lys Asn Lys Ile Thr Ile Thr Asn
            515                 520                 525 gac cag aat cgc ctg aca cct gaa gaa atc gaa agg atg gtt aat gat       1632
Asp Gln Asn Arg Leu Thr Pro Glu Glu Ile Glu Arg Met Val Asn Asp
        530                 535                 540 gct gag aag ttt gct gag gaa gac aaa aag ctc aag gag cgc att gat       1680
Ala Glu Lys Phe Ala Glu Glu Asp Lys Lys Leu Lys Glu Arg Ile Asp
545                 550                 555                 560 act aga aat gag ttg gaa agc tat gcc tat tct cta aag aat cag att       1728
Thr Arg Asn Glu Leu Glu Ser Tyr Ala Tyr Ser Leu Lys Asn Gln Ile
                565                 570                 575 gga gat aaa gaa aag ctg gga ggt aaa ctt tcc tct gaa gat aag gag       1776
Gly Asp Lys Glu Lys Leu Gly Gly Lys Leu Ser Ser Glu Asp Lys Glu
            580                 585                 590 acc atg gaa aaa gct gta gaa gaa aag att gaa tgg ctg gaa agc cac       1824
Thr Met Glu Lys Ala Val Glu Glu Lys Ile Glu Trp Leu Glu Ser His
        595                 600                 605 caa gat gct gac att gaa gac ttc aaa gct aag aag aag gaa ctg gaa       1872
Gln Asp Ala Asp Ile Glu Asp Phe Lys Ala Lys Lys Lys Glu Leu Glu
610                 615                 620 gaa att gtt caa cca att atc agc aaa ctc tat gga agt gca ggc cct       1920
Glu Ile Val Gln Pro Ile Ile Ser Lys Leu Tyr Gly Ser Ala Gly Pro
625                 630                 635                 640 ccc cca act ggt gaa gag gat aca gca gaa aaa gat gag ttg tag           1965
Pro Pro Thr Gly Glu Glu Asp Thr Ala Glu Lys Asp Glu Leu
                645                 650

<210> SEQ ID NO 2
<211> LENGTH: 654
<212> TYPE: PRT
<213> ORGANISM: Homo sapiens

<400> SEQUENCE: 2

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190
```

```
Leu Asn Val Met Arg Ile Ile Asn Glu Pro Thr Ala Ala Ala Ile Ala
            195                 200                 205

Tyr Gly Leu Asp Lys Arg Gly Glu Lys Asn Ile Leu Val Phe Asp
            210                 215                 220

Leu Gly Gly Gly Thr Phe Asp Val Ser Leu Leu Thr Ile Asp Asn Gly
225                 230                 235                 240

Val Phe Glu Val Ala Thr Asn Gly Asp Thr His Leu Gly Gly Glu
            245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
            290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
            325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
            370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
            450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
            530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
```

```
            610                 615                 620
Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 3
<211> LENGTH: 40
<212> TYPE: PRT
<213> ORGANISM: Homo sapiens

<400> SEQUENCE: 3

Lys Glu Phe Phe Asn Gly Lys Glu Pro Ser Arg Gly Ile Asn Pro Asp
1               5                   10                  15

Glu Ala Val Ala Tyr Gly Ala Ala Val Gln Ala Gly Val Leu Ser Gly
            20                  25                  30

Asp Gln Asp Thr Gly Asp Leu Val
        35                  40

<210> SEQ ID NO 4
<211> LENGTH: 360
<212> TYPE: DNA
<213> ORGANISM: Mus musculus

<400> SEQUENCE: 4
gaggtccagc tgcaacagtc tggacctgag ctggtgaagc ctggggcttc agtgaagata      60
tcctgcaaga cttctggata cacattcact gaatacacca tgcactgggt gaagcagagc     120
catggaaaga gccttgagtg gattggaggt attaatccta acaatggtgg tactagctac     180
aaccagaagt tcaagggcaa ggccacattg actgtagaca gtcctccag cacagcctac      240 atggagctcc gcagcctgac atctgaggat tctgcagtct attactgtgc aagagaaaag     300
tatggtaact actatgctat ggactactgg ggtcaaggaa cctcagtcac cgtctcctca     360

<210> SEQ ID NO 5
<211> LENGTH: 120
<212> TYPE: PRT
<213> ORGANISM: Mus musculus

<400> SEQUENCE: 5

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Lys Tyr Gly Asn Tyr Tyr Ala Met Asp Tyr Trp Gly Gln
            100                 105                 110

Gly Thr Ser Val Thr Val Ser Ser
        115                 120

<210> SEQ ID NO 6
<211> LENGTH: 336
```

```
<212> TYPE: DNA
<213> ORGANISM: Mus musculus

<400> SEQUENCE: 6
gacattgtga tgtcacagtc tccatcctcc ctggctgtgt cagcaggaga gaaggtcact      60
atgagctgca aatccagtca gagtctgctc aacagtagaa cccgaaagaa ctacttggct     120
tggtaccagc agaaaccagg gcagtctcct aaactgctga tctactgggc atccactagg     180
gaatctgggg tccctgatcg cttcacaggc agtggatctg gacagattt  cactctcacc     240 atcagcagtg tgcaggctga agacctggca gtttattact gcaagcaatc ttataatctt     300
cggacgttcg gtggaggcac caagctggaa atcaaa                               336

<210> SEQ ID NO 7
<211> LENGTH: 112
<212> TYPE: PRT
<213> ORGANISM: Mus musculus

<400> SEQUENCE: 7

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 8
<211> LENGTH: 5
<212> TYPE: PRT
<213> ORGANISM: Mus musculus

<400> SEQUENCE: 8

Glu Tyr Thr Met His
1               5

<210> SEQ ID NO 9
<211> LENGTH: 17
<212> TYPE: PRT
<213> ORGANISM: Mus musculus

<400> SEQUENCE: 9

Gly Ile Asn Pro Asn Asn Gly Gly Thr Ser Tyr Asn Gln Lys Phe Lys
1               5                   10                  15

Gly

<210> SEQ ID NO 10
<211> LENGTH: 11
<212> TYPE: PRT
<213> ORGANISM: Mus musculus

<400> SEQUENCE: 10

Glu Lys Tyr Gly Asn Tyr Tyr Ala Met Asp Tyr
1               5                   10
```

```
<210> SEQ ID NO 11
<211> LENGTH: 17
<212> TYPE: PRT
<213> ORGANISM: Mus musculus

<400> SEQUENCE: 11

Lys Ser Ser Gln Ser Leu Leu Asn Ser Arg Thr Arg Lys Asn Tyr Leu
1               5                   10                  15

Ala

<210> SEQ ID NO 12
<211> LENGTH: 7
<212> TYPE: PRT
<213> ORGANISM: Mus musculus

<400> SEQUENCE: 12

Trp Ala Ser Thr Arg Glu Ser
1               5

<210> SEQ ID NO 13
<211> LENGTH: 8
<212> TYPE: PRT
<213> ORGANISM: Mus musculus

<400> SEQUENCE: 13

Lys Gln Ser Tyr Asn Leu Arg Thr
1               5

<210> SEQ ID NO 14
<211> LENGTH: 336
<212> TYPE: DNA
<213> ORGANISM: Mus musculus

<400> SEQUENCE: 14
caggtgcagc tgaagcagtc aggacctggc ctagtgcagc cctcacagag cctgtccatc      60
acctgcacag tctctggttt ctcattaact agctatggtg tacactgggt tcgccagtct     120
ccaggaaagg gtctggagtg gctgggagtg atatggagtg gtggaagcac agactataat     180
gaagctttca tatccagatt gagcatcagc aaggacaatt ccaagagcca gttttctttt     240
aaaatgaaca gtctgcaagc taatgacaca gccatatatt actgtgccag aaattgggac     300
tactggggcc aaggcaccac tctcacagtc tcctca                               336

<210> SEQ ID NO 15
<211> LENGTH: 112
<212> TYPE: PRT
<213> ORGANISM: Mus musculus

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Glu Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
```

85                  90                  95
Arg Asn Trp Asp Tyr Trp Gly Gln Gly Thr Thr Leu Thr Val Ser Ser
            100                 105                 110

<210> SEQ ID NO 16
<211> LENGTH: 336
<212> TYPE: DNA
<213> ORGANISM: Mus musculus

<400> SEQUENCE: 16
gacattgtga tgtcacagtc tccatcctcc ctggctgtgt cagcaggaga gaaggtcact      60
atgagctgca atccagtca gagtctgctc aacagtagaa cccgaaagaa ctacttggct     120
tggtaccagc agaaaccagg gcagtctcct aaactgctga tctactgggc atccactagg     180
gaatctgggg tccctgatcg cttcacaggc agtggatctg ggacagattt cactctcacc     240
atcagcagtg tgcaggctga agacctggca gtttattact gcaagcaatc ttataatctt     300
cggacgttcg gtggaggcac caagctggaa atcaaa                              336

<210> SEQ ID NO 17
<211> LENGTH: 112
<212> TYPE: PRT
<213> ORGANISM: Mus musculus

<400> SEQUENCE: 17

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 18
<211> LENGTH: 5
<212> TYPE: PRT
<213> ORGANISM: Mus musculus

<400> SEQUENCE: 18

Ser Tyr Gly Val His
1               5

<210> SEQ ID NO 19
<211> LENGTH: 16
<212> TYPE: PRT
<213> ORGANISM: Mus musculus

<400> SEQUENCE: 19

Val Ile Trp Ser Gly Gly Ser Thr Asp Tyr Asn Glu Ala Phe Ile Ser
1               5                   10                  15

<210> SEQ ID NO 20
<211> LENGTH: 4
<212> TYPE: PRT

<213> ORGANISM: Mus musculus

<400> SEQUENCE: 20

Asn Trp Asp Tyr
1

<210> SEQ ID NO 21
<211> LENGTH: 17
<212> TYPE: PRT
<213> ORGANISM: Mus musculus

<400> SEQUENCE: 21

Lys Ser Ser Gln Ser Leu Leu Asn Ser Arg Thr Arg Lys Asn Tyr Leu
1               5                   10                  15

Ala

<210> SEQ ID NO 22
<211> LENGTH: 7
<212> TYPE: PRT
<213> ORGANISM: Mus musculus

<400> SEQUENCE: 22

Trp Ala Ser Thr Arg Glu Ser
1               5

<210> SEQ ID NO 23
<211> LENGTH: 8
<212> TYPE: PRT
<213> ORGANISM: Mus musculus

<400> SEQUENCE: 23

Lys Gln Ser Tyr Asn Leu Arg Thr
1               5

<210> SEQ ID NO 24
<211> LENGTH: 2022
<212> TYPE: DNA
<213> ORGANISM: Mus musculus
<220> FEATURE:
<221> NAME/KEY: CDS
<222> LOCATION: (1)..(2022)

<400> SEQUENCE: 24

```
atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
1               5                   10                  15 gcc cag ccg gcg atg gcc atg gat cac cat cac cat cac cat cac cat      96
Ala Gln Pro Ala Met Ala Met Asp His His His His His His His His
                20                  25                  30 cat cac aag ctt gag gtc cag ctg caa cag tct gga cct gag ctg gtg     144
His His Lys Leu Glu Val Gln Leu Gln Gln Ser Gly Pro Glu Leu Val
            35                  40                  45 aag cct ggg gct tca gtg aag ata tcc tgc aag act tct gga tac aca     192
Lys Pro Gly Ala Ser Val Lys Ile Ser Cys Lys Thr Ser Gly Tyr Thr
        50                  55                  60 ttc act gaa tac acc atg cac tgg gtg aag cag agc cat gga aag agc     240
Phe Thr Glu Tyr Thr Met His Trp Val Lys Gln Ser His Gly Lys Ser
65                  70                  75                  80 ctt gag tgg att gga ggt att aat cct aac aat ggt ggt act agc tac     288
Leu Glu Trp Ile Gly Gly Ile Asn Pro Asn Asn Gly Gly Thr Ser Tyr
                85                  90                  95 aac cag aag ttc aag ggc aag gcc aca ttg act gta gac aag tcc tcc     336
Asn Gln Lys Phe Lys Gly Lys Ala Thr Leu Thr Val Asp Lys Ser Ser
                100                 105                 110
```

```
agc aca gcc tac atg gag ctc cgc agc ctg aca tct gag gat tct gca      384
Ser Thr Ala Tyr Met Glu Leu Arg Ser Leu Thr Ser Glu Asp Ser Ala
        115                 120                 125 gtc tat tac tgt gca aga gaa aag tat ggt aac tac tat gct atg gac      432
Val Tyr Tyr Cys Ala Arg Glu Lys Tyr Gly Asn Tyr Tyr Ala Met Asp
130                 135                 140 tac tgg ggt caa gga acc tca gtc acc gtc tcc tca ggt ggt ggt ggt      480
Tyr Trp Gly Gln Gly Thr Ser Val Thr Val Ser Ser Gly Gly Gly Gly
145                 150                 155                 160 tcg ggt ggt ggt ggt tcg ggt ggt ggc gga tcg gac att gtg atg tca      528
Ser Gly Gly Gly Gly Ser Gly Gly Gly Gly Ser Asp Ile Val Met Ser
                165                 170                 175 cag tct cca tcc tcc ctg gct gtg tca gca gga gag aag gtc act atg      576
Gln Ser Pro Ser Ser Leu Ala Val Ser Ala Gly Glu Lys Val Thr Met
                180                 185                 190 agc tgc aaa tcc agt cag agt ctg ctc aac agt aga acc cga aag aac      624
Ser Cys Lys Ser Ser Gln Ser Leu Leu Asn Ser Arg Thr Arg Lys Asn
            195                 200                 205 tac ttg gct tgg tac cag cag aaa cca ggg cag tct cct aaa ctg ctg      672
Tyr Leu Ala Trp Tyr Gln Gln Lys Pro Gly Gln Ser Pro Lys Leu Leu
        210                 215                 220 atc tac tgg gca tcc act agg gaa tct ggg gtc cct gat cgc ttc aca      720
Ile Tyr Trp Ala Ser Thr Arg Glu Ser Gly Val Pro Asp Arg Phe Thr
225                 230                 235                 240 ggc agt gga tct ggg aca gat ttc act ctc acc atc agc agt gtg cag      768
Gly Ser Gly Ser Gly Thr Asp Phe Thr Leu Thr Ile Ser Ser Val Gln
                245                 250                 255 gct gaa gac ctg gca gtt tat tac tgc aag caa tct tat aat ctt cgg      816
Ala Glu Asp Leu Ala Val Tyr Tyr Cys Lys Gln Ser Tyr Asn Leu Arg
                260                 265                 270 acg ttc ggt gga ggc acc aag ctg gaa atc aaa gaa ttc ggt ggc gcg      864
Thr Phe Gly Gly Gly Thr Lys Leu Glu Ile Lys Glu Phe Gly Gly Ala
            275                 280                 285 ccg gag ttc ccg aaa ccg tcc acc ccg cgg tct tct ggt tta gag          912
Pro Glu Phe Pro Lys Pro Ser Thr Pro Pro Gly Ser Ser Gly Leu Glu
        290                 295                 300 ggc ggc agc ctg gcc gcg ctg acc gcg cac cag gct tgc cac ctg ccg      960
Gly Gly Ser Leu Ala Ala Leu Thr Ala His Gln Ala Cys His Leu Pro
305                 310                 315                 320 ctg gag act ttc acc cgt cat cgc cag ccg cgc ggc tgg gaa caa ctg     1008
Leu Glu Thr Phe Thr Arg His Arg Gln Pro Arg Gly Trp Glu Gln Leu
                325                 330                 335 gag cag tgc ggc tat ccg gtg cag cgg ctg gtc gcc ctc tac ctg gcg     1056
Glu Gln Cys Gly Tyr Pro Val Gln Arg Leu Val Ala Leu Tyr Leu Ala
                340                 345                 350 gcg cgg ctg tcg tgg aac cag gtc gac cag gtg atc cgc aac gcc ctg     1104
Ala Arg Leu Ser Trp Asn Gln Val Asp Gln Val Ile Arg Asn Ala Leu
            355                 360                 365 gcc agc ccc ggc agc ggc ggc gac ctg ggc gaa gcg atc cgc gag cag     1152
Ala Ser Pro Gly Ser Gly Gly Asp Leu Gly Glu Ala Ile Arg Glu Gln
        370                 375                 380 ccg gag cag gcc cgt ctg gcc ctg acc ctg gcc gcc gcc gag agc gag     1200
Pro Glu Gln Ala Arg Leu Ala Leu Thr Leu Ala Ala Ala Glu Ser Glu
385                 390                 395                 400 cgc ttc gtc cgg cag ggc acc ggc aac gac gag gcc ggc gcg gcc aac     1248
Arg Phe Val Arg Gln Gly Thr Gly Asn Asp Glu Ala Gly Ala Ala Asn
                405                 410                 415 gcc gac gtg gtg agc ctg acc tgc ccg gtc gcc gcc ggt gaa tgc gcg     1296
Ala Asp Val Val Ser Leu Thr Cys Pro Val Ala Ala Gly Glu Cys Ala
                420                 425                 430
```

| | | |
|---|---|---|
| ggc ccg gcg gac agc ggc gac gcc ctg ctg gag cgc aac tat ccc act<br>Gly Pro Ala Asp Ser Gly Asp Ala Leu Leu Glu Arg Asn Tyr Pro Thr<br>435 440 445 | | 1344 |
| ggc gcg gag ttc ctc ggc gac ggc ggc gac gtc agc ttc agc acc cgc<br>Gly Ala Glu Phe Leu Gly Asp Gly Gly Asp Val Ser Phe Ser Thr Arg<br>450 455 460 | | 1392 |
| ggc acg cag aac tgg acg gtg gag cgg ctg ctc cag gcg cac cgc caa<br>Gly Thr Gln Asn Trp Thr Val Glu Arg Leu Leu Gln Ala His Arg Gln<br>465 470 475 480 | | 1440 |
| ctg gag gag cgc ggc tat gtg ttc gtc ggc tac cac ggc acc ttc ctc<br>Leu Glu Glu Arg Gly Tyr Val Phe Val Gly Tyr His Gly Thr Phe Leu<br>485 490 495 | | 1488 |
| gaa gcg gcg caa agc atc gtc ttc ggg gtg cgc gcg cgc agc cag<br>Glu Ala Ala Gln Ser Ile Val Phe Gly Val Arg Ala Arg Ser Gln<br>500 505 510 | | 1536 |
| gac ctc gac gcg atc tgg cgc ggt ttc tat atc gcc ggc gat ccg gcg<br>Asp Leu Asp Ala Ile Trp Arg Gly Phe Tyr Ile Ala Gly Asp Pro Ala<br>515 520 525 | | 1584 |
| ctg gcc tac ggc tac gcc cag gac cag gaa ccc gac gca cgc ggc cgg<br>Leu Ala Tyr Gly Tyr Ala Gln Asp Gln Glu Pro Asp Ala Arg Gly Arg<br>530 535 540 | | 1632 |
| atc cgc aac ggt gcc ctg ctg cgg gtc tat gtg ccg cgc tcg agc ctg<br>Ile Arg Asn Gly Ala Leu Leu Arg Val Tyr Val Pro Arg Ser Ser Leu<br>545 550 555 560 | | 1680 |
| ccg ggc ttc tac cgc acc agc ctg acc ctg gcc gcg ccg gag gcg gcg<br>Pro Gly Phe Tyr Arg Thr Ser Leu Thr Leu Ala Ala Pro Glu Ala Ala<br>565 570 575 | | 1728 |
| ggc gag gtc gaa cgg ctg atc ggc cat ccg ctg ccg ctg cgc ctg gac<br>Gly Glu Val Glu Arg Leu Ile Gly His Pro Leu Pro Leu Arg Leu Asp<br>580 585 590 | | 1776 |
| gcc atc acc ggc ccc gag gag gaa ggc ggg cgc ctg gag acc att ctc<br>Ala Ile Thr Gly Pro Glu Glu Glu Gly Gly Arg Leu Glu Thr Ile Leu<br>595 600 605 | | 1824 |
| ggc tgg ccg ctg gcc gag cgc acc gtg gtg att ccc tcg gcg atc ccc<br>Gly Trp Pro Leu Ala Glu Arg Thr Val Val Ile Pro Ser Ala Ile Pro<br>610 615 620 | | 1872 |
| acc gac ccg cgc aac gtc ggc ggc gac ctc gac ccg tcc agc atc ccc<br>Thr Asp Pro Arg Asn Val Gly Gly Asp Leu Asp Pro Ser Ser Ile Pro<br>625 630 635 640 | | 1920 |
| gac aag gaa cag gcg atc agc gcc ctg ccg gac tac gcc agc cag ccc<br>Asp Lys Glu Gln Ala Ile Ser Ala Leu Pro Asp Tyr Ala Ser Gln Pro<br>645 650 655 | | 1968 |
| ggc aaa ccg ccg gac tac aag gat gac gac gat aag aaa gac gaa ctg<br>Gly Lys Pro Pro Asp Tyr Lys Asp Asp Asp Asp Lys Lys Asp Glu Leu<br>660 665 670 | | 2016 |
| tag tga | | 2022 |

<210> SEQ ID NO 25
<211> LENGTH: 672
<212> TYPE: PRT
<213> ORGANISM: Mus musculus

<400> SEQUENCE: 25

Met Lys Tyr Leu Leu Pro Thr Ala Ala Ala Gly Leu Leu Leu Leu Ala
1               5                   10                  15

Ala Gln Pro Ala Met Ala Met Asp His His His His His His
            20                  25                  30

His His Lys Leu Glu Val Gln Leu Gln Gln Ser Gly Pro Glu Leu Val
        35                  40                  45

-continued

```
Lys Pro Gly Ala Ser Val Lys Ile Ser Cys Lys Thr Ser Gly Tyr Thr
 50                  55                  60

Phe Thr Glu Tyr Thr Met His Trp Val Lys Gln Ser His Gly Lys Ser
 65                  70                  75                  80

Leu Glu Trp Ile Gly Gly Ile Asn Pro Asn Asn Gly Gly Thr Ser Tyr
                 85                  90                  95

Asn Gln Lys Phe Lys Gly Lys Ala Thr Leu Thr Val Asp Lys Ser Ser
            100                 105                 110

Ser Thr Ala Tyr Met Glu Leu Arg Ser Leu Thr Ser Glu Asp Ser Ala
        115                 120                 125

Val Tyr Tyr Cys Ala Arg Glu Lys Tyr Gly Asn Tyr Tyr Ala Met Asp
    130                 135                 140

Tyr Trp Gly Gln Gly Thr Ser Val Thr Val Ser Ser Gly Gly Gly Gly
145                 150                 155                 160

Ser Gly Gly Gly Gly Ser Gly Gly Gly Gly Ser Asp Ile Val Met Ser
                165                 170                 175

Gln Ser Pro Ser Ser Leu Ala Val Ser Ala Gly Glu Lys Val Thr Met
            180                 185                 190

Ser Cys Lys Ser Ser Gln Ser Leu Leu Asn Ser Arg Thr Arg Lys Asn
        195                 200                 205

Tyr Leu Ala Trp Tyr Gln Gln Lys Pro Gly Gln Ser Pro Lys Leu Leu
    210                 215                 220

Ile Tyr Trp Ala Ser Thr Arg Glu Ser Gly Val Pro Asp Arg Phe Thr
225                 230                 235                 240

Gly Ser Gly Ser Gly Thr Asp Phe Thr Leu Thr Ile Ser Ser Val Gln
                245                 250                 255

Ala Glu Asp Leu Ala Val Tyr Tyr Cys Lys Gln Ser Tyr Asn Leu Arg
            260                 265                 270

Thr Phe Gly Gly Gly Thr Lys Leu Glu Ile Lys Glu Phe Gly Gly Ala
        275                 280                 285

Pro Glu Phe Pro Lys Pro Ser Thr Pro Pro Gly Ser Ser Gly Leu Glu
    290                 295                 300

Gly Gly Ser Leu Ala Ala Leu Thr Ala His Gln Ala Cys His Leu Pro
305                 310                 315                 320

Leu Glu Thr Phe Thr Arg His Arg Gln Pro Arg Gly Trp Glu Gln Leu
                325                 330                 335

Glu Gln Cys Gly Tyr Pro Val Gln Arg Leu Val Ala Leu Tyr Leu Ala
            340                 345                 350

Ala Arg Leu Ser Trp Asn Gln Val Asp Gln Val Ile Arg Asn Ala Leu
        355                 360                 365

Ala Ser Pro Gly Ser Gly Gly Asp Leu Gly Glu Ala Ile Arg Glu Gln
    370                 375                 380

Pro Glu Gln Ala Arg Leu Ala Leu Thr Leu Ala Ala Ala Glu Ser Glu
385                 390                 395                 400

Arg Phe Val Arg Gln Gly Thr Gly Asn Asp Glu Ala Gly Ala Ala Asn
                405                 410                 415

Ala Asp Val Val Ser Leu Thr Cys Pro Val Ala Ala Gly Glu Cys Ala
            420                 425                 430

Gly Pro Ala Asp Ser Gly Asp Ala Leu Leu Glu Arg Asn Tyr Pro Thr
        435                 440                 445

Gly Ala Glu Phe Leu Gly Asp Gly Gly Asp Val Ser Phe Ser Thr Arg
    450                 455                 460

Gly Thr Gln Asn Trp Thr Val Glu Arg Leu Leu Gln Ala His Arg Gln
465                 470                 475                 480
```

-continued

```
Leu Glu Glu Arg Gly Tyr Val Phe Val Gly Tyr His Gly Thr Phe Leu
            485                 490                 495

Glu Ala Ala Gln Ser Ile Val Phe Gly Gly Val Arg Ala Arg Ser Gln
        500                 505                 510

Asp Leu Asp Ala Ile Trp Arg Gly Phe Tyr Ile Ala Gly Asp Pro Ala
        515                 520                 525

Leu Ala Tyr Gly Tyr Ala Gln Asp Gln Glu Pro Asp Ala Arg Gly Arg
    530                 535                 540

Ile Arg Asn Gly Ala Leu Leu Arg Val Tyr Val Pro Arg Ser Ser Leu
545                 550                 555                 560

Pro Gly Phe Tyr Arg Thr Ser Leu Thr Leu Ala Ala Pro Glu Ala Ala
                565                 570                 575

Gly Glu Val Glu Arg Leu Ile Gly His Pro Leu Pro Leu Arg Leu Asp
            580                 585                 590

Ala Ile Thr Gly Pro Glu Glu Glu Gly Gly Arg Leu Glu Thr Ile Leu
        595                 600                 605

Gly Trp Pro Leu Ala Glu Arg Thr Val Val Ile Pro Ser Ala Ile Pro
    610                 615                 620

Thr Asp Pro Arg Asn Val Gly Gly Asp Leu Asp Pro Ser Ser Ile Pro
625                 630                 635                 640

Asp Lys Glu Gln Ala Ile Ser Ala Leu Pro Asp Tyr Ala Ser Gln Pro
                645                 650                 655

Gly Lys Pro Pro Asp Tyr Lys Asp Asp Asp Lys Lys Asp Glu Leu
            660                 665                 670

<210> SEQ ID NO 26
<211> LENGTH: 20
<212> TYPE: DNA
<213> ORGANISM: Artificial
<220> FEATURE:
<223> OTHER INFORMATION: Primer for amplifying full-length Grp78 gene.

<400> SEQUENCE: 26
atgaagctct ccctggtggc                                                 20

<210> SEQ ID NO 27
<211> LENGTH: 25
<212> TYPE: DNA
<213> ORGANISM: Artificial
<220> FEATURE:
<223> OTHER INFORMATION: Primer for amplifying full-length Grp78 gene.

<400> SEQUENCE: 27
ctacaactca tcttttctg ctgta                                            25

<210> SEQ ID NO 28
<211> LENGTH: 38
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 28
aaaggatccg aggaggagga caagaaggag gacgtggg                             38

<210> SEQ ID NO 29
<211> LENGTH: 39
<212> TYPE: DNA
<213> ORGANISM: Artificial
<220> FEATURE:
```

-continued

<223> OTHER INFORMATION: Primer for amplifying subsequence of GST-Grp78
      fusion gene.

<400> SEQUENCE: 29
tttctcgagc tacaactcat cttttttctgc tgtatcctc                              39

<210> SEQ ID NO 30
<211> LENGTH: 43
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 30
tttctcgagc taatcagaat cttccaacac tttctggacg ggc                          43

<210> SEQ ID NO 31
<211> LENGTH: 34
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 31
aaaggatccc ggcgcgaggt agaaaaggcc aaac                                    34

<210> SEQ ID NO 32
<211> LENGTH: 35
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 32
ttctcgagct aggtaggcac cactgtgttc cttgg                                   35

<210> SEQ ID NO 33
<211> LENGTH: 35
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 33
ttctcgagct agatttcttc aggtgtcagg cgatt                                   35

<210> SEQ ID NO 34
<211> LENGTH: 34
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 34
tttggatccg tgttggaaga ttctgatttg aaga                                    34

<210> SEQ ID NO 35
<211> LENGTH: 35
<212> TYPE: DNA
<213> ORGANISM: Artificial
<220> FEATURE:
<223> OTHER INFORMATION: Primer for amplifying subsequence of GST-Grp78
      fusion gene.

-continued

<400> SEQUENCE: 35
ttctcgagct aggatggttc cttgccattg aagaa        35

<210> SEQ ID NO 36
<211> LENGTH: 32
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 36
aaaggatcca aagagttctt caatggcaag ga        32

<210> SEQ ID NO 37
<211> LENGTH: 35
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 37
ttctcgagct ataccaggtc acctgtatct tgatc        35

<210> SEQ ID NO 38
<211> LENGTH: 33
<212> TYPE: DNA
<213> ORGANISM: Artificial
<220> FEATURE:
<223> OTHER INFORMATION: Primer for amplifying subsequence of GST-Grp78
      fusion gene.

<400> SEQUENCE: 38
aaaggatcct ctggtgatca agatacaggt gac        33

<210> SEQ ID NO 39
<211> LENGTH: 23
<212> TYPE: DNA
<213> ORGANISM: Artificial
<220> FEATURE:
<223> OTHER INFORMATION: Primer for cloning a nucleotide sequence
      encoding light-chain variable region of GA-20 antibody.

<400> SEQUENCE: 39
gctcactgga tggtgggaag atg        23

<210> SEQ ID NO 40
<211> LENGTH: 23
<212> TYPE: DNA
<213> ORGANISM: Artificial
<220> FEATURE:
<223> OTHER INFORMATION: Primer for cloning a nucleotide sequence
      encoding heavy-chain variable region of GA-20 antibody.

<400> SEQUENCE: 40
ccaccagatt cttatcagac agg        23

<210> SEQ ID NO 41
<211> LENGTH: 87
<212> TYPE: DNA
<213> ORGANISM: Artificial
<220> FEATURE:
<223> OTHER INFORMATION: Primer for generating a nucleotide sequence
      encoding a single chain Fv derived from GA-20 antibody.

<400> SEQUENCE: 41

```
taagaattcg gtggcgcgcc ggagttcccg aaaccgtcca ccccgccggg ttcttctggt    60
ttagagggcg gcagcctggc cgcgctg                                       87
```

<210> SEQ ID NO 42
<211> LENGTH: 75
<212> TYPE: DNA
<213> ORGANISM: Artificial
<220> FEATURE:
<223> OTHER INFORMATION: Primer for generating a nucleotide sequence
      encoding a single chain Fv derived from GA-20 antibody.

<400> SEQUENCE: 42

```
acttagcggc cgctcactac agttcgtctt tcttatcgtc gtcatccttg tagtccggcg    60
gtttgccggg ctggc                                                    75
```

<210> SEQ ID NO 43
<211> LENGTH: 15
<212> TYPE: PRT
<213> ORGANISM: Artificial
<220> FEATURE:
<223> OTHER INFORMATION: Linker polypeptide of scFv sntibody.

<400> SEQUENCE: 43

```
Gly Gly Gly Gly Ser Gly Gly Gly Gly Ser Gly Gly Gly Gly Ser
1               5                   10                  15
```

<210> SEQ ID NO 44
<211> LENGTH: 31
<212> TYPE: DNA
<213> ORGANISM: Artificial
<220> FEATURE:
<223> OTHER INFORMATION: Primer for amplifying a nucleotide sequence
      encoding a single chain Fv derived from GA-20 antibody.

<400> SEQUENCE: 44

```
aaaagcttga ggtccagctg caacagtctg g                                  31
```

<210> SEQ ID NO 45
<211> LENGTH: 56
<212> TYPE: DNA
<213> ORGANISM: Artificial
<220> FEATURE:
<223> OTHER INFORMATION: Primer for amplifying a nucleotide sequence
      encoding a single chain Fv derived from GA-20 antibody.

<400> SEQUENCE: 45

```
cccgaaccac caccacccga accaccacca cctgaggaga cggtgactga ggttcc        56
```

<210> SEQ ID NO 46
<211> LENGTH: 65
<212> TYPE: DNA
<213> ORGANISM: Artificial
<220> FEATURE:
<223> OTHER INFORMATION: Primer for amplifying a nucleotide sequence
      encoding a single chain Fv derived from GA-20 antibody.

<400> SEQUENCE: 46

```
tggttcgggt ggtggtggtt cgggtggtgg cggatcggac attgtgatgt cacagtctcc    60
atcct                                                               65
```

<210> SEQ ID NO 47
<211> LENGTH: 31
<212> TYPE: DNA
<213> ORGANISM: Artificial
<220> FEATURE:

```
<223> OTHER INFORMATION: Primer for amplifying a nucleotide sequence
      encoding a single chain Fv derived from GA-20 antibody.

<400> SEQUENCE: 47
ttgaattctt tgatttccag cttggtgcct c                              31

<210> SEQ ID NO 48
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (376-391) region.

<400> SEQUENCE: 48
gatccaaaga gttcttcaat ggcaaggaac catcccgtgg cataaaccca gatc     54

<210> SEQ ID NO 49
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (376-391) region.

<400> SEQUENCE: 49
tcgagatctg ggtttatgcc acgggatggt tccttgccat tgaagaactc tttg     54

<210> SEQ ID NO 50
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (384-399) region.

<400> SEQUENCE: 50
gatccccatc ccgtggcata aacccagatg aagctgtagc gtatggtgct gctc     54

<210> SEQ ID NO 51
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (384-399) region.

<400> SEQUENCE: 51
tcgagagcag caccatacgc tacagcttca tctgggttta tgccacggga tggg     54

<210> SEQ ID NO 52
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (392-407) region.

<400> SEQUENCE: 52
gatccgaagc tgtagcgtat ggtgctgctg tccaggctgg tgtgctctct ggtc     54

<210> SEQ ID NO 53
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (392-407) region.
```

-continued

<210> SEQ ID NO 53
<400> SEQUENCE: 53
tcgagaccag agagcacacc agcctggaca gcagcaccat acgctacagc ttcg        54

<210> SEQ ID NO 54
<211> LENGTH: 54
<212> TYPE: DNA
<213> ORGANISM: Artificial
<220> FEATURE:
<223> OTHER INFORMATION: Primer for amplifying a nucleotide sequence
      corresponding to GRP78 (400-415) region.

<400> SEQUENCE: 54
gatccgtcca ggctggtgtg ctctctggtg atcaagatac aggtgacctg gtac        54

<210> SEQ ID NO 55
<211> LENGTH: 53
<212> TYPE: DNA
<213> ORGANISM: Artificial
<220> FEATURE:
<223> OTHER INFORMATION: Primer for amplifying a nucleotide sequence
      corresponding to GRP78 (400-415) region.

<400> SEQUENCE: 55
tcgagtacca ggtcacctgt atcttgatca ccagagagca caccagcctg gac         53

<210> SEQ ID NO 56
<211> LENGTH: 23
<212> TYPE: DNA
<213> ORGANISM: Artificial
<220> FEATURE:
<223> OTHER INFORMATION: Primer for cloning a nucleotide sequence
      encoding heavy-chain variable region of GC-18, GC-20, GD-4, and
      GD-17 antibodies.

<400> SEQUENCE: 56
ccaccagatt cttatcagac agg                                          23

<210> SEQ ID NO 57
<211> LENGTH: 402
<212> TYPE: DNA
<213> ORGANISM: Mus musculus

<400> SEQUENCE: 57
atgagagtgt tgattcttgt gtacctgttg acagcccttc ctggtatctt gtcagatgta    60
cggcttcagg agtcaggacc tggccaggtg aagccttctc agacagtgtc cctcacctgc   120
tctgtcactg gctactctat cactaatggt aatcactggt ggaactggat ccggcaggtt   180
tcaggatcca aactggagtg gatagggtac ataagttcca gtggtagcac tgacagcaat   240
ccatctctca aaagtcgaat ctccatcact agagacactt ccaagaacca gttattcctg   300
cagttgaact ctgtgactac tgaagatata gccacatatt actgtgcaag aggctactac   360
tttgactact ggggccaagg caccactctc acagtctcct ca                     402

<210> SEQ ID NO 58
<211> LENGTH: 116
<212> TYPE: PRT
<213> ORGANISM: Mus musculus

<400> SEQUENCE: 58

Asp Val Arg Leu Gln Glu Ser Gly Pro Gly Gln Val Lys Pro Ser Gln
1               5                   10                  15

Thr Val Ser Leu Thr Cys Ser Val Thr Gly Tyr Ser Ile Thr Asn Gly
            20                  25                  30

Asn His Trp Trp Asn Trp Ile Arg Gln Val Ser Gly Ser Lys Leu Glu
             35                  40                  45

Trp Ile Gly Tyr Ile Ser Ser Gly Ser Thr Asp Ser Asn Pro Ser
 50                  55                  60

Leu Lys Ser Arg Ile Ser Ile Thr Arg Asp Thr Ser Lys Asn Gln Leu
 65                  70                  75                  80

Phe Leu Gln Leu Asn Ser Val Thr Thr Glu Asp Ile Ala Thr Tyr Tyr
                 85                  90                  95

Cys Ala Arg Gly Tyr Tyr Phe Asp Tyr Trp Gly Gln Gly Thr Thr Leu
                100                 105                 110

Thr Val Ser Ser
            115

<210> SEQ ID NO 59
<211> LENGTH: 393
<212> TYPE: DNA
<213> ORGANISM: Mus musculus

<400> SEQUENCE: 59
atggagacag acacactcct gctatgggtg ctgctgctct gggttccagg ctccactggt    60
gacattgtgc tcacccaatc tccagcttct ttggctgtgt ctctagggca gagtgtcacc   120
atctcctgca gagccagtga aagtgttgaa tattatggca ctagtttaat gcagtggtac   180
caacagaaac aggacagcc acccaaactc ctcatctatg ctacatccaa cgtggaatct   240
ggggtccctg ccaggtttag tggcagtggg tctgggacag acttcagcct caacatccat   300
cctgtggagg aggatgatat tgcaatgtat ttctgtcagc aaagtaggaa acttccttcg   360
acgttcggtg gaggcaccaa gctggaaatc aaa                                393

<210> SEQ ID NO 60
<211> LENGTH: 111
<212> TYPE: PRT
<213> ORGANISM: Mus musculus

<400> SEQUENCE: 60

Asp Ile Val Leu Thr Gln Ser Pro Ala Ser Leu Ala Val Ser Leu Gly
 1               5                  10                  15

Gln Ser Val Thr Ile Ser Cys Arg Ala Ser Glu Ser Val Glu Tyr Tyr
             20                  25                  30

Gly Thr Ser Leu Met Gln Trp Tyr Gln Gln Lys Pro Gly Gln Pro Pro
             35                  40                  45

Lys Leu Leu Ile Tyr Ala Thr Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Leu Pro Ser Thr Phe Gly Gly Gly Thr Lys Leu Glu Ile Lys
            100                 105                 110

<210> SEQ ID NO 61
<211> LENGTH: 7
<212> TYPE: PRT
<213> ORGANISM: Mus musculus

<400> SEQUENCE: 61

Asn Gly Asn His Trp Trp Asn
 1               5

-continued

<210> SEQ ID NO 62
<211> LENGTH: 16
<212> TYPE: PRT
<213> ORGANISM: Mus musculus

<400> SEQUENCE: 62

Tyr Ile Ser Ser Ser Gly Ser Thr Asp Ser Asn Pro Ser Leu Lys Ser
1               5                   10                  15

<210> SEQ ID NO 63
<211> LENGTH: 6
<212> TYPE: PRT
<213> ORGANISM: Mus musculus

<400> SEQUENCE: 63

Gly Tyr Tyr Phe Asp Tyr
1               5

<210> SEQ ID NO 64
<211> LENGTH: 15
<212> TYPE: PRT
<213> ORGANISM: Mus musculus

<400> SEQUENCE: 64

Arg Ala Ser Glu Ser Val Glu Tyr Tyr Gly Thr Ser Leu Met Gln
1               5                   10                  15

<210> SEQ ID NO 65
<211> LENGTH: 7
<212> TYPE: PRT
<213> ORGANISM: Mus musculus

<400> SEQUENCE: 65

Ala Thr Ser Asn Val Glu Ser
1               5

<210> SEQ ID NO 66
<211> LENGTH: 9
<212> TYPE: PRT
<213> ORGANISM: Mus musculus

<400> SEQUENCE: 66

Gln Gln Ser Arg Lys Leu Pro Ser Thr
1               5

<210> SEQ ID NO 67
<211> LENGTH: 402
<212> TYPE: DNA
<213> ORGANISM: Mus musculus

<400> SEQUENCE: 67
atgagagtgt tgattcctgt gtacctgttg acagcccttc ctggtatctt gtctgatgta      60
cgacttcagg agtcaggacc tggcctggtg aagccttctc agacagtgtc cctcacctgc     120
actgtcactg gctactctat cactaatggt aatcactggt ggaactggat ccggcaggtt     180
tcaggaagca aactggagtg gatagggtac ataagctcca gtggtagcac tgacagcaat     240
ccatctctca aaagtcgaat ctccatcact agagacactt ccaagaacca gttattcctg     300
cagttgaact ctgtgactac tgaagatata gccacatatt actgtgcaag aggctactac     360
tttgactact ggggccaagg caccactctc acagtctcct ca                        402

<210> SEQ ID NO 68

```
<211> LENGTH: 116
<212> TYPE: PRT
<213> ORGANISM: Mus musculus

<400> SEQUENCE: 68

Asp Val Arg Leu Gln Glu Ser Gly Pro Gly Leu Val Lys Pro Ser Gln
1               5                   10                  15

Thr Val Ser Leu Thr Cys Thr Val Thr Gly Tyr Ser Ile Thr Asn Gly
            20                  25                  30

Asn His Trp Asn Trp Ile Arg Gln Val Ser Gly Ser Lys Leu Glu
        35                  40                  45

Trp Ile Gly Tyr Ile Ser Ser Gly Ser Thr Asp Ser Asn Pro Ser
    50                  55                  60

Leu Lys Ser Arg Ile Ser Ile Thr Arg Asp Thr Ser Lys Asn Gln Leu
65                  70                  75                  80

Phe Leu Gln Leu Asn Ser Val Thr Thr Glu Asp Ile Ala Thr Tyr Tyr
                85                  90                  95

Cys Ala Arg Gly Tyr Tyr Phe Asp Tyr Trp Gly Gln Gly Thr Thr Leu
            100                 105                 110

Thr Val Ser Ser
            115

<210> SEQ ID NO 69
<211> LENGTH: 408
<212> TYPE: DNA
<213> ORGANISM: Mus musculus

<400> SEQUENCE: 69
atgcatcaga ccagcatggg catcaagatg gaatcacaga ctctggtcct catatccata     60
ctgctctggt tatatggagc tgatgggaac attgtaatga cccaatctcc caaatccatg    120
tccatgtcag taggagagag ggtcaccttg acctgcaagg ccagtgagaa tgtggttact    180
tatgtttcct ggtatcaaca gaaaccagag cagtctccta aactgctgat atacggggca    240
tccaaccggt acactggggt ccccgatcgc ttcacaggca gtggatctgc aacagatttc    300
actctgacca tcagcagtgt gcaggctgaa gaccttgcag attatcactg tggacagggt    360
tacagctatc cgtacacgtt cggagggggg accaagctgg aaataaaa               408

<210> SEQ ID NO 70
<211> LENGTH: 107
<212> TYPE: PRT
<213> ORGANISM: Mus musculus

<400> SEQUENCE: 70

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105
```

```
<210> SEQ ID NO 71
<211> LENGTH: 7
<212> TYPE: PRT
<213> ORGANISM: Mus musculus

<400> SEQUENCE: 71

Asn Gly Asn His Trp Trp Asn
1               5

<210> SEQ ID NO 72
<211> LENGTH: 16
<212> TYPE: PRT
<213> ORGANISM: Mus musculus

<400> SEQUENCE: 72

Tyr Ile Ser Ser Ser Gly Ser Thr Asp Ser Asn Pro Ser Leu Lys Ser
1               5                   10                  15

<210> SEQ ID NO 73
<211> LENGTH: 6
<212> TYPE: PRT
<213> ORGANISM: Mus musculus

<400> SEQUENCE: 73

Gly Tyr Tyr Phe Asp Tyr
1               5

<210> SEQ ID NO 74
<211> LENGTH: 11
<212> TYPE: PRT
<213> ORGANISM: Mus musculus

<400> SEQUENCE: 74

Lys Ala Ser Glu Asn Val Val Thr Tyr Val Ser
1               5                   10

<210> SEQ ID NO 75
<211> LENGTH: 7
<212> TYPE: PRT
<213> ORGANISM: Mus musculus

<400> SEQUENCE: 75

Gly Ala Ser Asn Arg Tyr Thr
1               5

<210> SEQ ID NO 76
<211> LENGTH: 9
<212> TYPE: PRT
<213> ORGANISM: Mus musculus

<400> SEQUENCE: 76

Gly Gln Gly Tyr Ser Tyr Pro Tyr Thr
1               5

<210> SEQ ID NO 77
<211> LENGTH: 423
<212> TYPE: DNA
<213> ORGANISM: Mus musculus

<400> SEQUENCE: 77
atgctgttgg ggctgaagtg ggttttcttt gttgtttttt atcaaggtgt gcattgtgag     60
gtgcagcttg ttgagactgg tgaggattg gtgcagccta aagggtcatt gaaactctca    120
tgtgcagcct ctggattcac cttcaatacc aatgccatga actgggtccg ccaggctcca    180
```

-continued

```
ggaaagggtt tggaatgggt tgctcgcata agaagtaaaa gtaataatta tgcagcatat    240
tatgccgatt cagtgaaaga caggttcacc atctccagag atgattcaca aagcatgctc    300
tatctgcaaa tgaacaactt gaaaactgag acacagcca tgtattactg tgtgagagaa     360
ggctacggtt atagcttata ttttgactac tggggccaag gcaccactct cacagtctcc    420
tca                                                                  423
```

<210> SEQ ID NO 78
<211> LENGTH: 122
<212> TYPE: PRT
<213> ORGANISM: Mus musculus

<400> SEQUENCE: 78

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Ala Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Glu Gly Tyr Gly Tyr Ser Leu Tyr Phe Asp Tyr Trp
            100                 105                 110

Gly Gln Gly Thr Thr Leu Thr Val Ser Ser
        115                 120

<210> SEQ ID NO 79
<211> LENGTH: 399
<212> TYPE: DNA
<213> ORGANISM: Mus musculus

<400> SEQUENCE: 79

```
atggagtttc agacccaggt actcatgtcc ctgctgctct gcatgtctgg tgcctgtgca    60
gacattgtga tgactcagtc tccaactttc cttgctgtga cagcaagtaa gaaggtcacc    120
attaattgca cggccagtga gagcctttat tcaagcaaac acaaggtgca ctacttggct    180
tggtaccaga agaaaccaga tcaatctcct aaactgctga tatacggggc atccaaccga    240
tacattgggg tccctgatcg cttcacaggc agtggatctg ggacagattt cactctgacc    300
atcagcagtg tacaggttga agacctcaca cattattact gtgcacagtt ttacagctat    360
cctctcacgt tcggtgctgg gaccaagctg gagctgaaa                           399
```

<210> SEQ ID NO 80
<211> LENGTH: 113
<212> TYPE: PRT
<213> ORGANISM: Mus musculus

<400> SEQUENCE: 80

Asp Ile Val Met Thr Gln Ser Pro Thr Phe Leu Ala Val Thr Ala Ser
1               5                   10                  15

Lys Lys Val Thr Ile Asn Cys Thr Ala Ser Glu Ser Leu Tyr Ser Ser
            20                  25                  30

Lys His Lys Val His Tyr Leu Ala Trp Tyr Gln Lys Lys Pro Asp Gln

-continued

```
                35                  40                  45
Ser Pro Lys Leu Leu Ile Tyr Gly Ala Ser Asn Arg Tyr Ile Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Val Glu Asp Leu Thr His Tyr Tyr Cys Ala Gln
                 85                  90                  95

Phe Tyr Ser Tyr Pro Leu Thr Phe Gly Ala Gly Thr Lys Leu Glu Leu
            100                 105                 110

Lys

<210> SEQ ID NO 81
<211> LENGTH: 5
<212> TYPE: PRT
<213> ORGANISM: Mus musculus

<400> SEQUENCE: 81

Thr Asn Ala Met Asn
 1               5

<210> SEQ ID NO 82
<211> LENGTH: 19
<212> TYPE: PRT
<213> ORGANISM: Mus musculus

<400> SEQUENCE: 82

Arg Ile Arg Ser Lys Ser Asn Asn Tyr Ala Ala Tyr Tyr Ala Asp Ser
 1               5                  10                  15

Val Lys Asp

<210> SEQ ID NO 83
<211> LENGTH: 11
<212> TYPE: PRT
<213> ORGANISM: Mus musculus

<400> SEQUENCE: 83

Glu Gly Tyr Gly Tyr Ser Leu Tyr Phe Asp Tyr
 1               5                  10

<210> SEQ ID NO 84
<211> LENGTH: 17
<212> TYPE: PRT
<213> ORGANISM: Mus musculus

<400> SEQUENCE: 84

Thr Ala Ser Glu Ser Leu Tyr Ser Ser Lys His Lys Val His Tyr Leu
 1               5                  10                  15

Ala

<210> SEQ ID NO 85
<211> LENGTH: 7
<212> TYPE: PRT
<213> ORGANISM: Mus musculus

<400> SEQUENCE: 85

Gly Ala Ser Asn Arg Tyr Ile
 1               5

<210> SEQ ID NO 86
<211> LENGTH: 9
<212> TYPE: PRT
<213> ORGANISM: Mus musculus
```

<400> SEQUENCE: 86

Ala Gln Phe Tyr Ser Tyr Pro Leu Thr
1               5

<210> SEQ ID NO 87
<211> LENGTH: 408
<212> TYPE: DNA
<213> ORGANISM: Mus musculus

<400> SEQUENCE: 87

```
atggaatgta actggatact tcctttattt ctgtcagtaa cttcaggtgt ctactcacag      60
gttcagctcc agcagtctgg ggctgaactg gcaagacctg ggcttcagt gaagttgtcc     120
tgcaaggctt ctggctacac ctttactagc tactggatgc attgggtaaa acagaggcct    180
ggacagggtc tggaatggat tgggctatt tatcctggag atggtgatac taggtacact     240
cagaagttca agggcaaggc cacattgact gcagataaat cctccagcac agcctacatg    300
caactcagca gcttggcatc tgaggactct gcggtctatt actgtgcaag cggaattact    360
gcggtagccg actactgggg ccaaggcacc actctcacag tctcctca                  408
```

<210> SEQ ID NO 88
<211> LENGTH: 117
<212> TYPE: PRT
<213> ORGANISM: Mus musculus

<400> SEQUENCE: 88

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Ser Gly Ile Thr Ala Val Ala Asp Tyr Trp Gly Gln Gly Thr Thr
            100                 105                 110

Leu Thr Val Ser Ser
        115

<210> SEQ ID NO 89
<211> LENGTH: 393
<212> TYPE: DNA
<213> ORGANISM: Mus musculus

<400> SEQUENCE: 89

```
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgattttct      240
ggggtcccag acaggttcag tggcagtgga tcagggacag attcacact caagatcagc     300
agagtggagg ctgaggatct gggagtttat ttctgctctc aaagtacaca tgttccgctc    360
```
acgttcggtg ctgggaccaa gctggagctg aaa                               393

<210> SEQ ID NO 90
<211> LENGTH: 112
<212> TYPE: PRT
<213> ORGANISM: Mus musculus

<400> SEQUENCE: 90

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 91
<211> LENGTH: 5
<212> TYPE: PRT
<213> ORGANISM: Mus musculus

<400> SEQUENCE: 91

Ser Tyr Trp Met His
1               5

<210> SEQ ID NO 92
<211> LENGTH: 17
<212> TYPE: PRT
<213> ORGANISM: Mus musculus

<400> SEQUENCE: 92

Ala Ile Tyr Pro Gly Asp Gly Asp Thr Arg Tyr Thr Gln Lys Phe Lys
1               5                   10                  15

Gly

<210> SEQ ID NO 93
<211> LENGTH: 8
<212> TYPE: PRT
<213> ORGANISM: Mus musculus

<400> SEQUENCE: 93

Gly Ile Thr Ala Val Ala Asp Tyr
1               5

<210> SEQ ID NO 94
<211> LENGTH: 16
<212> TYPE: PRT
<213> ORGANISM: Mus musculus

<400> SEQUENCE: 94

Arg Ser Ser Gln Ser Leu Val His Ser Asn Gly Asn Thr Tyr Leu His
1               5                   10                  15

<210> SEQ ID NO 95
<211> LENGTH: 7

```
<212> TYPE: PRT
<213> ORGANISM: Mus musculus

<400> SEQUENCE: 95

Lys Val Ser Asn Arg Phe Ser
1               5

<210> SEQ ID NO 96
<211> LENGTH: 9
<212> TYPE: PRT
<213> ORGANISM: Mus musculus

<400> SEQUENCE: 96

Ser Gln Ser Thr His Val Pro Leu Thr
1               5

<210> SEQ ID NO 97
<211> LENGTH: 31
<212> TYPE: DNA
<213> ORGANISM: Artificial
<220> FEATURE:
<223> OTHER INFORMATION: Sense primer for amplifying a nucleotide
      sequence encoding heavy-chain variable region of GD-17 antibody.

<400> SEQUENCE: 97
aaaagcttca ggttcagctc cagcagtctg g                              31

<210> SEQ ID NO 98
<211> LENGTH: 57
<212> TYPE: DNA
<213> ORGANISM: Artificial
<220> FEATURE:
<223> OTHER INFORMATION: Antisense primer for amplifying a nucleotide
      sequence encoding heavy-chain variable region of GD-17 antibody.

<400> SEQUENCE: 98
cccgaaccac caccacccga accaccacca cctgaggaga ctgtgagagt ggtgcct    57

<210> SEQ ID NO 99
<211> LENGTH: 62
<212> TYPE: DNA
<213> ORGANISM: Artificial
<220> FEATURE:
<223> OTHER INFORMATION: Sense primer for amplifying a nucleotide
      sequence encoding light-chain variable region of GD-17 antibody.

<400> SEQUENCE: 99
tggttcgggt ggtggtggtt cgggtggtgg cggatcggat gttgtgatga cccaaactcc  60
ac                                                                62

<210> SEQ ID NO 100
<211> LENGTH: 29
<212> TYPE: DNA
<213> ORGANISM: Artificial
<220> FEATURE:
<223> OTHER INFORMATION: Antisense primer for amplifying a nucleotide
      sequence encoding light-chain variable region of GD-17 antibody.

<400> SEQUENCE: 100
ttgaattctt tcagctccag cttggtccc                                 29

<210> SEQ ID NO 101
<211> LENGTH: 2013
<212> TYPE: DNA
<213> ORGANISM: Mus musculus
<220> FEATURE:
<221> NAME/KEY: CDS
```

<222> LOCATION: (1)..(2013)

<400> SEQUENCE: 101

| | | | | | | | | | | | | | | | | |
|---|---|---|---|---|---|---|---|---|---|---|---|---|---|---|---|---|
| atg | aaa | tac | ctg | ctg | ccg | acc | gct | gct | gct | ggt | ctg | ctg | ctc | ctc | gct | 48 |
| Met | Lys | Tyr | Leu | Leu | Pro | Thr | Ala | Ala | Ala | Gly | Leu | Leu | Leu | Leu | Ala | |
| 1 | | | | 5 | | | | | 10 | | | | | 15 | | |
| gcc | cag | ccg | gcg | atg | gcc | atg | gat | cac | cat | cac | cat | cac | cat | cac | cat | 96 |
| Ala | Gln | Pro | Ala | Met | Ala | Met | Asp | His | His | His | His | His | His | His | His | |
| | | | 20 | | | | | 25 | | | | | 30 | | | |
| cat | cac | aag | ctt | cag | gtt | cag | ctc | cag | cag | tct | ggg | gct | gaa | ctg | gca | 144 |
| His | His | Lys | Leu | Gln | Val | Gln | Leu | Gln | Gln | Ser | Gly | Ala | Glu | Leu | Ala | |
| | | 35 | | | | | 40 | | | | | 45 | | | | |
| aga | cct | ggg | gct | tca | gtg | aag | ttg | tcc | tgc | aag | gct | tct | ggc | tac | acc | 192 |
| Arg | Pro | Gly | Ala | Ser | Val | Lys | Leu | Ser | Cys | Lys | Ala | Ser | Gly | Tyr | Thr | |
| 50 | | | | | 55 | | | | | 60 | | | | | | |
| ttt | act | agc | tac | tgg | atg | cat | tgg | gta | aaa | cag | agg | cct | gga | cag | ggt | 240 |
| Phe | Thr | Ser | Tyr | Trp | Met | His | Trp | Val | Lys | Gln | Arg | Pro | Gly | Gln | Gly | |
| 65 | | | | | 70 | | | | | 75 | | | | | 80 | |
| ctg | gaa | tgg | att | ggg | gct | att | tat | cct | gga | gat | ggt | gat | act | agg | tac | 288 |
| Leu | Glu | Trp | Ile | Gly | Ala | Ile | Tyr | Pro | Gly | Asp | Gly | Asp | Thr | Arg | Tyr | |
| | | | | 85 | | | | | 90 | | | | | 95 | | |
| act | cag | aag | ttc | aag | ggc | aag | gcc | aca | ttg | act | gca | gat | aaa | tcc | tcc | 336 |
| Thr | Gln | Lys | Phe | Lys | Gly | Lys | Ala | Thr | Leu | Thr | Ala | Asp | Lys | Ser | Ser | |
| | | | | 100 | | | | | 105 | | | | | 110 | | |
| agc | aca | gcc | tac | atg | caa | ctc | agc | agc | ttg | gca | tct | gag | gac | tct | gcg | 384 |
| Ser | Thr | Ala | Tyr | Met | Gln | Leu | Ser | Ser | Leu | Ala | Ser | Glu | Asp | Ser | Ala | |
| | | 115 | | | | | 120 | | | | | 125 | | | | |
| gtc | tat | tac | tgt | gca | agc | gga | att | act | gcg | gta | gcc | gac | tac | tgg | ggc | 432 |
| Val | Tyr | Tyr | Cys | Ala | Ser | Gly | Ile | Thr | Ala | Val | Ala | Asp | Tyr | Trp | Gly | |
| 130 | | | | | 135 | | | | | 140 | | | | | | |
| caa | ggc | acc | act | ctc | aca | gtc | tcc | tca | ggt | ggt | ggt | ggt | tcg | ggt | ggt | 480 |
| Gln | Gly | Thr | Thr | Leu | Thr | Val | Ser | Ser | Gly | Gly | Gly | Gly | Ser | Gly | Gly | |
| 145 | | | | | 150 | | | | | 155 | | | | | 160 | |
| ggt | ggt | tcg | ggt | ggt | ggc | gga | tcg | gat | gtt | gtg | atg | acc | caa | act | cca | 528 |
| Gly | Gly | Ser | Gly | Gly | Gly | Gly | Ser | Asp | Val | Val | Met | Thr | Gln | Thr | Pro | |
| | | | | 165 | | | | | 170 | | | | | 175 | | |
| ctc | tcc | ctg | cct | gtc | agt | ctt | gga | gat | caa | gcc | tcc | atc | tct | tgc | aga | 576 |
| Leu | Ser | Leu | Pro | Val | Ser | Leu | Gly | Asp | Gln | Ala | Ser | Ile | Ser | Cys | Arg | |
| | | | 180 | | | | | 185 | | | | | 190 | | | |
| tct | agt | cag | agc | ctt | gta | cac | agt | aat | gga | aac | acc | tat | tta | cat | tgg | 624 |
| Ser | Ser | Gln | Ser | Leu | Val | His | Ser | Asn | Gly | Asn | Thr | Tyr | Leu | His | Trp | |
| | | 195 | | | | | 200 | | | | | 205 | | | | |
| tac | ctg | cag | aag | cca | ggc | cag | tct | cca | aag | ctc | ctg | atc | tac | aaa | gtt | 672 |
| Tyr | Leu | Gln | Lys | Pro | Gly | Gln | Ser | Pro | Lys | Leu | Leu | Ile | Tyr | Lys | Val | |
| 210 | | | | | 215 | | | | | 220 | | | | | | |
| tcc | aac | cga | ttt | tct | ggg | gtc | cca | gac | agg | ttc | agt | ggc | agt | gga | tca | 720 |
| Ser | Asn | Arg | Phe | Ser | Gly | Val | Pro | Asp | Arg | Phe | Ser | Gly | Ser | Gly | Ser | |
| 225 | | | | | 230 | | | | | 235 | | | | | 240 | |
| ggg | aca | gat | ttc | aca | ctc | aag | atc | agc | aga | gtg | gag | gct | gag | gat | ctg | 768 |
| Gly | Thr | Asp | Phe | Thr | Leu | Lys | Ile | Ser | Arg | Val | Glu | Ala | Glu | Asp | Leu | |
| | | | | 245 | | | | | 250 | | | | | 255 | | |
| gga | gtt | tat | ttc | tgc | tct | caa | agt | aca | cat | gtt | ccg | ctc | acg | ttc | ggt | 816 |
| Gly | Val | Tyr | Phe | Cys | Ser | Gln | Ser | Thr | His | Val | Pro | Leu | Thr | Phe | Gly | |
| | | | 260 | | | | | 265 | | | | | 270 | | | |
| gct | ggg | acc | aag | ctg | gag | ctg | aaa | gaa | ttc | ggt | ggc | gcg | ccg | gag | ttc | 864 |
| Ala | Gly | Thr | Lys | Leu | Glu | Leu | Lys | Glu | Phe | Gly | Gly | Ala | Pro | Glu | Phe | |
| | | 275 | | | | | 280 | | | | | 285 | | | | |
| ccg | aaa | ccg | tcc | acc | ccg | ccg | ggt | tct | tct | ggt | tta | gag | ggc | ggc | agc | 912 |
| Pro | Lys | Pro | Ser | Thr | Pro | Pro | Gly | Ser | Ser | Gly | Leu | Glu | Gly | Gly | Ser | |
| 290 | | | | | 295 | | | | | 300 | | | | | | |

```
ctg gcc gcg ctg acc gcg cac cag gct tgc cac ctg ccg ctg gag act     960
Leu Ala Ala Leu Thr Ala His Gln Ala Cys His Leu Pro Leu Glu Thr
305                 310                 315                 320 ttc acc cgt cat cgc cag ccg cgc ggc tgg gaa caa ctg gag cag tgc    1008
Phe Thr Arg His Arg Gln Pro Arg Gly Trp Glu Gln Leu Glu Gln Cys
                325                 330                 335 ggc tat ccg gtg cag cgg ctg gtc gcc ctc tac ctg gcg gcg cgg ctg    1056
Gly Tyr Pro Val Gln Arg Leu Val Ala Leu Tyr Leu Ala Ala Arg Leu
        340                 345                 350 tcg tgg aac cag gtc gac cag gtg atc cgc aac gcc ctg gcc agc ccc    1104
Ser Trp Asn Gln Val Asp Gln Val Ile Arg Asn Ala Leu Ala Ser Pro
            355                 360                 365 ggc agc ggc ggc gac ctg ggc gaa gcg atc cgc gag cag ccg gag cag    1152
Gly Ser Gly Gly Asp Leu Gly Glu Ala Ile Arg Glu Gln Pro Glu Gln
370                 375                 380 gcc cgt ctg gcc ctg acc ctg gcc gcc gcc gag agc gag cgc ttc gtc    1200
Ala Arg Leu Ala Leu Thr Leu Ala Ala Ala Glu Ser Glu Arg Phe Val
385                 390                 395                 400 cgg cag ggc acc ggc aac gac gag gcc ggc gcg gcc aac gcc gac gtg    1248
Arg Gln Gly Thr Gly Asn Asp Glu Ala Gly Ala Ala Asn Ala Asp Val
                405                 410                 415 gtg agc ctg acc tgc ccg gtc gcc gcc ggt gaa tgc gcg ggc ccg gcg    1296
Val Ser Leu Thr Cys Pro Val Ala Ala Gly Glu Cys Ala Gly Pro Ala
        420                 425                 430 gac agc ggc gac gcc ctg ctg gag cgc aac tat ccc act ggc gcg gag    1344
Asp Ser Gly Asp Ala Leu Leu Glu Arg Asn Tyr Pro Thr Gly Ala Glu
            435                 440                 445 ttc ctc ggc gac ggc ggc gac gtc agc ttc agc acc cgc ggc acg cag    1392
Phe Leu Gly Asp Gly Gly Asp Val Ser Phe Ser Thr Arg Gly Thr Gln
450                 455                 460 aac tgg acg gtg gag cgg ctg ctc cag gcg cac cgc caa ctg gag gag    1440
Asn Trp Thr Val Glu Arg Leu Leu Gln Ala His Arg Gln Leu Glu Glu
465                 470                 475                 480 cgc ggc tat gtg ttc gtc ggc tac cac ggc acc ttc ctc gaa gcg gcg    1488
Arg Gly Tyr Val Phe Val Gly Tyr His Gly Thr Phe Leu Glu Ala Ala
                485                 490                 495 caa agc atc gtc ttc ggc ggg gtg cgc gcg cgc agc cag gac ctc gac    1536
Gln Ser Ile Val Phe Gly Gly Val Arg Ala Arg Ser Gln Asp Leu Asp
        500                 505                 510 gcg atc tgg cgc ggt ttc tat atc gcc ggc gat ccg gcg ctg gcc tac    1584
Ala Ile Trp Arg Gly Phe Tyr Ile Ala Gly Asp Pro Ala Leu Ala Tyr
            515                 520                 525 ggc tac gcc cag gac cag gaa ccc gac gca cgc ggc cgg atc cgc aac    1632
Gly Tyr Ala Gln Asp Gln Glu Pro Asp Ala Arg Gly Arg Ile Arg Asn
530                 535                 540 ggt gcc ctg ctg cgg gtc tat gtg ccg cgc tcg agc ctg ccg ggc ttc    1680
Gly Ala Leu Leu Arg Val Tyr Val Pro Arg Ser Ser Leu Pro Gly Phe
545                 550                 555                 560 tac cgc acc agc ctg acc ctg gcc gcc ccg gag gcg gcg ggc gag gtc    1728
Tyr Arg Thr Ser Leu Thr Leu Ala Ala Pro Glu Ala Ala Gly Glu Val
                565                 570                 575 gaa cgg ctg atc ggc cat ccg ctg ccg ctg cgc ctg gac gcc atc acc    1776
Glu Arg Leu Ile Gly His Pro Leu Pro Leu Arg Leu Asp Ala Ile Thr
        580                 585                 590 ggc ccc gag gag gaa ggc ggg cgc ctg gag acc att ctc ggc tgg ccg    1824
Gly Pro Glu Glu Glu Gly Gly Arg Leu Glu Thr Ile Leu Gly Trp Pro
            595                 600                 605 ctg gcc gag cgc acc gtg gtg att ccc tcg gcg atc ccc acc gac ccg    1872
Leu Ala Glu Arg Thr Val Val Ile Pro Ser Ala Ile Pro Thr Asp Pro
610                 615                 620
```

```
cgc aac gtc ggc ggc gac ctc gac ccg tcc agc atc ccc gac aag gaa    1920
Arg Asn Val Gly Gly Asp Leu Asp Pro Ser Ser Ile Pro Asp Lys Glu
625             630             635             640 cag gcg atc agc gcc ctg ccg gac tac gcc agc cag ccc gga aaa ccg    1968
Gln Ala Ile Ser Ala Leu Pro Asp Tyr Ala Ser Gln Pro Gly Lys Pro
            645             650             655 ccg gac tac aag gat gac gac gat aag aaa gac gaa ctg tag tga        2013
Pro Asp Tyr Lys Asp Asp Asp Asp Lys Lys Asp Glu Leu
            660             665

<210> SEQ ID NO 102
<211> LENGTH: 669
<212> TYPE: PRT
<213> ORGANISM: Mus musculus

<400> SEQUENCE: 102

Met Lys Tyr Leu Leu Pro Thr Ala Ala Ala Gly Leu Leu Leu Leu Ala
1               5                   10                  15

Ala Gln Pro Ala Met Ala Met Asp His His His His His His His
            20                  25                  30

His His Lys Leu Gln Val Gln Leu Gln Gln Ser Gly Ala Glu Leu Ala
        35                  40                  45

Arg Pro Gly Ala Ser Val Lys Leu Ser Cys Lys Ala Ser Gly Tyr Thr
50                  55                  60

Phe Thr Ser Tyr Trp Met His Trp Val Lys Gln Arg Pro Gly Gln Gly
65                  70                  75                  80

Leu Glu Trp Ile Gly Ala Ile Tyr Pro Gly Asp Gly Asp Thr Arg Tyr
                85                  90                  95

Thr Gln Lys Phe Lys Gly Lys Ala Thr Leu Thr Ala Asp Lys Ser Ser
            100                 105                 110

Ser Thr Ala Tyr Met Gln Leu Ser Ser Leu Ala Ser Glu Asp Ser Ala
        115                 120                 125

Val Tyr Tyr Cys Ala Ser Gly Ile Thr Ala Val Ala Asp Tyr Trp Gly
    130                 135                 140

Gln Gly Thr Thr Leu Thr Val Ser Ser Gly Gly Gly Ser Gly Gly
145                 150                 155                 160

Gly Gly Ser Gly Gly Gly Ser Asp Val Val Met Thr Gln Thr Pro
                165                 170                 175

Leu Ser Leu Pro Val Ser Leu Gly Asp Gln Ala Ser Ile Ser Cys Arg
            180                 185                 190

Ser Ser Gln Ser Leu Val His Ser Asn Gly Asn Thr Tyr Leu His Trp
        195                 200                 205

Tyr Leu Gln Lys Pro Gly Gln Ser Pro Lys Leu Leu Ile Tyr Lys Val
    210                 215                 220

Ser Asn Arg Phe Ser Gly Val Pro Asp Arg Phe Ser Gly Ser Gly Ser
225                 230                 235                 240

Gly Thr Asp Phe Thr Leu Lys Ile Ser Arg Val Glu Ala Glu Asp Leu
                245                 250                 255

Gly Val Tyr Phe Cys Ser Gln Ser Thr His Val Pro Leu Thr Phe Gly
            260                 265                 270

Ala Gly Thr Lys Leu Glu Leu Lys Glu Phe Gly Gly Ala Pro Glu Phe
        275                 280                 285

Pro Lys Pro Ser Thr Pro Pro Gly Ser Ser Gly Leu Glu Gly Gly Ser
    290                 295                 300

Leu Ala Ala Leu Thr Ala His Gln Ala Cys His Leu Pro Leu Glu Thr
305                 310                 315                 320
```

-continued

```
Phe Thr Arg His Arg Gln Pro Arg Gly Trp Glu Gln Leu Glu Gln Cys
            325                 330                 335
Gly Tyr Pro Val Gln Arg Leu Val Ala Leu Tyr Leu Ala Ala Arg Leu
                340                 345                 350
Ser Trp Asn Gln Val Asp Gln Val Ile Arg Asn Ala Leu Ala Ser Pro
            355                 360                 365
Gly Ser Gly Gly Asp Leu Gly Glu Ala Ile Arg Glu Gln Pro Glu Gln
        370                 375                 380
Ala Arg Leu Ala Leu Thr Leu Ala Ala Ala Glu Ser Glu Arg Phe Val
385                 390                 395                 400
Arg Gln Gly Thr Gly Asn Asp Glu Ala Gly Ala Ala Asn Ala Asp Val
                405                 410                 415
Val Ser Leu Thr Cys Pro Val Ala Ala Gly Glu Cys Ala Gly Pro Ala
                420                 425                 430
Asp Ser Gly Asp Ala Leu Leu Glu Arg Asn Tyr Pro Thr Gly Ala Glu
        435                 440                 445
Phe Leu Gly Asp Gly Gly Asp Val Ser Phe Ser Thr Arg Gly Thr Gln
    450                 455                 460
Asn Trp Thr Val Glu Arg Leu Leu Gln Ala His Arg Gln Leu Glu Glu
465                 470                 475                 480
Arg Gly Tyr Val Phe Val Gly Tyr His Gly Thr Phe Leu Glu Ala Ala
                485                 490                 495
Gln Ser Ile Val Phe Gly Gly Val Arg Ala Arg Ser Gln Asp Leu Asp
                500                 505                 510
Ala Ile Trp Arg Gly Phe Tyr Ile Ala Gly Asp Pro Ala Leu Ala Tyr
            515                 520                 525
Gly Tyr Ala Gln Asp Gln Glu Pro Asp Ala Arg Gly Arg Ile Arg Asn
        530                 535                 540
Gly Ala Leu Leu Arg Val Tyr Val Pro Arg Ser Ser Leu Pro Gly Phe
545                 550                 555                 560
Tyr Arg Thr Ser Leu Thr Leu Ala Ala Pro Glu Ala Ala Gly Glu Val
                565                 570                 575
Glu Arg Leu Ile Gly His Pro Leu Pro Leu Arg Leu Asp Ala Ile Thr
                580                 585                 590
Gly Pro Glu Glu Glu Gly Gly Arg Leu Glu Thr Ile Leu Gly Trp Pro
            595                 600                 605
Leu Ala Glu Arg Thr Val Val Ile Pro Ser Ala Ile Pro Thr Asp Pro
610                 615                 620
Arg Asn Val Gly Gly Asp Leu Asp Pro Ser Ser Ile Pro Asp Lys Glu
625                 630                 635                 640
Gln Ala Ile Ser Ala Leu Pro Asp Tyr Ala Ser Gln Pro Gly Lys Pro
                645                 650                 655
Pro Asp Tyr Lys Asp Asp Asp Asp Lys Lys Asp Glu Leu
            660                 665
```

PHARMACEUTICAL COMPOSITION COMPRISING ANTI-GRP78 ANTIBODY AS ACTIVE INGREDIENT

CROSS-REFERENCE TO RELATED APPLICATIONS

This application is a National Stage application of PCT/JP2008/053898, filed Feb. 27, 2008, which claims priority from Japanese application JP 2007-047534, filed Feb. 27, 2007.

TECHNICAL FIELD

The present invention relates to a method of treating cancer treatment and anticancer agents.

BACKGROUND ART

GRP proteins (glucose-regulated proteins) are molecular chaperones localized to endoplasmic reticulum (ER). They are known as members of a protein family that is induced in response to various intrinsic or extrinsic ER stresses, such as glucose starvation, or accumulation of misfolded proteins in ER (Non-patent document 1).

GRP78 is one of GRP proteins with a molecular weight of 78 kDa and is also well known as BiP (immunoglobulin binding protein). Overexpression, or antisense approaches directly showed that GRP78 is involved in protective role from cell death caused by ER stress (Non-patent document 1).

Solid tumor cells in vivo are constantly exposed in ER stress, including glucose deprivation, hypoxia and low pH, due to a feature of the tumor microenvironment. As if to support this understanding, increased expression of GRP78 protein has been confirmed in a variety of cancer cell lines or clinical cancer specimens, correlating with malignancy (Non-patent documents 2 to 5). Further, it has been demonstrated that an overexpression of GRP78 protein is involved in the acquisition of resistance to therapeutic treatment of anti-cancer drugs generated by topoisomerase inhibitory activity or antiangiogenesis agents (Non-patent documents 6 and 7). In a clinical study, a group of breast cancer patients with enhanced expression of GRP78 were demonstrated to be less responsive to adriamycin-based chemotherapy than a group with lower expression of GRP78 (Non-patent document 8).

These reports suggest that up-regulation of GRP78 expression in tumor is associated with the mechanisms of survival, malignant transformation, resistance to anticancer agents (Non-patent document 1).

GRP78 is a molecular chaperone localized in ER, whereas translocation of this molecule on the cancer cell membrane has been reported. Furthermore, the possibility of application for cancer therapy by targeting the surface-located GRP78 has been indicated by several groups, with entirely different approach.

When the rabdomisarcoma cell line TE 671/RD was treated with thapsigargin (Tg), the cell membrane was slightly stained with an anti-GRP78 antibody, as confirmed by FACS analysis, thus demonstrating cell membrane localization of the GRP78 (Non-patent document 9).

It should be noted here that this report addresses a transient event during the induction of cell death by Tg treatment and that it does not show data for a persistent change in GRP78 localization in cancer cells. In addition, since the antibody used in the report is a commercially available goat-derived polyclonal antibody, its whose epitope is unknown.

Later, another research group reported that the two GRP78 binding peptides (WIFPWIQL (SEQ ID NO: 103) and WDLAWMFRLPVG (SEQ ID NO: 104)) which acquired by phage binding assays could bind to the cell surface of the prostate cancer cell line DU145 and being internalized into the cells (Non-patent document 10).

In addition, those GRP78 binding peptides fused to the cell death-inducing motif $(KLAKLAK)_2$ (SEQ ID NO: 105) (Non-patent document 11) have shown not only the induction of cell death on DU145 cells in vitro but also antitumor effects in an experiment on mouse transplant models (Non-patent document 10).

Another research group reported that the surface-located GRP78 protein on vascular endothelial cells serves as a receptor for angiogenesis inhibitor Kringle 5 (K5) (Non-patent document 16). They further demonstrated that interaction of GRP78 with a recombinant K5 induces not only an inhibition of angiogenesis but also cell death on various cancer cell lines cultured under hypoxia (Non-patent document 16).

Thus, the series of experiments described above have shown that peptides that bind to the surface-located GRP78 on cancer cells or vascular endothelial cells might be a useful tool as antitumor agents. However, it would be difficult to apply them in the development for clinical application since the site of the surface-located GRP78 protein recognized by these peptides is not known in the art.

Aside from those findings, two entirely unrelated groups relied upon different approaches to report localization of GRP78 on the cell membrane.

One group showed that the receptor of the activated forms of $\alpha_2$-macroglobulin ($\alpha_2M^*$), which functioned as a growth factor in a prostate cancer cell line (1-LN) (Non-patent document 12), was GRP78 (Non-patent document 13). The discovery added a new finding that the GRP78 protein long considered to be an ER protein also functions as a receptor of the growth factor on the cell membrane.

The other group studied that polyclonal antibody in the serum from prostate cancer patient recognize the peptide sequence "CNVSDKSC" (SEQ ID NO: 106) (i.e., anti-CNVSDKSC (SEQ ID NO: 106) antibody); they then identified that a target protein recognized by this antibody was the GRP78 protein (Non-patent document 14). Although the anti-CNVSDKSC (SEQ ID NO: 106) antibody bound to cell surface, there were no matched or similar sequence "CNVSDKSC" (SEQ ID NO: 106) within GRP78 sequence, suggesting that primary amino acid sequence "CNVSDKSC" (SEQ ID NO: 106) contains a tertiary structural motif mimicking an epitope in surface-located GRP78. However, it was not identified the site of GRP78 which were recognized by this antibody.

Later in time, another group performed a tertiary structural analysis of the peptide "CNVSDKSC" (SEQ ID NO: 106) and identified the GRP78 primary amino acid sequence "LIGRTWNDPSVQQDIKFL" (SEQ ID NO: 107) located at $Leu^{98}$-$Leu^{115}$ which forms the similar tertiary structure serving as a putative binding site. They then prepared a rabbit polyclonal antibody against this sequence and eventually confirmed that the antibody could stain the cell surface of cancer cells, i.e., the prostate cancer cell lines 1-LN and DU145 as well as the melanoma cell line DM413. It was also confirmed that the antibody, when added to the prostate cancer cell lines, had an ability to increase the intracellular calcium concentration, induce cell proliferation, and protect the cell from apoptosis induced by TNF-$\alpha$., as observed upon addition of $\alpha_2M^*$ (Non-patent document 15). Since the antibody against GRP78 thusly mimicked the ligand activity of α$_2$M*, it was revealed that the region Leu$^{98}$-Leu$^{115}$ of GRP78 was an α$_2$M*binding sequence (Non-patent document 15).

This report validated that GRP78 is localized to cell surface in prostate cancer and it was further revealed that Leu$^{98}$-Leu$^{115}$ of GRP78 (LIGRTWNDPSVQQDIKFL) (SEQ ID NO: 107) was exposed extracellularly as an α$_2$M* binding sequence.

Further, from another approach, it was reported that antibodies against the 98-115 region of GRP78 stained the cell surface of cancer cells, thus revealing that this region would be capable of serving as an extracellular epitope of GRP78.

Thus it was found that the GRP78 protein is highly expressed in many cancer types, with a localization change on the cell membrane. However it has been difficult to develop a new therapeutic antibody targeted to the surface-located GRP78 on the basis of findings as below. First, the site of the GRP78 exposed on the cell surface, which were recognized by the above-described GRP78 binding peptides is not clarified, rendering it impossible to prepare antibodies that provide similar effects to the peptides; indeed, no monoclonal antibody which functionally mimic those peptides exists. Second, the antibody which recognizes the 98-115 region of GRP78 can bind to the surface-located GRP78 of cancer cells but, at the same time, it mimics the α$_2$M* growth promoting action, so this antibody cannot be expected to display an antitumor activity.

Hence, it has been considered difficult to exert antitumor activity by means of the GRP78 binding antibody.

Non-patent document 1: Lee A S. Trends Biochem Sci. 2001, 26, 504-10

Non-patent document 2: Patierno, et al. 1998, Cancer Res. 47, 6220-24

Non-patent document 3: Bini et al. 1997, Electrophoresis. 18, 2832-41

Non-patent document 4: Gazit et al. 1999, Breast Cancer Res. Treat. 54, 135-46

Non-patent document 5: Fernandez et al. 2000, Breast Cancer Res. Treat. 59, 15-26

Non-patent document 6: Reddy et al, J. Bio. Chem. 2003, 278, 20915-24

Non-patent document 7: Dong et al, 2005, Cancer Res. 65, 5785-5791

Non-patent document 8: Lee et al. 2006, Cancer Res. 66, 7849-7853

Non-patent document 9: Delpino et al. 1998, Molecular Membrane Biology, 15, 21-26

Non-patent document 10: Arap et al. 2004, CANCER CELL. 6, 275-284

Non-patent document 11: Javadpour et al. 1996, J. Med. Chem. 39, 3107-3113

Non-patent document 12: Asplin et al. 2000, Archives of Biochemistry and Biophysics. 383, 135-141

Non-patent document 13: Misra et al. 2002, J. Biol. Chem. 277, 42082-42087

Non-patent document 14: Mintz et al. 2003, Nat. Biotech. 21, 57-63

Non-patent document 15: Gonzalez-Gronow et al. 2006, Cancer Res. 66, 11424-11431

Non-patent document 16: Davidoson et al., 2005, Cancer Res. 65, 4663-4672

DISCLOSURE OF THE INVENTION

Problems to be Solved by the Invention

An object of the present invention is to provide novel pharmaceutical compositions using anti-GRP78 antibodies. More particularly, the present invention aims to provide a novel method of cancer treatment using anti-GRP78 antibodies, a novel cell growth suppressing agent and an anticancer agent that contain anti-GRP78 antibodies, as well as novel anti-GRP78 antibodies.

Means for Solving the Problems

The present inventor attempted to prepare antitumor antibodies against cancer specific surface-located GRP78. To this end, it was first necessary to identify an amino acid that would be capable of serving as an epitope for the antibody exposed on the cell surface of cancer cells. So, the present inventor purified the GRP78 protein, immunized mice with the purified GRP78 protein, and selected only anti-GRP78 antibodies that stained the cell surface of cancer cells. As a result, the inventor successfully obtained an anti-GRP78 antibody that would bind specifically to the cell surface of cancer cells. Subsequently, the inventor attempted to identify the sequence that would be recognized by the obtained antibody. The analysis revealed that the antibody specifically recognized the 40 amino acids region of the 376-415 region of GRP78. It was thus revealed that the 376-415 amino acid region of GRP78 was exposed extracellularly. The inventor then confirmed that the antibody recognizing this epitope was able to be internalized into the cells rapidly. Next, based on this antibody, the inventor prepared a scFv antibody attached a toxin and analyzed an in vitro cytotoxic activity in cancer cell lines; as a result, it was revealed that the obtained toxin-labeled scFv antibody specifically killed cancer cells. Further, the inventor analyzed the antitumor activity of the antibody in a xenograft mouse models bearing cancer cell line. The transplanted tumor volume could be significantly reduced in mice treated with the antibody. These results confirmed that the antibody could exhibit the antitumor activity not only in vitro but also in vivo. These findings revealed that the antibody against an extracellular region of GRP78 was useful as an antitumor agent.

Based on these findings, the inventor of the present invention has revealed to be able to solve the aforementioned problems.

Specifically, the present invention provides the embodiments described in the following (1) to (28).

(1) A pharmaceutical composition containing an antibody that binds to a glucose-regulated protein 78 (GRP78).

(2) The composition according to (1) which is an anticancer agent.

(3) The composition according to (1) or (2), wherein the antibody is a monoclonal antibody.

(4) The composition according to any one of (1) to (3), wherein the antibody binds to GRP78 localized on cell surfaces.

(5) The composition according to any one of (1) to (4), wherein the antibody is internalized into cells expressing GRP78.

(6) The composition according to any one of (1) to (5), wherein the antibody binds to the epitope depicted in SEQ ID NO: 3.

(7) The composition according to any one of (1) to (6), wherein the antibody is conjugated with a cytotoxic substance.

(8) A monoclonal antibody that binds to GRP78.

(9) The antibody according to (8) which binds to GRP78 expressed on cell surfaces.

(10) The antibody according to (8) or (9) which is internalized into cells expressing GRP78.

(11) The antibody according to any one of (8) to (10) which binds to the epitope depicted in SEQ ID NO: 3.

(12) The antibody according to any one of (8) to (11) which recognizes the same epitope as the one that is recognized by an antibody selected from among the following (a) to (f):

(a) an antibody comprising a heavy-chain variable region and a light-chain variable region, the heavy-chain variable region having the amino acid sequence depicted in SEQ ID NO: 8 as CDR1, the amino acid sequence depicted in SEQ ID NO: 9 as CDR2, and the amino acid sequence depicted in SEQ ID NO: 10 as CDR3, and the light-chain variable region having the amino acid sequence depicted in SEQ ID NO: 11 as CDR1, the amino acid sequence depicted in SEQ ID NO: 12 as CDR2, and the amino acid sequence depicted in SEQ ID NO: 13 as CDR3;

(b) an antibody comprising a heavy-chain variable region and a light-chain variable region, the heavy-chain variable region having the amino acid sequence depicted in SEQ ID NO: 18 as CDR1, the amino acid sequence depicted in SEQ ID NO: 19 as CDR2, and the amino acid sequence depicted in SEQ ID NO: 20 as CDR3, and the light-chain variable region having the amino acid sequence depicted in SEQ ID NO: 21 as CDR1, the amino acid sequence depicted in SEQ ID NO: 22 as CDR2, and the amino acid sequence depicted in SEQ ID NO: 23 as CDR3;

(c) an antibody comprising a heavy-chain variable region and a light-chain variable region, the heavy-chain variable region having the amino acid sequence depicted in SEQ ID NO: 61 as CDR1, the amino acid sequence depicted in SEQ ID NO: 62 as CDR2, and the amino acid sequence depicted in SEQ ID NO: 63 as CDR3, and the light-chain variable region having the amino acid sequence depicted in SEQ ID NO: 64 as CDR1, the amino acid sequence depicted in SEQ ID NO: 65 as CDR2, and the amino acid sequence depicted in SEQ ID NO: 66 as CDR3;

(d) an antibody comprising a heavy-chain variable region and a light-chain variable region, the heavy-chain variable region having the amino acid sequence depicted in SEQ ID NO: 71 as CDR1, the amino acid sequence depicted in SEQ ID NO: 72 as CDR2, and the amino acid sequence depicted in SEQ ID NO: 73 as CDR3, and the light-chain variable region having the amino acid sequence depicted in SEQ ID NO: 74 as CDR1, the amino acid sequence depicted in SEQ ID NO: 75 as CDR2, and the amino acid sequence depicted in SEQ ID NO: 76 as CDR3;

(e) an antibody comprising a heavy-chain variable region and a light-chain variable region, the heavy-chain variable region having the amino acid sequence depicted in SEQ ID NO: 81 as CDR1, the amino acid sequence depicted in SEQ ID NO: 82 as CDR2, and the amino acid sequence depicted in SEQ ID NO: 83 as CDR3, and the light-chain variable region having the amino acid sequence depicted in SEQ ID NO: 84 as CDR1, the amino acid sequence depicted in SEQ ID NO: 85 as CDR2, and the amino acid sequence depicted in SEQ ID NO: 86 as CDR3; and (f) an antibody comprising a heavy-chain variable region and a light-chain variable region, the heavy-chain variable region having the amino acid sequence depicted in SEQ ID NO: 91 as CDR1, the amino acid sequence depicted in SEQ ID NO: 92 as CDR2, and the amino acid sequence depicted in SEQ ID NO: 93 as CDR3, and the light-chain variable region having the amino acid sequence depicted in SEQ ID NO: 94 as CDR1, the amino acid sequence depicted in SEQ ID NO: 95 as CDR2, and the amino acid sequence depicted in SEQ ID NO: 96 as CDR3.

(13) The antibody according to any one of (8) to (12) which has cytotoxic activity against cells expressing GRP78.

(14) The antibody according to (13) which is conjugated with a cytotoxic substance.

(15) A method of delivering a cytotoxic substance into cells using an anti-GRP78 antibody.

(16) A method of suppressing the growth of cells by means of a cytotoxic substance conjugated with an anti-GRP78 antibody.

(17) The method according to (15) or (16), wherein the cells are cancer cells.

(18) Use of an anti-GRP78 antibody for delivering a cytotoxic substance into cells.

(19) Use of an anti-GRP78 antibody having an internalizing activity for suppressing the growth of cells.

(20) The use according to (18) or (19), wherein the cells are cancer cells.

(21) The use according to any one of (18) to (20), wherein the cytotoxic substance is conjugated with the anti-GRP78 antibody.

(22) A process for producing a pharmaceutical composition comprising the following steps:
 (a) the step of providing GRP78 antibodies;
 (b) the step of validating whether the antibodies of (a) have an internalizing activity;
 (c) the step of selecting antibodies having an internalizing activity; and
 (d) the step of binding a cytotoxic substance to the antibodies selected in (c).

(23) The process according to (22), wherein the pharmaceutical composition is an anticancer agent.

(24) A method of diagnosing a cancer using an anti-GRP78 antibody.

(25) The method of diagnosing according to (24) which uses an anti-GRP antibody conjugated with a labeling substance.

(26) The method of diagnosis according to (24) or (25) which detects the anti-GRP78 antibody incorporated into cells. An anti-GRP78 antibody conjugated with a labeling substance.

(27) A polypeptide comprising the amino acid sequence of SEQ ID NO: 3 or a fragment thereof.

(28) A polypeptide comprising the amino acid sequence of SEQ ID NO: 3 or a fragment thereof.

ADVANTAGES OF THE INVENTION

The present invention shows that by providing novel antibodies that have an activity of GRP78 binding and internalization into target cells, novel pharmaceutical compositions can be provided that can be used to treat various tumors or cancers that have GRP78 exposed on the cell surface. In addition, by using antibodies having such characteristics, a method of diagnosing various tumors or cancers can be provided.

BEST MODE FOR CARRYING OUT THE INVENTION

Figure 1:
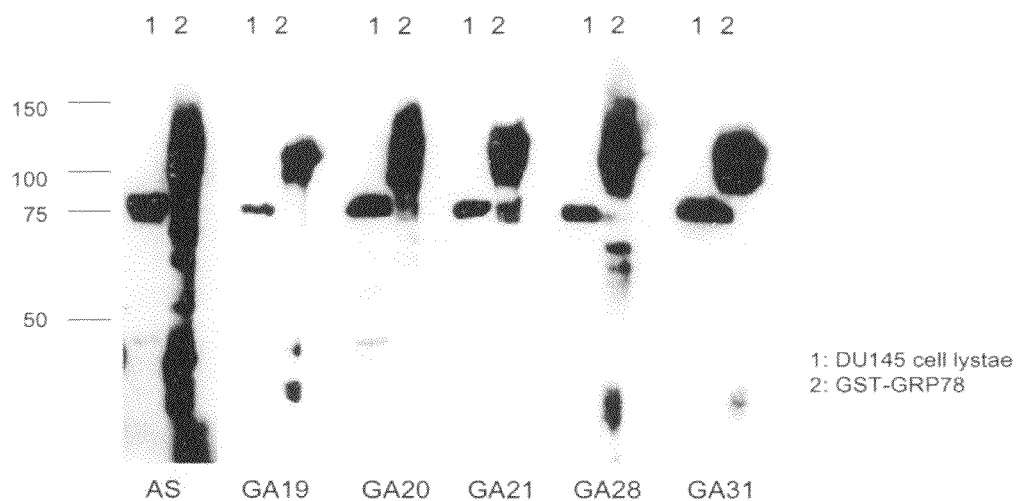
FIG. 1 is a diagram showing the results of western blot analysis of the GRP78 binding activities of the obtained antibodies; a cell lysate sample prepared from DU145 cells was loaded in lane 1, and GST fused GRP78 protein purified from *E. Coli* was loaded in lane 2, followed by staining with each antibody; AS (antiserum) is a mouse antiserum collected before cell fusion.

The anti-GRP78 antibody of the present invention may be of any type that binds to the GRP78 protein (SEQ ID NO: 2) and it is by no means limited in such aspects as the origin (mouse, rat, human, etc.), type (monoclonal antibody or polyclonal antibody), and shape (altered antibody, small molecular antibody, modified antibody, etc.)

The anti-GRP78 antibody to be used in the present invention preferably specifically binds to GRP78. It is also preferred that the anti-GRP78 antibody to be used in the present invention is a monoclonal antibody.

GRP78 is known to be localized on the plasma membrane of cancer cells and the like. One preferred embodiment of the anti-GRP78 antibody to be used in the present invention may be an antibody that recognizes the region of GRP78 that is exposed extracellularly when it is localized on the cell membrane.

Such antibody can be acquired by, for example, preparing antibodies using the GRP78 protein (SEQ ID NO: 2) as an immunogen and selecting from among the prepared antibodies those which can bind to cancer cells expressing GRP78 on the cell membrane (e.g. prostate cancer cell line DU145). More specifically, the method described in the Examples may typically be employed to acquire an antibody that recognizes the region of GRP78 that is exposed extracellularly when it is localized on the cell membrane.

In the present invention, the region of GRP78 that is exposed extracellularly when it is localized on the cell membrane is preferably such that when the antibody binds to that region, it will not mimic the growth promoting action of $\alpha_2$ macroglobulin and a particularly preferred region is other than the $98^{th}$ to $115^{th}$ region of GRP78.

Preferred examples of the region of GRP78 that is exposed extracellularly when it is localized on the cell membrane include that region of the amino acid sequence depicted by SEQ ID NO: 2 which is between the $376^{th}$ and the $415^{th}$ position (SEQ ID NO: 3). Therefore, preferred examples of an antibody that recognizes the region of GRP78 that is exposed extracellularly when it is localized on the cell membrane include those antibodies that recognize the $376^{th}$ to $415^{th}$ region of GRP78. Examples of the antibody that recognizes the $376^{th}$ to $415^{th}$ amino acids in the protein GRP78 are not particularly limited and include an antibody that recognizes the $384^{th}$ to $391^{st}$ amino acids (i.e., amino acids 9-16 in SEQ ID NO: 3), an antibody that recognizes the $392^{nd}$ to $407^{th}$ amino acids (i.e., amino acids 17-32 in SEQ ID NO: 3), and an antibody that recognizes the $400^{th}$ to $415^{th}$ amino acids (i.e., amino acids 25-40 in SEQ ID NO: 3). Whether a particular antibody recognizes the intended epitope can be confirmed by methods known to skilled artisans, for example, by the method described in the Examples.

Other preferred embodiments of the antibody to be used in the present invention include antibodies having an internalizing activity. In the present invention, the "antibodies having an internalizing activity" means those antibodies which will be transported into cells (e.g., into the cytoplasm, vesicles or other organelles) after binding to GRP78 localized on the cell surface.

Whether a particular antibody has an internalizing activity can be confirmed by methods known to skilled artisans, for example, a method in which an anti-GRP78 antibody conjugated with a labeling substance is brought into contact with cells expressing GRP78 (e.g. prostate cancer cell line DU145) and a check is made to see if the labeling substance has been incorporated into the cells, and a method in which an anti-GRP78 antibody conjugated with a cytotoxic substance is brought into contact with cells expressing GRP78 and a check is made to see if cell death has been induced in those GRP78 expressing cells. More specifically, the method described in the Examples may typically be employed to check to see if a particular antibody has an internalizing activity.

In the present invention, particularly preferred antibodies include one that recognizes the region of GRP78 that is exposed extracellularly when it is localized on the cell membrane and which has an internalizing activity. Such antibodies can be acquired by first employing the above-exemplified method to select those antibodies which recognize the region of GRP78 that is exposed extracellularly when it is localized on the cell membrane and subsequently further selecting from the thus selected antibodies those which have an internalizing activity.

Examples of the preferred antibodies that may be used in the present invention include the following antibodies (a) to (s).

(a) An antibody comprising a heavy-chain variable region having the amino acid sequence of SEQ ID NO: 8 as CDR1, the amino acid sequence of SEQ ID NO:9 as CDR2, and the amino acid sequence of SEQ ID NO: 10 as CDR3.

(b) An antibody comprising a light-chain variable region having the amino acid sequence of SEQ ID NO: 11 as CDR1, the amino acid sequence of SEQ ID NO: 12 as CDR2, and the amino acid sequence of SEQ ID NO: 13 as CDR3;

(c) An antibody comprising the heavy-chain variable region of (a) and the light-chain variable region of (b).

(d) An antibody comprising a heavy-chain variable region having the amino acid sequence of SEQ ID NO: 18 as CDR1, the amino acid sequence of SEQ ID NO: 19 as CDR2, and the amino acid sequence of SEQ ID NO: 20 as CDR3.

(e) An antibody comprising a light-chain variable region having the amino acid sequence of SEQ ID NO: 21 as CDR1, the amino acid sequence of SEQ ID NO: 22 as CDR2, and the amino acid sequence of SEQ ID NO: 23 as CDR3.

(f) An antibody comprising the heavy-chain variable region of (d) and the light-chain variable region of (e).

(g) An antibody comprising a heavy-chain variable region having the amino acid sequence of SEQ ID NO: 61 as CDR1, the amino acid sequence of SEQ ID NO: 62 as CDR2, and the amino acid sequence of SEQ ID NO: 63 as CDR3.

(h) An antibody containing a light-chain variable region comprising the amino acid sequence of SEQ ID NO: 64 as CDR1, the amino acid sequence of SEQ ID NO: 65 as CDR2, and the amino acid sequence of SEQ ID NO: 66 as CDR3.

(i) An antibody comprising the heavy-chain variable region of (g) and the light-chain variable region of (h).

(j) An antibody comprising a heavy-chain variable region having the amino acid sequence of SEQ ID NO: 71 as CDR1, the amino acid sequence of SEQ ID NO: 72 as CDR2, and the amino acid sequence of SEQ ID NO: 73 as CDR3.

(k) An antibody comprising a light-chain variable region having the amino acid sequence of SEQ ID NO: 74 as CDR1, the amino acid sequence of SEQ ID NO: 75 as CDR2, and the amino acid sequence of SEQ ID NO: 76 as CDR3.

(l) An antibody comprising the heavy-chain variable region of (j) and the light-chain variable region of (k).

(m) An antibody comprising a heavy-chain variable region having the amino acid sequence of SEQ ID NO: 81 as CDR1, the amino acid sequence of SEQ ID NO: 82 as CDR2, and the amino acid sequence of SEQ ID NO: 83 as CDR3.

(n) An antibody comprising a light-chain variable region having the amino acid sequence of SEQ ID NO: 84 as CDR1, the amino acid sequence of SEQ ID NO: 85 as CDR2, and the amino acid sequence of SEQ ID NO: 86 as CDR3.

(o) An antibody comprising the heavy-chain variable region of (m) and the light-chain variable region of (n).

(p) An antibody comprising a heavy-chain variable region having the amino acid sequence of SEQ ID NO: 91 as CDR1, the amino acid sequence of SEQ ID NO: 92 as CDR2, and the amino acid sequence of SEQ ID NO: 93 as CDR3.

(q) An antibody comprising a light-chain variable region having the amino acid sequence of SEQ ID NO: 94 as CDR1, the amino acid sequence of SEQ ID NO: 95 as CDR2, and the amino acid sequence of SEQ ID NO: 96 as CDR3.

(r) An antibody comprising the heavy-chain variable region of (p) and the light-chain variable region of (q).

(s) An antibody recognizing the same epitope as what is recognized by either one of the antibodies (a) to (r).

An antibody that recognizes the same epitope as a particular antibody may be obtained by the following procedure.

A subject antibody can be confirmed to share the same epitope with a particular antibody by examining the competition between the two antibodies for the same epitope. Competition between the two antibodies is detected by cross-blocking assay or the like. For example, competitive ELISA assay is a preferred example of the cross-blocking assay. Specifically, in cross-blocking assay, the GRP78 protein coated on the surface of wells in a microtiter plate is preincubated in the presence or absence of a candidate competing antibody and then the anti-GRP78 antibody of the present invention is added. The amount of the anti-GRP78 antibody of the present invention that binds to the GRP78 protein within the wells correlates indirectly to the binding ability of the candidate competing antibody (subject antibody) that competes for binding to the same epitope. In other words, the greater the affinity of the subject antibody for the same epitope, the smaller the amount of the anti-GRP78 antibody of the present invention that binds to the wells coated with the GRP78 protein and the greater the amount of the subject antibody that binds to the wells coated with the GRP78 protein.

The amount of the antibody that has bound to the wells can be easily measured by preliminary labeling of the antibody. For example, biotin-labeled antibodies can be measured by using an avidin-peroxidase conjugate and a suitable substrate. A cross-blocking assay that utilizes an enzyme label such as peroxidase is especially referred to competitive ELISA assay. Antibodies can be labeled with other labeling substances that are detectable or measurable. Specifically, a radioactive label or a fluorescent label and the like are known.

Furthermore, if the subject antibody has a constant region derived from a different species than the anti-GRP78 antibody of the present invention, the amount of the antibody that has bound to the wells can also be measured by a labeled antibody that recognizes the constant region of that antibody. Alternatively, the subject antibody may be derived from the same species as the anti-GRP78 antibody of the present invention but belongs to a different class; in this case, the amount of the antibody that has bound to the wells can be measured by an antibody that distinguishes between respective classes.

If, compared to the binding activity obtained in a control test conducted in its absence, the candidate competing antibody can block the binding of the anti-GRP78 antibody by at least 20%, preferably at least 20-50%, more preferably at least 50%, that candidate competing antibody is either an antibody that binds to substantially the same epitope as the anti-GRP78 antibody of the present invention or an antibody that competes for the binding to the same epitope.

An antibody that is conjugated with a cytotoxic substance may be mentioned as another preferred embodiment of the antibody to be used in the present invention. When the antibody that is conjugated with a cytotoxic substance is incorporated into cells, the cytotoxic substance is capable of inducing a killing action or cell death in the cells that have incorporated that antibody. Therefore, it is preferred that the antibody conjugated with a cytotoxic substance further has an internalizing activity.

Preferred embodiments of the anti-GRP78 antibody that is conjugated with a cytotoxic substance according to the present invention include, for example, antibodies that have a cytotoxic activity or induce cell death on GRP78 expressing cancer cells (e.g. DU145, 22Rv1, and MCF7).

The cytotoxic substance to be used in the present invention may be any substance that can induce a killing action or cell death in cells and it may be exemplified by toxins, radioactive substances, chemotherapeutics and the like. These cytotoxic substances to be used in the present invention include prodrugs that will be transformed to active cytotoxic substances in the living body. Activation of prodrugs may be generated through enzymatic or non-enzymatic transformation.

The term "toxins" as used herein means various proteins, polypeptides and the like that show cytotoxicity as derived from microorganisms, animals or plants. Toxins to be used in the present invention may include the following: Diphtheria toxin A chain (Langone J. J., et al., Methods in Enzymology, 93, 307-308, 1983); *Pseudomonas* exotoxin (Nature Medicine, 2, 350-353, 1996); Ricin A chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Gheeite V., et al., J. Immunol. Methods, 142, 223-230, 1991); Deglicosylated ricin A chain (Thorpe P. E., et al., Cancer Res., 47, 5924-5931, 1987); Abrin A chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; Thorpe P. E., et al., Cancer Res., 47, 5924-5931, 1987); Gelonin (Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Bolognesi A., et al., Clin. Exp. Immunol., 89, 341-346, 1992); PAP-s or pokeweed anti-viral protein from seeds (Bolognesi A., et al., Clin. Ekp. Immunol., 89, 341-346, 1992); Briodin (Bolognesi A., et al., Clin. Exp. Immunol., 89, 341-346, 1992); Saporin (Bolognesi A., et al., Clin. Exp. Immunol., 89, 341-346, 1992); Momordin (Cumber A. J., et al., J. Immunol. Methods, 135, 15-24, 1990; Wawrzynczak E. J., et al., Cancer Res., 50, 7519-7562, 1990; Bolognesi A., et al., Clin. Exp. Immunol., 89, 341-346, 1992); Momorcochin (Bolognesi A., et al., Clin. Exp. Immunol., 89, 341-346, 1992); Dianthin 32 (Bolognesi A., et al., Clin. Exp. Immunol., 89, 341-346, 1992); Dianthin 30 (Stirpe F., Barbieri L., FEBS letter 195, 1-8, 1986); Modeccin (Stirpe F., Barbieri L., FEBS letter 195, 1-8, 1986); Viscumin (Stirpe F., Barbieri L., FEBS letter 195, 1-8, 1986); Volkesin (Stirpe F., Barbieri L., FEBS letter 195, 1-8, 1986); Dodecandrin (Stirpe F., Barbieri L., FEBS letter 195, 1-8, 1986); Tritin (Stirpe F., Barbieri L., FEBS letter 195, 1-8, 1986); Luffin (Stirpe F., Barbieri L., FEBS letter 95, 1-8, 1986); Trichokirin (Casellas P., et al., Eur. J. Biochem. 176, 581-588, 1988; Bolognesi A., et al., Clin. Exp. Immunol., 89, 341-346, 1992).

The term "radioactive substances" as used herein refers to those substances that contain radioisotopes. Radioisotopes are not particularly limited and any radioisotopes may be used; examples that can be used include $^{32}P$, $^{14}C$, $^{125}I$, $^{3}H$, $^{131}I$, $^{186}Re$, $^{188}Re$, etc.

The term "chemotherapeutics" as used herein means those substances other than the above-mentioned toxins and radioactive substances which have cytotoxic activity and it encompasses cytokines, antitumor agents, enzymes, etc. The chemotherapeutics that can be used in the present invention are not particularly limited and those of lower molecular weights are preferred. With lower molecular weights, the chemotherapeutics would be less likely to interfere with the function of the antibody even after they bind to it. In the present invention, the chemotherapeutics of lower molecular weights generally have molecular weights of 100-2000, preferably 200-1000. Although not particularly limited, the chemotherapeutics that can be used in the present invention include the following: Melphalan (Rowland G. F., et al., Nature 255, 487-488, 1975); Cis-platinum (Hurwitz E. and Haimovich J., Methods In Enzymology 178, 369-375, 1986; Schechter B., et al., Int. J. Cancer 48, 167-172, 1991); Carboplatin (Ota, Y., et al., Asia-Oceania J. Obstet. Gynaecol. 19, 449-457, 1993); Mitomycin C (Noguchi, A., et al., Bioconjugate Chem. 3, 132-137, 1992); Adriamycin (Doxorubicin) (Shih, L. B., et al., Cancer Res. 51 4192-4198, 1991; Zhu, Z., et al., Cancer Immunol. Immumother 40, 257-267, 1995; Trail, P. A., et al., Science 261, 212-215, 1993; Kondo, Y., et al., Jpn. J. Cancer Res. 86, 1072-1079, 1995); Daunorubicin (Dillman, R. O., et al., Cancer Res. 48, 6097-6102, 1988; Hudecz, F., et al., Bioconjugate Chem. 1, 197-204, 1990; Tukada Y. et al., J. Natl. Cancer Inst. 75, 721-729, 1984); Bleomycin (Manabe, Y., et al., Biochem. Biophys. Res. Commun. 115, 1009-1014, 1983); Neocarzinostatin (Kitamura K., et al., Cancer Immunol. Immumother 36, 177-184, 1993; Yamaguchi T., et al., Jpn. J. Cancer Res. 85, 167-171, 1994); Methotrexate (Kralovec, J., et al., Cancer Immunol. Immumother 29, 293-302, 1989; Kulkarni, P. N., et al., Cancer Res. 41, 2700-2706, 1981; Shin, L. B., et al., Int. J. Cancer 41, 832-839, 1988; Gamett M. C., et al., Int. J. Cancer 31, 661-670, 1983); 5-Fluorouridine (Shin, L. B., Int. J. Cancer 46, 1101-1106, 1990); 5-Fluoro-2'-deoxyuridine (Goerlach A., et al., Bioconjugate Chem. 2, 96-101, 1991); Cytosine arabinoside (Hurwitz E., et al., J. Med. Chem. 28, 137-140, 1985); Aminopterin (Kanellos J., et al., Immunol. Cell. Biol. 65, 483-493, 1987); vincristine (Johnson J. R., et al., Br. J. Cancer 42, 17, 1980); vindesine (Johnson J. R., et al., Br. J. Cancer 44, 472-475, 1981); interleukine-2 (IL-2), tumor necrosis factor α (TNFa), interferon (INF), carboxypeptidase, alkaline phosphatase, β-lactamase, and cytidine deaminase.

The cytotoxic substances may be used in the present invention either individually or in combination of two or more species.

The anti-GRP78 antibody can be bound to the above-listed cytotoxic substances by covalent bonding, non-covalent bonding or the like. Methods of preparing antibodies conjugated with those cytotoxic substances are known.

The anti-GRP78 antibody and the cytotoxic substance can be directly bound together via the linking groups they have by themselves; alternatively, they may be bound together indirectly via other substances such as linkers or intermediate supports. Examples of the linking groups that occur in the case where the anti-GRP78 antibody and the cytotoxic substance are directly bound together include a disulfide bond using the SH groups. Specifically, the intramolecular disulfide bond in the Fc region of the antibody is reduced with a reducing agent, such as dithiothreitol, and the disulfide bond within the cytotoxic substance is likewise reduced so that the two are bound by the disulfide bond. Prior to binding, either the antibody or the cytotoxic substance may be activated by an activation promoting agent, such as an Ellman's reagent so that the formation of the disulfide bond between the two molecules is accelerated. Other approaches for directly binding the anti-GRP78 antibody and the cytotoxic substance include a method using a Schiff base, a carbodiimide method, an active ester method (N-hydroxysuccinimide method), a method using a mixed anhydride, and a method using a diazo reaction.

The anti-GRP78 antibody and the cytotoxic substance can also be bound together indirectly via other substances. Other substances for realizing indirect binding are not particularly limited and include, for example, compounds that have at least two substituents consisting of any one of an amino group, a carboxyl group, and a mercapto group or any combination of two or more groups, peptide linkers, and compounds having a capability of binding to the anti-GRP78 antibody. Examples of the compounds that have at least two substituents consisting of any one of an amino group, a carboxyl group, and a mercapto group or any combination of two or more groups include: N-succinimidyl 3-(2-pyridyldithio) propionate (SPDP) (Wawrzynczak E. J., et al., Cancer Res., 50, 7519-7562, 1990; Thorpe P. E., et al., Cancer Res., 47, 5924-5931, 1987); succinimidyl 6-3-[2-pyridyldithio]propionamide)hexanoate (LC-SPDP) (Hermanson G. T., BIOCONJUGATE Techniques, 230-232, 1996); sulfosuccinimidyl 6-3-[2-pyridyldithio]propionamide)hexanoate (sulfo-LC-SPDP) (Hermanson G. T., BIOCONJUGATE Techniques, 230-232, 1996); N-Succinimidyl 3-(2-pyridyldithio)butyrate (SPDB) (Wawrzynczak E. J., et al., Br. J. Cancer, 66, 361-366, 1992); succinimidyloxycarbonyl-a-(2-pyridyldithio)toluene (SMPT) (Thorpe P. E., et al., Cancer Res., 47, 5924-5931, 1987); succinimidyl 6-(a-methyl-[2-pyridyldithio]toluamide)hexanoate (LC-SMPT) (Hermanson G. T., BIOCONJUGATE Techniques, 232-235, 1996); sulfosuccinimidyl 6-(a-methyl-[2-pyridyldithio]toluamide) hexanoate (sulfo-LC-SMPT) (Hermanson G. T., BIOCONJUGATE Techniques, 232-235, 1996); succinimidyl-4-(p-maleimidophenyl)butyrate (SMPB) (Hermanson G. T., BIOCONJUGATE Techniques, 242-243, 1996); sulfo-succinimidyl-4-(p-maleimidophenyl)butyrate (sulfo-SMPB) (Hermanson G. T., BIOCONJUGATE Techniques, 242-243, 1996); m-maleimidobenzoyl-N-hydroxysuccinimide ester (MBS) (Hermanson G. T., BIOCONJUGATE Techniques, 237-238, 1996); m-maleimidobenzoyl-N-hydroxysulfosuccinimide ester (sulfo-MBS) (Hermanson G. T., BIOCONJUGATE Techniques, 237-238, 1996); S-acetyl mercaptosuccinic anhydride (SAMSA) (Casellas P., et al., Eur. J. Biochem, 176, 581-588, 1988); dimethyl 3,3'-dithiobisprorionimidate (DTBP) (Casellas P., et al., Eur. J. Biochem, 176, 581-588, 1988); and 2-iminothiolane (Thorpe P. E., et al., Cancer Res., 47, 5924-5931, 1987).

Other substances that may be used to bind the anti-GRP78 antibody and the cytotoxic substance may be exemplified by peptides, antibodies, poly(L-glutamic acid) (PGA), carboxymethyldextran, dextran, aminodextran, avidin-biotin, cis-aconitic acid, glutamic acid dihydrazide, and human serum albumin (HAS).

Further, proteinaceous cytotoxic substances can also be bound to the antibody by genetic engineering techniques. Specifically, a DNA coding for the above-mentioned cytotoxic peptide and a DNA coding for the anti-GRP78 antibody may be fused in frame and incorporated into an expression vector to construct a recombinant vector. This vector is then introduced into suitable host cells to generate transformed cells, which are cultured to express the incorporated DNA, whereby a fused protein of the anti-GRP78 antibody and the toxic peptide can be obtained. In the case of producing fusion proteins of the antibody and a cytotoxic substance, proteinaceous chemicals or toxins are typically positioned at the C terminus of the antibody. It is also possible to interpose a peptide linker between the antibody and the proteinaceous chemical or toxin.

The anti-GRP78 monoclonal antibody of the present invention can be acquired by known means. Monoclonal antibodies derived from mammalian animals are particularly preferred as the anti-GRP78 monoclonal antibody of the present invention. The monoclonal antibodies derived from mammalian animals include, for example, those which are produced by hybridomas, as well as those which are produced from host cells that have been transformed with expression vector harboring an antibody gene by genetic engineering techniques.

Monoclonal antibody producing hybridomas can typically be constructed as follows using known techniques. First, the GRP78 protein is used as a sensitizing antigen to effect immunization in accordance with a conventional immunization method. Immune cells obtained from the immunized animal are fused to known parent cells by a conventional cell fusion method to yield hybridomas. From the thus produced hybridomas, cells that produce the desired antibody are screened by a conventional screening method so as to select hybridomas that produce the anti-GRP78 protein.

Specifically, the monoclonal antibody preparation can typically be performed as described below. First, the GRP78 protein (SEQ ID NO: 2) to be used as a sensitizing antigen for antibody acquisition can be acquired by expressing the GRP78 gene. The nucleotide sequence of the human GRP78 gene has been already known (SEQ ID NO: 1). To be more specific, a gene sequence coding for GRP78 is inserted into a known expression vector to transform suitable host cells and the intended human GRP78 protein can be purified from the transformed host cells or the culture supernatant by a known method. A purified native GRP78 protein can also be used. Purification can be performed by a plurality of conventional chromatographic techniques such as ion chromatography and affinity chromatography, which are used once or more than once, either individually or in combination. In addition, as in the case of the present invention, a fusion protein of a desired partial polypeptide of the GRP78 protein with a different polypeptide may be used as an immunogen. To produce the fused protein that serves as an immunogen, Fc fragments of an antibody, peptide tags and the like may be used. To construct a vector that expresses the fused protein, genes that code for two or more desired polypeptide fragments may be fused in frame and the fused genes inserted into an expression vector as described above. The method of preparing fusion proteins is described in Sambrook, J. et al., Molecular Cloning $2^{nd}$ ed., 9.47-9.58, Cold Spring Harbor Lab. Press, 1989.

The thus purified GRP78 protein can be used as a sensitizing antigen to immunize mammals. Partial peptides of GRP78 can also be used as an sensitizing antigen. For example, the following peptides can serve as sensitizing antigens:

A peptide acquired by chemical synthesis from the amino acid sequence of human GRP78;

A peptide acquired by incorporating part of the human GRP78 gene into an expression vector and expressing the same;

A peptide acquired by decomposing the human GRP78 protein with a proteolytic enzyme.

The region and size of the GRP78 to be used as the partial peptide are by no means limited. A preferred region can be selected from the $376^{th}$ to $415^{th}$ region of GRP78 (SEQ ID NO: 3). The peptide that serves as a sensitizing antigen is preferably composed of at least three, for example five or six, amino acid residues. More specifically, a peptide of 8-50 residues, preferably 10-30 residues, can be used as a sensitizing antigen.

The mammals to be immunized with the sensitizing antigen are not particularly limited. To obtain a monoclonal antibody by the cell fusion method, the animal to be immunized is preferably selected in consideration of compatibility of the immunized cell with the parent cell to be used in cell fusion. In general, rodents are preferred animals to be immunized. Specifically, mouse, rat, hamster or rabbit may be used as an animal to be immunized. Other animals that may be immunized include monkey and the like.

The animals mentioned above can be immunized with the sensitizing antigen in accordance with known methods. An exemplary general method comprises immunizing a mammal by intraperitoneal or subcutaneous injection of the sensitizing antigen. Specifically, the sensitizing antigen is administered to the mammal several times every 4 to 21 days. The sensitizing antigen is used for immunization after it is diluted to a suitable dilution ratio with PBS (phosphate-buffered saline), physiological saline or the like. If desired, the sensitizing antigen may be administered together with an adjuvant. For example, the sensitizing antigen may be mixed with a Freund's complete adjuvant, which may be emulsified to make a desired sensitizing antigen. In addition, a suitable carrier may be used in immunization with the sensitizing antigen. Particularly in the case where a partial peptide having a small molecular weight is used as the sensitizing antigen, immunization is preferably done by binding the sensitizing antigen peptide to a carrier protein such as albumin or keyhole limpet hemocyanine.

With the mammal being thus immunized and after a increase in the amount of desired serum antibody is confirmed, the immune cells are collected from the mammal and subjected to cell fusion. Spleen cells can especially be used as preferred immune cells.

The cells to be fused with the immune cells are mammalian myeloma cells. Myeloma cells are preferably furnished with a selection marker suitable for screening. The selection marker refers to a phenotype that can survive (or cannot survive) under particular culture conditions. Known selection markers include hypoxanthine-guanine-phosphoribosyl transferase deficiency (hereinafter abbreviated as HGPRT deficiency) and thymidine kinase deficiency (hereinafter abbreviated as TK deficiency). Cells having HGPRT or TK deficiency have hypoxanthine-aminopterin-thymidine sensitivity (hereinafter abbreviated as HAT sensitivity). In a HAT selective medium, cells having HAT sensitivity are incapable of DNA synthesis and will die; however, if they are fused with normal cells, they can continue the synthesis of DNA by making use of the salvage circuit in the normal cell and hence will proliferate in the HAT selective medium.

Cells with HGPRT deficiency or TK deficiency can be selected in a medium containing 6-thioguanine, 8-azaguanine (hereinafter abbreviated as 8-AG) or 5'-bromodeoxyuridine. Normal cells incorporate these pyrimidine analogs into their DNA and will eventually die; on the other hand, cells lacking these enzymes are unable to incorporate those pyrimidine analogs and can hence survive in the selective medium. Another selection marker called G418 resistance confers resistance to 2-deoxystreptamine antibiotics (gentamycin analogs) by means of the neomycin resistance gene. A variety of myeloma cells suitable for cell fusion are known. Myeloma cells that can be used include: P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. Et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

Cell fusion of the above-mentioned immune cells and myeloma cells can be performed in accordance with known methods, such as the method of Kohler and Milstein (Kohler. G. and Milstein, C., Methods Enzymol. (1981) 73, 3-46).

More specifically, the above-mentioned cell fusion can typically be implemented in a conventional nutrient culture medium in the presence of a cell fusion promoting agent. Examples of the cell fusion promoting agent that can be used include polyethylene glycol (PEG) and Sendai virus (HVJ). If desired, an auxiliary agent such as dimethyl sulfoxide may be added in order to enhance fusion efficiency.

The proportions of the immune cells and myeloma cells to be used can be set at desired values. For example, the immune cells are preferably used in amounts ranging from one to ten times the amount of myeloma cells. Culture media that can be used in the aforementioned cell fusion include, for example, the RPMI1640 culture medium and MEM culture medium suitable for the growth of the above-mentioned myeloma cell line, as well as conventional culture media used in cell culture of the type under consideration. Further, a serum supplement such as fetal calf serum (FCS) may be added to the culture medium.

In cell fusion, specified amounts of the above-mentioned immune cells and myeloma cells are mixed well in the above-mentioned culture medium and then mixed with a pre-warmed (ca. 37° C.) PEG solution to form the desired fused cells (hybridomas). In the cell fusion method, PEG with an average molecular weight of from about 1000 to about 6000 can be added at concentrations typically ranging from 30 to 60% (w/v). Subsequently, procedures of sequentially adding suitable culture media as selected from those mentioned above, centrifuging them and removing the supernatant are repeated to thereby remove the cell fusion promoting agents and the like that are not preferred for the growth of hybridomas.

The hybridomas thus obtained can be selected by employing a selective culture medium in accordance with the selection marker possessed by the myeloma used in cell fusion. For instance, cells having HGPRT or TK deficiency can be selected by culturing them in a HAT culture medium (i.e., containing hypoxanthine, aminopterin, and thymidine). To be more specific, in the case of using HAT sensitive myeloma cells in cell fusion, the cells that successfully fused to normal cells can be selectively grown in the HAT culture medium. The fused cells are continuously cultured using this HAT culture medium for a sufficient time that cells (nonfused cells) other than the desired hybridomas will die. Specifically, the desired hybridomas can be selected by culturing for a period which typically ranges from several days to several weeks. Subsequently, a conventional method of limiting dilution is implemented to thereby enable the screening and a single cell cloning of hybridomas that produce the desired antibody. Alternatively, antibodies that recognize GRP78 can be constructed by the method described in WO 03/104453.

Screening and cloning of the desired antibodies can advantageously be implemented by screening methods based on known antigen-antibody reactions. For instance, the antigen is bound to a carrier such as beads made of polystyrene or otherwise or a commercial 96-well microtiter plate and reacted with the culture supernatant of hybridomas. Subsequently, the carrier is washed and thereafter reacted with enzyme-labeled secondary antibodies or the like. If the culture supernatant contains the desired antibodies that react with the sensitizing antigen, the secondary antibodies indirectly bind to the carrier via the desired antibodies. Finally, the secondary antibodies indirectly binding to the carrier are detected to thereby determine whether the desired antibodies are present in the culture supernatant. As a result, hybridomas that produce the desired antibodies having the ability to bind to the antigen can be cloned by limiting dilution method or a like. In this case, antigens that can preferably be used include not only the one that was used in immunization but also the GRP78 protein which is substantially of the same nature.

Aside from the method of obtaining the above-mentioned hybridomas by immunizing animals other than humans with the antigen, human lymphocytes may be sensitized with the antigen to obtain the desired antibodies. Specifically, human lymphocytes are sensitized in vitro with the GRP78 protein. Subsequently, the immunosensitized lymphocytes are fused to a suitable fusion partner. An exemplary fusion partner that can be used is myeloma cells that derive from humans and which are capable of permanent division (see JP 1-59878 B). The anti-GRP78 antibody obtained by this method is a human antibody having an activity for binding to the GRP78 protein.

Further, by administering the antigen GRP78 protein to a transgenic animal having the full repertoire of human antibody genes, the anti-GRP78 human antibody can also be obtained. The antibody producing cells in the immunized animal can be immortalized by such treatments as cell fusion with a suitable fusion partner and infection with Epstein-Barr virus or the like. From the thus obtained immortal cells, a human antibody against the GRP78 protein may be isolated (see WO 94/25585, WO 93/12227, WO 92/03918, and WO 94/02602). Further, the immortalized cells may be cloned to achieve cloning of cells that produce an antibody having the desired reaction specificity. If a transgenic animal is to be immunized, the immune system in that animal recognizes human GRP78 as foreign antigen. Hence, human antibodies against human GRP78 can be readily obtained. Hybridomas that produce the thus created monoclonal antibodies can be serially cultured in a conventional culture medium. If desired, those hybridomas can also be preserved in liquid nitrogen for an extended period.

The hybridomas may be cultured in accordance with an ordinary method and the desired monoclonal antibodies may be obtained from the culture supernatant. Alternatively, the hybridomas may be administered to a compatible mammal and allowed to proliferate, yielding monoclonal antibodies in the ascites. The former method is suitable for obtaining antibodies of high purity.

In the present invention, it is also possible to use antibodies that are encoded by the antibody gene cloned from the antibody producing cells. The cloned antibody gene may be incorporated into a suitable vector which is then introduced into a host cell so that it is expressed as an antibody. Methods for isolating the antibody gene, introducing it into a vector, and transforming host cells have already been established (see, for example, Vandamme, A. M. et al., Eur. J. Biochem. (1990) 192, 767-775).

For example, cDNA coding for the variable region (V region) of the anti-GRP78 antibody can be obtained from hybridoma cells that produce the anti-GRP78 antibody. To this end, total RNA is typically first extracted from the hybridomas. Exemplary methods for extracting mRNA from cells include guanidine ultracentrifugation (Chirgwin, J. M. et al., Biochemistry (1979) 18, 5294-5299) and the AGPC method (Chomczynski, P. et al., Anal. Biochem. (1987) 162, 156-159).

The extracted mRNA can be purified using a mRNA Purification Kit (product of GE Healthcare Bioscience) or the like. Alternatively, kits for extracting total mRNA directly from cells are commercially available, as exemplified by a QuickPrep mRNA Purification Kit (product of GE Healthcare Bioscience). These kits may be used to obtain total mRNA from the hybridoma cells. From the obtained mRNA, cDNA coding for the V region of the antibody can be synthesized using a reverse transcriptase. It is also possible to synthesize cDNA by an AMV Reverse Transcriptase First-strand cDNA Synthesis Kit (product of SEIKAGAKU CORPORATION) and the like. In addition, for cDNA synthesis and amplification, one can utilize the 5'-RACE method (Frohman, M. A. et al., Proc. Natl. Acad. Sci. USA (1988) 85, 8998-

9002; and Belyavsky, A. et al., Nucleic Acids Res. (1989) 17, 2919-2932) using 5'-Ampli FINDER RACE Kit (product of Clontech) and PCR. Furthermore, in this process of cDNA synthesis, a suitable restriction site (to be described later) may be introduced at both ends of cDNA.

The desired cDNA fragment is purified from the obtained PCR product and subsequently ligated to a vector DNA. A recombinant vector is thusly constructed and introduced into *E. coli* or the like; after colony selection, a desired recombinant vector can be prepared from *E. Coli* that has formed those colonies. Then, to determine whether the recombinant vector contains the nucleotide sequence of the desired cDNA, a known method such as the dideoxynucleotide chain termination technique may be adopted.

To obtain a gene coding for the variable region, it is also possible to utilize a PCR technique that employs primers for amplifying the variable region gene. First, the extracted mRNA is used as a template to synthesize cDNA to make a cDNA library. To synthesize a cDNA library, a commercial kit is conveniently used. In practice, an extremely small amount of mRNA can be obtained from a small number of cells alone, so only low yield results from direct purification of the mRNA. Hence, purification is conventionally performed after adding a carrier mRNA that obviously contains no antibody gene. Alternatively, if a certain amount of RNA can be extracted, the RNA of the antibody producing cells suffices for efficient extraction. For instance, RNA extraction from at least 10 or at least 30, preferably at least 50 antibody producing cells sometimes requires no addition of a carrier RNA.

The obtained cDNA library used as a template to amplify the antibody gene by a PCR method. Primers for amplifying the antibody gene by a PCR method are known. For example, primers for amplifying the human antibody gene can be designed on the basis of the disclosure in a scientific paper (J. Mol. Biol. (1991) 222, 581-597) or the like. These primers have different nucleotide sequences for different subclasses of immunoglobulin. Hence, if the cDNA library used as a template is unknown about which subclass it belongs to, every possibility must be considered in performing the PCR method.

Specifically, if it is desired to acquire a gene coding for human IgG, the primers that can be utilized are those which enable amplification of genes coding for γ1-γ5 heavy chains as well as κ and λ light chains. To amplify the variable region of IgG gene, a primer that anneals to a portion corresponding to the hinge region is typically used as the primer on the 3' side. On the other hand, a primer specific for the relevant subclass may be used as the primer on the 5' side.

PCR products obtained by using primers for amplifying the genes for the respective subclasses of heavy and light chains are used as independent libraries. Utilizing the thus synthesized libraries, immunoglobulins comprising the combination of heavy and light chains can be reconstituted. The activities of the reconstituted immunoglobulins for binding to GRP78 may be used as an index for screening the desired antibodies.

It is more preferred that the antibody of the present invention binds specifically to GRP78. Antibodies that bind to GRP78 can typically be screened through the following steps of:
(1) contacting with GRP78 an antibody that contains a V region encoded by the cDNA obtained from the hybridomas;
(2) detecting the binding between GRP78 and the antibody; and
(3) selecting antibodies that bind to GRP78.

Methods of detecting the binding between the antibody and GRP78 are known. Specifically, a subject antibody is reacted with GRP78 immobilized on a carrier, which is then treated with a labeled antibody that recognizes the antibody. Detection of the labeled antibody on the carrier after washing provides a proof for the binding of the subject antibody to GRP78. Labels that can be utilized include enzymatically active proteins such as peroxidase and β-galactosidase, and fluorescent substances such as FITC. To evaluate the binding activity of the antibody, fixed specimens of GRP78 expressing cells can also be utilized.

An applicable method of screening antibodies using the binding activity as an index is panning that utilizes a phage vector. If the antibody gene is acquired as described above in a library of heavy and light chain subclasses, it is advantageous to perform screening utilizing a phage vector. Genes coding for the variable regions of heavy and light chains may be ligated by a suitable linker sequence to make a single-chain Fv (scFv). If the gene coding for scFv is inserted into a phage vector, phages can be obtained that have scFv expressed on the surface. These phages are brought into contact with the desired antigen and the phages that have bound to the antigen are recovered, whereupon one can recover the DNA that codes for scFv having the desired binding activity. By repeating this procedure as necessary, the scFv having the desired binding activity can be enriched.

The polynucleotide that codes for the antibody in the present invention may encode the full length of the antibody or may encode part of the antibody. Part of the antibody refers to any portion of the antibody molecule. Hereinafter, the term "antibody fragment" may sometimes be used to indicate a part of the antibody. Preferred antibody fragments of the present invention contain a complementarity-determining region (CDR) of the antibody. More preferably, the antibody fragment according to the present invention contains all three CDRs that compose the variable region.

After cDNA coding for the V region of the desired anti-GRP78 antibody is obtained, this cDNA is digested with restriction enzymes that recognize those restriction sites which have been inserted at both ends of the cDNA. Preferred restriction enzymes recognize and digest those nucleotide sequences which are less likely to appear in the nucleotide sequences that compose the antibody gene. Further, in order to insert a single copy of digested fragment into a vector in the correct orientation, restriction enzymes that impart sticky ends are preferred. The thus digested cDNA that codes for the V region of the anti-GRP78 antibody may be inserted into a suitable expression vector to thereby provide an antibody-expressing vector. In this case, a gene coding for the antibody's constant region (C region) and a gene coding for the aforementioned V region may be fused in frame to provide a chimeric antibody. The term "chimeric-antibody" as used herein implies that the constant region derives from a different organism than the variable region. Hence, in addition to heterogeneous (e.g. mouse-human) chimeric antibodies, human-human homogeneous chimeric antibodies are also encompassed by the chimeric antibodies according to the present invention. A chimeric antibody-expressing vector can also be constructed by inserting the aforementioned V region gene into an expression vector that already has a constant region.

Specifically, an expression vector is provided that harbors DNA coding for a desired antibody's constant region (C region) and a sequence to be recognized by a restriction enzyme that digests the aforementioned V region gene may be located on the 5' side of the vector. The two genes are digested by the same combination of restriction enzymes and fused together in frame to construct a chimeric antibody-expressing vector.

To produce the anti-GRP78 antibody of the present invention, the antibody gene may be incorporated into an expression vector in such a way that it will be expressed under control by an expression-regulatory region. The expression-regulatory region for expressing the antibody may include an enhancer or a promoter. Subsequently, suitable host cells are transformed with this expression vector to yield recombinant cells expressing the DNA coding for the anti-GRP78 antibody.

Upon expressing the antibody genes, DNA coding for the antibody's heavy chain (H chain) and DNA coding for the light chain (L chain) may be respectively incorporated into different expression vectors. The vectors incorporating the H and L chains may be co-transfected in the same host cell to thereby express an antibody's molecule furnished with both H and L chains. Alternatively, DNA coding for the H chain and DNA coding for the L chain may be incorporated into a single expression vector for transforming host cells (see International Publication WO 94/11523).

A lot of combinations of host and expression vector are known for first isolating the antibody gene and then introducing it into a suitable host to prepare an antibody. All of these expression systems can be applied in the present invention. In the case of using eukaryotic cells as a host, animal cells, plant cells or fungal cells may be used. Specifically, animal cells that may be employed in the present invention include, for example, mammalian cells (e.g. CHO, COS, myeloma, BHK (baby hamster kidney), Hela, and Vero), amphibian cells (e.g. *Xenopus* oocytes), and insect cells (e.g. Sf9, Sf21, and Tn5).

Alternatively, plant cells may be used and in this case, systems for expressing the antibody gene in cells of species derived from the genus *Nicotiana* such as *Nicotiana tabacum* are known. For transformation of plant cells, cells obtained by callus culture may be utilized.

Furthermore, fungal cells that may be used include yeasts (the genus *Saccharomyces* including *Saccharomyces serevisiae* and the genus *Pichia* including *Pichia pastoris*) and filamentous fungi (the genus *Aspergillus* including *Aspergillus niger*).

Alternatively, expression systems are known for expressing the antibody gene utilizing prokaryotic cells. For example, in the case of using bacterial cells, *E. coli*, *Bacillus subtilis* and other bacterial cells may be utilized in the present invention.

In the case of using mammalian cells, an expression vector can be constructed that contains a commonly employed useful promoter, the antibody gene to be expressed, and a poly (A) signal that is functionally linked to the downstream of the 3' end. An exemplary promoter/enhancer is a human cytomegalovirus immediate early promoter/enhancer.

Other types of promoter/enhancer that can be used to express the antibody of the present invention include a viral promoter/enhancer and a mammalian cell derived promoter/enhancer such as a human elongation factor-1α (HEF1α). Viruses that can utilize the promoter/enhancer may specifically be exemplified by retrovirus, polyoma virus, adenovirus, and simian virus 40 (SV40).

In the case of using the SV40 promoter/enhancer, the method of Mulligan et al. (Nature (1979) 277, 108) may be utilized. In addition, the HEF1a promoter/enhancer may be readily utilized by the method of Mizushima et al. (Nucleic Acids Res. (1990) 18, 5322) to express the desired gene.

In the case of *E. coli*, a commonly employed useful promoter, a signal sequence for antibody secretion and the antibody gene to be expressed may be functionally linked together to express the gene of interest. Exemplary promoters include a lacZ promoter and an araB promoter. In the case of using a lacZ promoter, the method of Ward et al. (Nature (1989) 341, 544-546; FASEBJ. (1992) 6, 2422-2427) may be utilized. Alternatively, an araB promoter may be utilized to express the desired gene by the method of Better et al. (Science (1988) 240, 1041-1043).

For antibody secretion, a pelB signal sequence (Lei, S. P. et al., J. Bacteriol. (1987) 169, 4379) may be used as a signal sequence in the case of producing the antibody in the periplasm of *E. coli*. After separating the antibodies produced in the periplasm, a protein denaturing agent such as a guanidine hydrochloride of urea is used to thereby refold the structure of the antibodies in such a way that they have the desired binding activity.

Replication origin to be inserted into the expression vector may be that derived from SV40, polyoma virus, adenovirus, and bovine papilloma virus (BPV). Further in addition, a selection marker may be inserted into the expression vector in order to increase the number of gene copies in the host cell system. Specifically, selection markers that may be utilized include an aminoglycoside transferase (APH) gene, a thymidine kinase (TK) gene, an *E. coli* xyanthine guanine phosphoribosyl transferase (Ecogpt) gene, a dihydrofolate reductase (dhfr) gene, etc.

These expression vectors are introduced into host cells and the transformed host cells are cultured in vitro or in vivo to produce the desired antibody. The host cells are cultured in accordance with known methods. For example, DMEM, MEM, RPMI1640 or IMDM may be used as a culture medium, with a serum supplement such as fetal calf serum (FCS) being optionally used in combination.

The antibodies expressed and produced as described above can be purified by the methods used to purify ordinary proteins and they may be used either singly or in suitable combinations. For example, an affinity column such as a protein A column, a chromatographic column, a filter, ultrafiltration, salting out, dialysis, etc. may appropriately be selected and combined to separate and purify the antibodies (Antibodies—A Laboratory Manual, Ed Harlow, David Lane, Cold Spring Harbor Laboratory, 1988).

In addition to the above-mentioned host cells, transgenic animals can also be utilized to produce recombinant antibodies. To be more specific, such antibodies can be obtained from an animal into which a gene coding for the desired antibody has been introduced. For example, a fused gene containing the antibody gene can be constructed by inserting it in frame into a gene coding for the protein that is inherently produced in milk. An example of the protein to be secreted in milk is goat β casein. A DNA fragment containing the fused gene into which the antibody gene has been inserted is injected into a goat embryo, which is then introduced into a female goat. From the milk produced by a transgenic goat (or a offspring of the transgenic goat) born from the goat that received the embryo, the desired antibody can be acquired in the milk as a protein fused with the protein. In addition, in order to ensure that the milk containing the desired antibodies is produced from the transgenic goat in an increased amount, a hormone may be appropriately used in the transgenic goat (Ebert, K. M. et al., Bio/Technology (1994) 12, 699-702). A C region derived from an animal antibody can be used as the C region of the recombinant antibody of the present invention. For example, Cγ1, Cγ2a, Cγ2b, Cγ3, Cμ, Cd, Ca1, Ca2 or Ce may be used as the C region of H chains of the mouse antibody, and Cκ or Cγ as the C region of L chains. In addition to the mouse antibody, applicable animal antibodies include those of rat, rabbit, goat, sheep, camel, monkey, etc. The sequences of these animal antibodies are known. In addition, in order to improve the stability of antibodies or of their production, the C region may be modified. In the case where antibodies are to be administered to humans in the present invention, artificially modified recombinant antibodies may be employed for purposes of reducing a heterogenic antigenicity to humans. Examples of the recombinant antibodies include a chimeric antibody and a humanized antibody.

These modified antibodies can be produced using known methods. Chimeric antibodies are such that a variable region and a constant region that derive from different sources from each other are linked together. For example, an antibody comprising variable regions of heavy and light chains of a mouse antibody and constant regions of heavy and light chains in a human antibody is a mouse-human heterogeneous chimeric antibody. The DNA coding for the variable regions of the mouse antibody is linked to the DNA coding for the constant regions of the human antibody and the linked DNAs are incorporated into an expression vector to construct a recombinant vector that expresses a chimeric antibody. Recombinant cells transformed with the recombinant vector are cultured to express the incorporated DNAs, whereby the chimeric antibodies can be acquired as they are produced during culture. The C regions of the human antibody are used as those of the chimeric antibody and the humanized antibody. For example, in H chains, $C\gamma1$, $C\gamma2$, $C\gamma3$, $C\gamma4$, $C\mu$, Cd, Ca1, Ca2 and Ce can be utilized as C regions. In L chains, $C\kappa$ and $C\gamma$ can be used as C regions. The amino acid sequences of these C regions and the nucleotide sequences encoding thereof are known. In addition, in order to improve the stability of antibodies per se or of production of antibodies, the C regions of the human antibody may be modified.

In general, chimeric antibodies are composed of V regions of an antibody derived from non-human animals and C regions derived from a human antibody. In contrast, humanized antibodies are composed of a complementarity-determining region (CDR) of an antibody derived from non-human animals, a framework region (FR) derived from a human antibody, and a C region derived from a human antibody. The humanized antibody has lowered antigenicity in the human body, so it is useful as an active ingredient in the therapeutics of the present invention.

The variable region of an antibody is typically composed of three complementarity-determining regions (CDRs), each located between four frame regions (FRs). CDRs are regions that substantially determine the binding specificity of the antibody. The amino acid sequences of CDRs are highly diverse. On the other hand, the amino acid sequences that compose FRs often show high homology between antibodies even if they have different binding specificities. Hence, it is generally held that by translocating CDRs, the binding specificity of a certain antibody can be translocated into another antibody.

The humanized antibody is also called a reshaped human antibody. Specifically, a humanized antibody obtained by translocating CDRs of an antibody from a non-human animal, such as mouse, into the human antibody is known. General recombinant techniques for obtaining humanized antibodies are also known.

Specifically, overlap extension PCR is known as a method of translocating CDRs of a mouse antibody into human FRs. In overlap extension PCR, nucleotide sequences that encode CDRs of the mouse antibody to be translocated are attached to primers for synthesizing the FRs of a human antibody. A primer is prepared for each of the four FRs. It is generally considered that when translocating mouse CDRs into human FRs, selecting human FRs with high homology to the mouse FRs is advantageous by selected for the purpose of maintaining the function of CDRs. In other words, it is generally preferred to utilize human FRs that are composed of amino acid sequences having high homology to the amino acid sequences of FRs adjacent to the mouse CDRs to be translocated.

The nucleotide sequences to be linked are so designed that they will be linked together in frame. Human FRs are individually synthesized by the respective primers. As a result, there are obtained products in which DNAs coding for the mouse CDRs are attached to the respective FRs. The nucleotide sequences coding for the mouse CDRs in the respective products are so designed that they overlap each other. Subsequently, with the human antibody gene used as a template, the overlapped CDR regions of the synthesized products are annealed to each other to perform a complementary strand synthesis reaction. This reaction causes the human FRs to be linked together via the sequences of mouse CDRs.

Finally, full length of the V region gene in which three CDRs are linked to four FRs are amplified by means of primers that are annealed to its 5' and 3' ends and which have suitable restriction enzyme recognition sequences added thereto. The thus obtained DNA and the DNA coding for the C region of the human antibody are inserted into an expression vector such that they will be fused together in frame, whereby a humanized antibody expression vector can be constructed. This recombinant vector is introduced into host cells to establish recombinant cells, which are then cultured to express the DNA coding for the humanized antibody, whereupon the humanized antibodies are produced in the culture of the cultured cells (see European Patent Publication EP 239400 and International Publication WO 96/02576).

The thus prepared humanized antibodies are qualitatively or quantitatively measured and evaluated for their activity for binding to antigens and this allows for advantageous selection of those FRs of the human antibody which can be linked together via CDRs such that the CDRs will form desired antigen binding sites. If necessary, the amino acid residues of FRs may be replaced such that the CDRs of the reconstructed human antibody will form appropriate antigen binding sites. For instance, alterations of the amino acid sequences can be introduced into FRs by applying the PCR method used to translocate the mouse CDRs into the human FRs. Specifically, alterations of partial nucleotide sequences can be introduced into the primers that are to anneal to the FRs. The FRs synthesized by means of such primers have the variations in nucleotide sequences introduced thereinto. The variant antibody with substituted amino acids is measured and evaluated for its binding activity to antigens by the above-described methods, whereupon variant FR sequences having the desired properties can be selected (Sato, K. et al., Cancer Res, 1993, 53, 851-856).

Methods of acquiring the human antibody are also known in the art. For instance, human lymphocytes are sensitized in vitro with desired antigen or cells expressing the desired antigen. Subsequently, the sensitized lymphocytes are fused to human myeloma cells, whereby the desired human antibodies can be acquired that have the activity for binding to the antigen (see JP 1-59878 B). The human myeloma cells that are used as the fusion partner may be exemplified by U266.

The desired human antibody can also be acquired by immunizing with the desired antigen a transgenic animal having the full repertoire of human antibody genes (see International Publications WO 93/12227, WO 92/03918, WO 94/02602, WO 94/25585, WO 96/34096, and WO 96/33735). Also known is a technique that uses panning method with a human antibody library to acquire the human antibody. For example, the V region of a human antibody can be expressed as a single-chain antibody (scFv) on the surface of phages by the phage display method and those phages that bind to the antibody can be selected. By analyzing the gene of the selected phages, the DNA sequence that codes for the V region of the human antibody that binds to the antigen can be determined. After determining the DNA sequence of scFv that binds to the antigen, this V region sequence is fused in frame to the sequence of the desired human antibody's C region, which is then thereafter inserted into a suitable expression vector to construct expression vectors. The expression vectors are then introduced into the suitable host cells mentioned above so that the gene coding for the desired human antibody is expressed in the host cells to yield the desired human antibodies. These methods are already known (International Publications WO 92/01047, WO 92/20791, WO 93/06213, WO 93/11236, WO 93/19172, WO 95/01438 and WO 95/15388).

As long as they bind to the GRP78 protein, the antibodies of the present invention include not only bivalent antibodies such as IgG but also monovalent antibodies, as well as polyvalent antibodies such as IgM. The polyvalent antibodies according to the present invention include those whose antigen binding sites are identical, as well as those having partly or entirely different antigen binding sites. The antibodies of the present invention are not limited to full-length molecules of antibodies and as long as they bind to the GRP78 protein, they may be small molecular antibodies or their modifications.

The small molecular antibodies include antibody fragments, or fragments of a whole antibody (e.g. whole IgG) which are deficient of partial regions. As long as the ability to bind to the GRP78 antigen is retained, the partially deficient antibody molecule is available. The antibody fragment in the present invention preferably contains either a heavy-chain variable region (VH) or a light-chain variable region (VL) or both. The amino acid sequence of VH or VL may contain a substitution, deletion, addition and/or insertion. Furthermore, as long as the ability to bind to the GRP78 antigen is retained, either VH or VL or a part of both regions may be deficient. If desired, the variable region may be chimeric or humanized. Specific examples of the antibody fragment include Fab, Fab', F(ab')2 and Fv. Specific examples of the small molecular antibody include Fab, Fab', F(ab')2, Fv, scFv (single-chain Fv), Diabody, and sc(Fv)2 (single-chain (Fv)2). Multimers of these antibodies (e.g. dimers, trimers, tetramers and polymers) are also encompassed by the small molecular antibodies according to the present invention.

Fragments of antibodies can be obtained by treating the antibodies with enzymes to generate antibody fragments. Known examples of enzymes that can generate antibody fragments include papain, pepsin, and plasmin. Alternatively, a gene coding for one of these antibody fragments may be constructed, introduced into an expression vector, and expressed in a suitable host cell (see, for example, Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

Digesting enzymes cleave antibody fragments at specific positions to provide antibody fragments having the following specific structures. Such enzymatically obtained antibody fragments may further be treated by genetic engineering techniques to delete any desired portions of the antibody.

Papain digestion: F(ab)$_2$ or Fab;
Pepsin digestion: F(ab')2 or Fab';
Plasmin digestion: Facb.

The "diabody" refers to a bivalent antibody fragment constructed by gene fusion (Holliger P et al., Proc. Natl. Acad. Sci. USA 90: 6444-6448 (1993), EP 404097, WO 93/11161, etc.). A diabody is a dimer composed of two polypeptide chains. Each of the polypeptide chains that compose a dimer is usually such that VL and VH are linked by a linker in the single chain. The linkers in a diabody are typically so short that VL and VH in the single chain away from the linker cannot bind to each other. Specifically, the amino acid residues that compose a linker may be about five in number. Hence, VL and VH that are encoded on the single polypeptide chain cannot form a single-chain variable region fragment but forms a dimer with another single-chain variable region fragment. As a result, the diabody will have two antigen binding sites.

The scFv is obtained by linking the V region of H chain and the V region of L chain in the antibody. In scFv, the V region of H chain and the V region of L chain are linked via a linker, preferably a peptide linker (Huston, J. S. et al., Proc. Natl. Acad. Sci. U.S.A, 1988, 85, 5879-5883). The V region of H chain and the V region of L chain in scFv may be derived from any of the antibodies mentioned herein. The peptide linker that links the two V regions is not particularly limited. For example, any single-chain peptide composed of from about 3 to 25 amino acid residues may be used as a linker. The V regions can typically be linked by the PCR method described above. For linking the V regions by the PCR method, DNA coding for the amino acid sequences of the DNA sequence coding for the H chain or its V region in the aforementioned antibody and of the DNA sequence coding for the L chain or its V region in the aforementioned antibody is utilized as a template.

By the PCR method using a pair of primers that have sequences corresponding to the sequences at both ends of the DNA to be amplified, the DNA coding for the V region of H chain and the DNA coding for the V region of L chain are each amplified. Subsequently, DNA coding for the peptide linker portion is prepared. The DNA coding for the peptide linker can also be synthesized by utilizing PCR. In this instance, a separately synthesized an additional nucleotide sequence that can link to an amplified product of each V region is attached to the 5' end of each of the primers to be utilized. Subsequently, a PCR reaction is performed utilizing each of the DNAs of [H-chain V region DNA]-[peptide linker DNA]-[L-chain V region DNA] and primers for assembly PCR. The primers for assembly PCR comprise the combination of a primer that anneals to the 5' end of [H-chain V region DNA] and a primer that anneals to the 3' end of [L-chain V region DNA]. In other words, the primers for assembly PCR constitute a primer set that can amplify the DNA coding for the full-length sequence of scFv to be synthesized. On the other hand, a nucleotide sequence that can link to the DNA of each V region is attached to [peptide linker DNA]. As a result, the DNAs described above are linked and with the aid of the primers for assembly PCR, the full length of scFv is eventually generated as an amplified product. Once the DNA coding for scFv is constructed, an expression vector that contains it and recombinant cells transformed with that expression vector can be acquired in accordance with the usual manner. In addition, the resulting recombinant cells may be cultured to express the DNA coding for the scFv, whereupon the scFv can be acquired.

Note that sc(Fv)2 is a small molecular antibody obtained by binding two VHs and two VLs into a single chain with linkers or the like (Hudson et al, J. Immunol. Methods 1999; 231: 177-189). This sc(Fv)2 can typically be prepared by connecting two scFv molecules with a linker.

A preferred antibody is such that two VHs and two VLs are arranged in the order of VH, VL, VH and VL (i.e., [VH]-linker-[VL]-linker-[VH]-linker-[VL]), starting at the N-terminal side of a single-chain polypeptide.

The order of two VHs and two VLs is by no means limited to the arrangement shown above and they may be arranged in any other orders, including the following arrangements:

[VL]-linker-[VH]-linker-[VH]-linker-[VL];
[VH]-linker-[VL]-linker-[VL]-linker-[VH];
[VH]-linker-[VH]-linker-[VL]-linker-[VL];
[VL]-linker-[VL]-linker-[VH]-linker-[VH]; and
[VL]-linker-[VH]-linker-[VL]-linker-[VH].

Linkers that may be used to link the variable regions of an antibody include any peptide linkers that can be introduced by genetic engineering and synthetic compound linkers (e.g. the linker disclosed in Protein Engineering, 9(3), 299-305, 1996). Peptide linkers are preferred in the present invention. The length of peptide linkers is not particularly limited and may be selected by skilled artisans as appropriate for a specific object. The amino acid residues that compose peptide linkers typically consist of 1 to 100 amino acids, preferably 3 to 50 amino acids, more preferably 5 to 30 amino acids, and most preferably 12 to 18 amino acids (say, 15 amino acids).

The peptide linkers may be composed of any amino acid sequences as long as they will not compromise the binding action of scFv.

Alternatively, synthetic compound linkers (chemical crosslinking agents) may also be utilized to link the V regions. Crosslinking agents commonly used to crosslink peptide compounds and the like may be utilized in the present invention. Examples that may be used include N-hydroxysuccinimide (NHS), disuccinimidyl suberate (DSS), bis(sulfosuccinimidyl)suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

To link four variable regions of an antibody together, three linkers are usually required. The linkers may be the same or different from each other. A small molecular antibody that is preferred in the present invention is a diabody or sc(Fv)2. To obtain such small molecular antibodies, an antibody may be treated with an enzyme such as papain or pepsin to generate antibody fragments; alternatively, DNA coding for such antibody fragments may be constructed, introduced into an expression vector, and expressed in a suitable host cell (see, for example, (Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Further, the antibody of the present invention may be used as a modified antibody in which it is bound to various molecules such as polyethylene glycol (PEG). Such modified antibodies can be obtained by chemically modifying the antibody of the present invention. Methods of modifying antibodies have already been established in the art.

Further in addition, the antibody of the present invention may be a bispecific antibody. The bispecific antibody refers to such an antibody that variable regions that recognize different epitopes are present in the same antibody molecule; the epitopes may be present in different molecules or they may be present in the same molecule. Thus, in the present invention, the bispecific antibody may possess antigen binding sites that recognize different epitopes on the GRP78 molecule; alternatively, it may be such a bispecific antibody that one of the two recognition sites recognizes GRP78 whereas the other recognizes a cytotoxic substance. The "antibody" in the present invention encompasses these antibodies.

In the present invention, the antibody may be constructed by combining with bispecific antibodies that recognize antigens other than GRP78. For example, it may be combined with a bispecific antibody that recognizes an antigen different from GRP78 but which, like GRP78, is specifically expressed on the cell surface of the target cancer cells.

Methods for producing bispecific antibodies are known. For example, two kinds of antibody that recognize different antigens may be bound to construct a bispecific antibody. Each of the antibodies to be bound may be a ½ molecule that has both H and L chains or it may be a ¼ molecule having only a H chain. Alternatively, hybridomas producing different monoclonal antibodies may be fused to construct bispecific antibody producing fused cells. Still another way to prepare a bispecific antibody is by genetic engineering techniques.

Binding Activity of Antibody

The activity of antibodies for binding to antigens can be measured by known methods (Antibodies—A Laboratory Manual. Ed Harlow, David Lane, Cold Spring Harbor Laboratory, 1988). For example, ELISA (enzyme-linked immunosorbent assay), EIA (enzyme immunoassay), RIA (radioimmunoassay) or immunofluorescence may be employed. Further, techniques for measuring the activity of antibodies for binding to antigens expressed in cells include the method described in Antibodies—A Laboratory Manual, ibid, pp. 359-420.

To measure the binding between an antigen expressed on the surface of cells suspended in a buffer solution or the like and the antibody against that antigen, a method using a flow cytometer may advantageously be employed. Examples of the flow cytometr that may be used include FACSCanto™ II, FACSAria™, FACSArray™, FACSVantage™ SE, and FACSCalibur™ (these are available from BD Biosciences), as well as EPICS ALTRA HyPerSort, Cytomics FC 500, EPICS XL-MCL ADC EPICS XL ADC, and Cell Lab Quanta/Cell Lab Quanta SC (these are available from Beckman Coulter).

An advantageous method for measuring the activity of the GRP78 antibody to bind to antigens comprises a method comprising steps of reacting the subject antibody with cells expressing GRP78, staining the subject antibody with an FITC-labeled secondary antibody that recognizes the subject antibody, performing measurement with FACSCalibur (BD Biosciences), and analyzing the fluorescence intensity data with CELL QUEST Software (BD Biosciences).

Growth Suppressing Activity

To evaluate or measure the cell growth suppressing effect based on the anti-GRP78 antibody, the following methods may advantageously be employed. A method for evaluating or measuring this cell growth suppressing activity in vitro is such that the uptake by viable cells of [$^3$H]-labeled thymidine added into a culture medium is measured as an index for DNA replicating ability. More convenient methods that may be employed include a dye exclusion method in which the ability to exclude a dye such as trypan blue to the outside of cells is measured under a microscope, as well as the MTT method.

The latter method utilizes the ability of viable cells to convert the tetrazolium salt MTT (3-(4,5-dimethylthiazol-2-yl)-2,5-diphenyl tetrazolium bromide) to a blue formazan product. More specifically, the subject antibody as well as a ligand is added to a culture medium containing the subject cells and after a certain period of time, an MTT solution is added to the culture medium, which is allowed to stand for a certain period of time, whereupon MTT is incorporated into the cells. As a result, the MTT which is a yellow compound is converted to a blue compound by means of succinate dehydrogenase in the intracellular mitochondria. The blue product is dissolved to develop color, whose absorbance is measured for use as an index for the viable cell count. Aside from MTT, reagents such as MTS, XTT, WST-1 and WST-8 are also available on the market (as from nacalai tesque) and may advantageously be used. For activity measurement, a control antibody may also be used.

A tumor bearing mouse model may be used as a method of in vivo evaluation or measurement of the cell growth suppressing activity. For example, cancer cells expressing GRP78 are transplanted intradermally or subcutaneously into a subject non-human animal and starting on the same day or the next day, the subject antibody is administered intravenously or intraperitoneally every day or at intervals of several days. The size of the tumor is measured over time (in days) to evaluate the cell growth suppressing activity of the subject antibody. As in the evaluation in vitro, a control antibody is administered and if the tumors in the group administered with the anti-GRP78 antibody are significantly smaller than the tumors in the group administered with the control antibody, the subject antibody may be found to have the cell growth suppressing activity. If a mouse is used as a subject non-human animal, a nude (nu/nu) mouse that hereditarily lacks the thymus to be deprived of the function of T lymphocytes may advantageously be used. By using this mouse, the involvement of T lymphocytes in the subject animal can be eliminated when the cell growth suppressing activity of the administered antibody is evaluated or measured.

Method of Suppressing the Growth of Cells

The present invention provides a method of suppressing the growth of GRP78 expressing cells by bringing them into contact with the antibody of the present invention. The antibody of the present invention has already been described on the foregoing pages as an antibody that binds to the GRP78 protein contained in the cell growth suppressing agent of the present invention. The cells to be contacted by the anti-GRP78 antibody are not particularly limited if GRP78 has been expressed; preferably, they are such cells that GRP78 is localized on the cell membrane, and they are preferably associated with disease. Preferred examples of cells associated with disease include cancer cells. Also included are vascular endothelial cells that are present in a malignant tumor (tumor vessels) in the preferred examples of cells. The target cancer types are not particularly limited and include, for example, prostate cancer, breast cancer, pancreas cancer, liver cancer, lung cancer, esophagus cancer, melanoma, colon cancer, stomach cancer, ovary cancer, bladder cancer, and brain tumor.

Method of Delivery Using Anti-GRP78 Antibody

The present invention relates to a method of delivering a cytotoxic substance into cells using the GRP78 antibody. The antibody to be used in the present invention is the anti-GRP78 antibody that is conjugated with the above-mentioned cytotoxic substance. In this case, it is preferably an antibody having an internalizing activity. Delivery of the cytotoxic substance can be performed by establishing contact between the anti-GRP78 antibody that is conjugated with the cytotoxic substance and a cell that expresses GRP78. In the present invention, the cells into which the cytotoxic substance is to be delivered are not particularly limited but they are preferably such cells that GRP78 is localized on the cell membrane, and they are preferably associated with disease. Preferred examples of cells associated with disease include cancer cells. Also included are vascular endothelial cells that are present in a malignant tumor (tumor vessels) in the preferred examples of cells. The target cancer types are not particularly limited and include, for example, prostate cancer, breast cancer, pancreas cancer, liver cancer, lung cancer, esophagus cancer, melanoma, colon cancer, stomach cancer, ovary cancer, bladder cancer, and brain tumor.

In the present invention, the contact may be established in vitro or in vivo. In these cases, the antibody to be added may appropriately be in the form of a solution or of solid which is formed by freeze-drying or otherwise in other forms. If the antibody is to be added in an aqueous solution, the aqueous solution may contain only the antibody as the sole component or the antibody with other substances such as a surfactant, an excipient, a coloring agent, an odorizer, a preservative, a stabilizer, a buffer, a suspending agent, an isotonization agent, a binder, a disintegrator, a lubricant, a fluidity promoter, a flavoring agent, etc. The concentration at which the antibody is added is not particularly limited and it may advantageously be used to give a final concentration in the culture medium which is preferably in the range from 1 pg/ml to 1 g/ml, more preferably from 1 ng/ml to 1 mg/ml, and even more preferably from 1 µg/ml to 1 mg/ml.

In the present invention, in vivo "contact" may also be effected by administration into a non-human animal which has GRP78 expressing cells transplanted into their body or into animals, including humans, that possess cancer cells expressing GRP78 endogenously. Administration can be performed either orally or parenterally. Administration by parenteral route is particularly preferred and specific examples of this method include injection, transnasal administration, transpulmonary administration, and transdermal administration. In the case of an injection, the pharmaceutical composition, the cell growth inhibitor and the anticancer agent according to the present invention can be administered systemically or topically by intravenous injection, intramuscular injection, intraperitoneal injection, subcutaneous injection or the like. In addition, the method of administration can appropriately be selected for the age or symptoms of the subject animal. If the antibody is administered in the form of an aqueous solution, the aqueous solution may contain only the antibody as the sole component or the antibody with other substances such as a surfactant, an excipient, a coloring agent, an odorizer, a preservative, a stabilizer, a buffer, a suspending agent, an isotonization agent, a binder, a disintegrator, a lubricant, a fluidity promoter, a flavoring agent, etc. The dosage may be selected from the range of 0.0001 mg to 1000 mg per kg of body weight for a single administration. Alternatively, the dosage can be selected from the range of 0.001 to 100,000 mg/body per patient. It should, however, be noted that the dosage of the antibody to be administered in the present invention is by no means limited to the values indicated above.

Pharmaceutical Compositions

In another aspect, the present invention is characterized by providing a pharmaceutical composition comprising an antibody that binds to the GRP78 protein. The present invention is also characterized by providing a cell growth suppressing agent, in particular, an anticancer agent that contains an antibody that binds to the GRP78 protein. The cell growth suppressing agent and anticancer agent of the present invention are preferably administered to a subject who suffers or is suspected of suffering from cancer.

In the present invention, the cell growth suppressing agent that contains an antibody that binds to the GRP78 protein may also be expressed as a method of suppressing cell growth which includes the step of administering a subject with an antibody that binds to the GRP78 protein or as use of such antibody in the manufacture of a cell growth suppressing agent.

In the present invention, the anticancer agent that contains an antibody that binds to the GRP78 protein may be rewritten as a method of preventing or treating cancer which includes the step of administering a subject with an antibody that binds to the GRP78 protein or as use of such antibody in the manufacture of an anticancer agent.

The antibody to be contained in the pharmaceutical composition (e.g. cell growth suppressing agent or anticancer agent) of the present invention is not particularly limited as long as it binds to the GRP78 protein, and any of the antibodies that are given as examples herein may be used.

The pharmaceutical compositions of the present invention can be administered either orally or parenterally. Administration by parenteral route is particularly preferred and specific examples of this method include injection, transnasal administration, transpulmonary administration, and transdermal administration. In the case of an injection, the pharmaceutical compositions of the present invention can be administered systemically or topically by intravenous injection, intramuscular injection, intraperitoneal injection, subcutaneous injection or the like. In addition, the method of administration can be selected as appropriate for the age or symptoms of the patient. The dosage may be selected from the range of 0.0001 mg to 1000 mg per kg of body weight for a single administration. Alternatively, the dosage can be selected from the range of 0.001 to 100,000 mg/body per patient. It should, however, be noted that the dosage of the pharmaceutical compositions to be administered in the present invention is by no means limited to the values indicated above.

The pharmaceutical compositions of the present invention can be formulated according to the usual procedures (see, for example, Remington's Pharmaceutical Science, latest edition, Mark Publishing Company, Easton, U.S.A), optionally together with pharmaceutically acceptable carriers and additives. Examples include a surfactant, an excipient, a coloring agent, an odorizer, a preservative, a stabilizer, a buffer, a suspending agent, an isotonization agent, a binder, a disintegrator, a lubricant, a fluidity promoter, a flavoring agent, etc. but these are not the sole cases and other common carriers may be used as appropriate. Specific examples include light silicic anhydride, lactose, microcrystalline cellulose, mannitol, starch, carmelose calcium, carmelose sodium, hydroxypropyl cellulose, hydroxypropyl methylcellulose, polyvinyl acetal diethyl aminoacetate, polyvinyl pyrrolidone, gelatin, medium-chain fatty acid triglycerides, polyoxyethylene-hardened castor oil 60, sucrose, carboxymethylcellulose, corn starch, and inorganic salts.

Process for Producing Pharmaceuticals

The present invention further provides a process for producing a pharmaceutical, in particular, an anticancer agent, which comprises the following steps of:
 (a) providing anti-GRP78 antibodies;
 (b) validating whether the antibodies of (a) have an internalizing activity;
 (c) selecting antibodies having an internalizing activity; and
 (d) binding a cytotoxic substance to the antibodies selected in (c).

The presence or absence of an internalizing activity can be confirmed by the methods described on the foregoing pages. As regards the anti-GRP78 antibodies and the cytotoxic substance, the anti-GRP78 antibody and cytotoxic substance that have been described on the foregoing pages may be employed.

Diagnosis of Cancer

The present invention also provides a method of diagnosing disease, in particular cancer, using an anti-GRP78 antibody.

The diagnostic method of the present invention can be performed by detecting the anti-GRP78 antibody incorporated into cells. The anti-GRP78 antibody to be used in the present invention preferably has an internalizing activity, and it is also preferred that the antibody is labeled with a labeling substance.

Hence, a preferred embodiment of the diagnostic method of the present invention is by using an anti-GRP78 antibody that is labeled with a labeling substance and which has an internalizing activity. The anti-GRP antibody to which a labeling substance is bound may be the anti-GRP78 antibody that has been described on the foregoing pages.

The labeling substance to be bound to the anti-GRP78 antibody is not particularly limited and labeling substances known to skilled artisans such as a fluorescent dye, an enzyme, a co-enzyme, a chemoluminescent material, and a radioactive material may be employed; specific examples include radioisotopes (e.g. $^{32}P$, $^{14}C$, $^{125}I$, $^{3}H$, and $^{131}I$), fluorescein, rhodamine, dansyl chloride, umberiferron, luciferase, peroxidase, alkali phosphatase, β-galactosidase, β-glucosidase, horse raddish peroxidase, glucoamylase, lysozyme, saccharide oxidase, microperoxidase, and biotin. If biotin is used as a labeling substance, after the addition of the biotin-labeled antibody, avidin that is conjugated with an enzyme, such as alkali phosphatase, is preferably added. To bind the labeling substance and the anti-GRP78 antibody, a known method may be employed, such as the glutaraldehyde method, maleimide method, pyridyl disulfide method, or the periodic acid method.

The labeling substance can be conjugated with the antibody by any methods known to skilled artisans.

In the case where the disease to be diagnosed by the method of the present invention is cancer, the target cancer types are not particularly limited and include, for example, prostate cancer, breast cancer, pancreas cancer, liver cancer, lung cancer, esophagus cancer, melanoma, colon cancer, stomach cancer, ovary cancer, bladder cancer, and brain tumor.

Diagnosis in the present invention may be performed eiher in vivo or in vitro.

If diagnosis is to be performed in vitro, diagnosis is conducted by a method comprising the following steps of:
 (a) providing a sample collected from a subject to be diagnosed;
 (b) bringing the sample of (a) to an anti-GRP78 antibody that is conjugated with a labeling substance; and
 (c) detecting antibodies that have been incorporated into cells.

The sample to be collected is not particularly limited and cells or tissues collected from the subject to be diagnosed may be mentioned as examples. In addition, secondary samples obtained from the subject sample, such as specimens in which tissues or cells collected from the body of an organism have been fixed or a culture medium containing cells, are also included in the category of the sample according to the present invention.

If diagnosis is to be performed in vivo, diagnosis is conducted by a method comprising the following steps of:

(a) administering a subject to be diagnosed with an anti-GRP78 antibody that is conjugated with a labeling substance; and (b) detecting antibodies that have been incorporated into cancer cells.

The dosage of the anti-GRP78 antibody can appropriately be determined by skilled artisans based on the type of the labeling substance and the type of the disease to be diagnosed. The labeled anti-GRP78 antibody may be formulated by the methods described on the foregoing pages.

The present invention further provides a process for producing a diagnostic agent, in particular one for cancer diagnosis, which comprises the following steps of:

(a) providing anti-GRP78 antibodies;

(b) validating whether the antibodies of (a) have an internalizing activity;

(c) selecting antibodies having an internalizing activity; and (d) binding a labeling substance to the antibodies selected in (c).

The presence or absence of an internalizing activity can be confirmed by the methods described on the foregoing pages. As regards the anti-GRP78 antibodies and the labeling substance, the anti-GRP78 antibody and labeling substance that have been described on the foregoing pages may be employed.

Partial Peptides of GRP78

The present invention provides a polypeptide comprising the amino acid sequence of SEQ ID NO: 3 (the $376^{th}$ to $415^{th}$ of GRP78) or a fragment thereof. A polypeptide comprising the amino acid sequence of SEQ ID NO: 3 (the $376^{th}$ to $415^{th}$ of GRP78) or a fragment thereof is useful for evaluating the immunogen used in generating the antibody of the present invention or the binding activity of the antibody generated. In the present invention, fragments comprise at least 5 amino acids, preferably at least 10 amino acids, more preferably at least 15 amino acids. Examples of the fragments of polypeptides comprising the amino acid sequence of SEQ ID NO: 3 are not particularly limited and may include a fragment comprising the amino acid sequence from the $384^{th}$ to $391^{st}$ of GRP78 (a fragment comprising the sequence of amino acids 9-16 in SEQ ID NO: 3), a fragment comprising the amino acid sequence from the $392^{nd}$ to $407^{th}$ of GRP78 (a fragment consisting of the sequence of amino acids 17-32 in SEQ ID NO: 3), and a fragment comprising the amino acid sequence from the $400^{th}$ to $415^{th}$ of GRP78 (a fragment comprising the sequence of amino acids 25-40 in SEQ ID NO: 3).

EXAMPLES

Example 1

Immunization 1-1. Preparing an Immunogen 1-1-11. Constructing a GRP78 E. coli Expressing Vector To construct a GRP78 E. coli expressing vector, cloning of the GRP78 gene was first performed as follows. In the first place, with human colon adenocarcinoma cDNA (MTC Multiple Tissue cDNA panel, Clontech) used as a template, a full-length GRP78 gene was cloned by performing RT-PCR under the following conditions using Pyrobest Taq polymerase (Takara).

```
GRP-1: atgaagctct ccctggtggc        (SEQ ID NO: 26)

GRP-2: ctacaactca tcttttctg ctgta    (SEQ ID NO: 27)
```

(94° C.×30 sec, 58° C.×30 sec, 72° C.×120 sec: 27 cycles)

In the next step, with the obtained PCR product used as a template, another PCR was run under the following conditions to generate a GRP78 cDNA fragment having a BamHI and an XhoI cleavage sequence attached to the 5' and 3' ends, respectively, of a GRP78 gene fragment comprising base Nos. of 55-1965 in the nucleotide sequence of SEQ ID NO: 1.

```
GRP-GST-1:
                                    (SEQ ID NO: 28)
   aaaggatccg aggaggagga caagaaggag gacgtggg GRP-GST-2:
                                    (SEQ ID NO: 29)
   tttctcgagc tacaactcat cttttctgc tgtatcctc
```

(94° C.×30 sec, 64° C.×30 sec, 72° C.×120 sec: 25 cycles)

The obtained GRP78 cDNA fragment was cleaved with BamHI and XhoI and inserted downstream of the GST code region of an E. coli GST fused expression vector that had been similarly cleaved with BamHI and XhoI (pGEX-6P-1, Amersham Pharmacia) to construct a GRP78-GST fused protein expression vector (pGEX-GRP78-full).

1-1-2. Inducing the Expression of GST Fused GRP78 Protein and its Purification

In the next step, the GRP78 protein was prepared as an immunogen for acquiring GRP78 binding antibodies.

First, E. coli (BL21) was transformed with PGEX-GRP78-full. The transformed cells were cultured in an LB medium (300 mL) and when an $OD_{610}$ value of at least 0.5 was reached, IPTG was added to give a concentration of 0.5 mM, whereby induction of protein expression was effected. After 5-hr culture, the E. coli cells were harvested by centrifugation.

The harvested E. coli cells were suspended in 30 ml of B-PER (PIERCE) to be lysed. The E. coli lysate obtained was diluted 10-fold with PBS; to the diluted lysate, PBS-equilibrated glutathione Sepharose 4B (Amersham Pharmacia) was added, followed by incubation at 4° C. overnight. Thereafter, several washings with PBS were done to remove any unadsorbed proteins and reaction with PreScissuion Protease (Amersham Pharmacia) was performed at 4° C. overnight in a protease reaction solution (50 mM Tris-HCl, 150 mM NaCl, 1 mM EDTA, 1 mM DTT, pH 7.5). By this procedure, the GST protein and GRP78 protein (amino acids 19-654) in the GRP78-GST fused proein were separated off from each other. Subsequently, the GRP78 protein eluted by protease digestion was separated by gel filtration chromatography on Superdex 200 HR 10 30 column (Amersham Pharmacia) to recover the desired GRP78 protein (amino acids 19-654).

1-2. Immunization

Emulsions of the GRP78 protein were prepared using COMPLETE ADJUVANT (DIFCO: DF263810) for priming and IMCOMPLETE ADJUVANT (DIFCO: DF263910) for booster; each of the emulsions was administered to three mice in the following groups [(MRL/pr, male, 4-wk old) (Balb/c, female, 6-wk old): all purchased from charles river, Japan] at 50 μg/mouse by subcutaneous injection to immunize them (TERUMO syringe 1 mL, 26 G needle). Two weeks after priming, the secondary immunization was effected and subsequent boosters were performed at one-week intervals to effect a total of 4 or 5 immunizations. For the final immunization, GRP78 (50 μg) was suspended in 100 μl of PBS and injected into the tail vein; three days later, cell fusion was practiced.

1-3. Constructing Hybridomas

Cell fusion was performed in the following manner. The spleen was asceptically extracted from each mouse and disintegrated in medium 1 (RPMI1640+PS) to form a suspension of single cells. The suspension was passed through a 70-elm nylon mesh (Falcon) to remove the fat tissue and the like before counting the number of cells. The obtained B cells were mixed with mouse myeloma cells (P3U1 cells) such that the ratio of their cell counts was approximately 2:1; 1 mL of 50% PEG (Roche, cat #: 783 641) was then added to effect cell fusion. The fused cells were suspended in medium 2 [RPMI1640+PS, 10% FCS, HAT (Sigma, H0262), 5% BM condimed H1 (Roche: #1088947)] and distributed in a suitable number (10) of 96-well plates in a volume of 200 μL/well and cultured at 37° C. One week later, the culture supernatant was used to screen the hybridomas.

Example 2

Screening for Anti-GRP78 Antibodies that Recognize GRP78 Localized on the Cell Membrane 2-1. ELISA Screening for GRP78 Binding Antibodies (Primary Screening)

To acquire anti-GRP78 antibodies localized on the cell surface, screening for GRP78 binding antibodies was first performed with ELISA.

An ELISA plate (NUNC) coated with 1 μg/ml of the GRP78 protein purified from E. coli was reacted with the culture supernatant of hybridomas and incubated for 1 hour. Thereafter, reaction with alkali phosphatase (AP) labeled anti-mouse IgG (ZYMED: #62-6622) was performed for 1 hour, followed by adding 1 mg/ml of a substrate (SIGMA: S0942-50TAB) to develop color. Using a plate reader (Bio-Rad), $OD_{405}$ measurement was effected to select ELISA-positive wells.

2-2. FACs Screening for Antibodies Against GRP78 Localized on the Cell Surface (Secondary Screening)

The culture supernatant in the wells that were found positive in the primary screening was subjected to FACS analysis for the reactivity with a prostate cancer cell line (DU145).

DU145 (obtained from ATCC) was serially cultured in EMEM (invitrogen) containing 10% FCS, 1 mM sodium pyruvate, and 0.1 mM NEAA. DU145 was stripped off with 1 mM EDTA/PBS, reacted with the culture supernatant of hybridomas, and incubated at 4° C. for 1 hour. Thereafter, an FITC-labeled anti-mouse IgG antibody (BECKMAN COULTER: PN IM0819) was added and incubated at 4° C. for 30 minutes. Thereafter, the activities of the respective culture supernatants of hybridomas for binding to the cell surface of DU145 were analyzed by FACS (Becton Dickinson).

2-3. Limiting Dilution

The wells that were found to have any slight activity for binding to DU145 cells in FACS analysis were selected and subjected to limiting dilution (LD) to make monoclones of the hybridomas in each well. Specifically, the number of cells in each well was counted and they were seeded in a 96-well plate to give a density of 3 cells/well. Culture was performed for about 10 days and the culture supernatant in the wells where colonies appeared was subjected to ELISA again and screened for antibody-producing monoclones, with the binding activity used as an index. This series of operations gave 6 clones of GRP78-binding antibody (GA-19 antibody, GA-20 antibody, GA-21 antibody, GA-23 antibody, GA-28 antibody, and GA-31 antibody).

2-4. Determination of Subtypes

The antibodies were subtyped using IsoStrip (Roche #1 493 027). For subtyping, the culture supernatant of hybridomas was used after 10-fold dilution with PBS(–).

The respective purified antibodies were subtyped as shown below.

TABLE 1

| Antibody | Subtype |
|---|---|
| GA-19 | G1 |
| GA-20 | M |
| GA-21 | G3 |
| GA-23 | G2a |
| GA-28 | G1 |
| GA-31 | G1 |

2-5. Purification of Antibodies

From 50 mL of the obtained culture supernatant of hybridomas in monoclones, the respective antibodies were purified; for GA-19 antibody, GA-23 antibody, GA-28 antibody, and GA-31 antibody, the supernatant was loaded on a Hi Trap Protein G HP 1 mL column (Amersham Biosciences #17-0404-01), and for GA-20 antibody and GA-21 antibody which were IgM and IgG3, the supernatant was loaded on an open column packed with 1 ml of Protein L-agarose (SIGMA). The supernatant of hybridomas was adsorbed at a flow rate 1 ml-min and, after washing with 20 mL of 20 mM phosphate buffer (pH 7.0), it was eluted with 3.5 mL of 0.1 M glycine-HCl (pH 2.7). The eluted fractions were recovered in 0.5-ml aliquots into Eppendorf tubes to which 1 M Tris-HCl (pH 9.0) was preliminarily added in 50-μL portions. After $OD_{280nm}$ measurement, the antibody containing fractions were collected and mixed with PBS(–) to make a total of 2.5 mL, followed by buffer replacement with PBS(–) on a PD-10 column (Amersham Biosciences #17-0851-01). Each of the purified antibodies was passed through a 0.22-μm filter (MILLIPORE #SLGV033RS) for making a detailed study of its properties in the following example.

Example 3

Analysis of GRP78 Antibodies 3-1. Western Blot Analysis

To confirm that the obtained antibodies would specifically bind to GRP78 (GST-GRP78) purified from E. coli and to GRP78 expressed in DU145 cells, western blot was performed.

In lane 1, samples of DU145 cells ($1 \times 10^6$ cells) lysed in 300 μl of a lysis buffer (0.5% NP40, 10 mM tris-HCl, 150 mM NaCl, 5 mM EDTA, pH 7.5) were applied, and in lane 2, GST fused GRP78 protein (0.1 ug) purified from E. coli was applied, and blotting was effected on a PVDF membrane in accordance with the usual procedure. The blots were reacted with the respective antibodies (2 μg/ml), then with a secondary antibody (HRP-labeled anti-mouse IgG), followed by protein detection with an ECL western blot detection reagent (GE Healthcare). As a result, it was confirmed that all the antibodies obtained specifically recognized not only the GST-fused GRP78 protein expressed in E. coli but also the GRP78 protein capable of exogenous expression in cells (FIG. 1).

3-2. FACs Analysis
3-2-1. Activity for Binding to the Cell Surface of Prostate Cancer Cell Line (DU145)

The respective purified anti-GRP78 antibodies were analyzed by FACS to see whether they would stain the cell surface of cancer cells.

DU145 cells stripped with 1 mM of EDTA were incubated with each of the antibodies (10 μg/ml) in an FACS buffer at 4° C. for 1 hour. Thereafter, an FITC-labeled anti-mouse IgG antibody (BECKMAN COULTER: PN IM0819) was added and the cells were incubated at 4° C. for 30 minutes. Thereafter, the activity for binding to GRP78 on the surface of DU145 cells was analyzed by FACS (Becton Dickinson).

Figure 2:
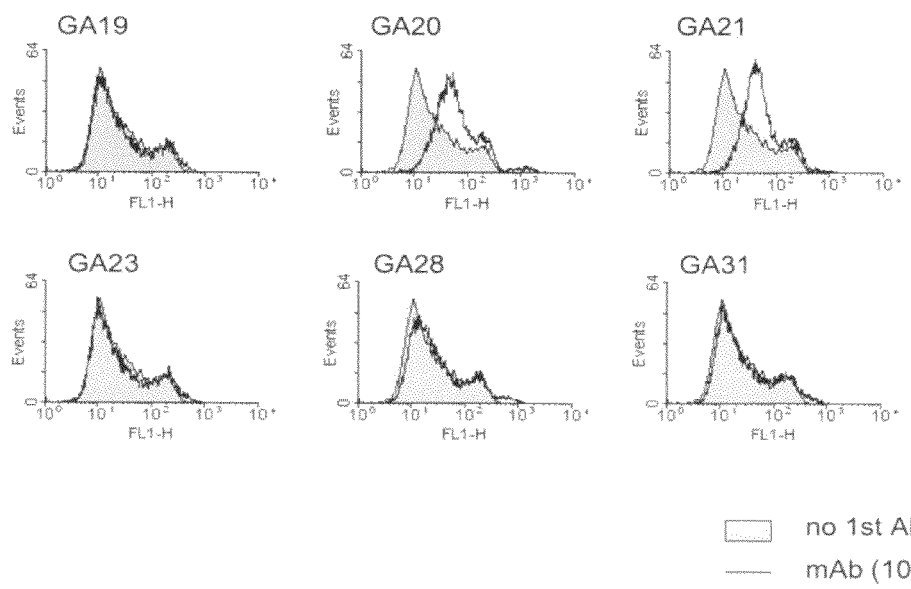
FIG. 2 is a set of diagrams showing the results of FACS analysis of the binding activities of the obtained anti-GRP78 antibodies to the cell surface of DU145 cell.

As a result, two of the obtained six clones of anti-GRP78 antiby (GA-20 antibody and GA-21 antibody) stained DU145 cells (FIG. 2).

It was thus confirmed that GA-20 antibody and GA-21 antibody recognized extracellular epitopes of the GRP78 molecule capable of expression in cancer cells.

The nucleotide sequence of the heavy-chain variable region of the GA-20 antibody is depicted in SEQ ID NO: 4, the amino acid sequence of that heavy-chain variable region is depicted in SEQ ID NO: 5, the nucleotide sequence of the light-chain variable region is depicted in SEQ ID NO: 6, and the amino acid sequence of that light-chain variable region is depicted in SEQ ID NO: 7. The amino acid sequence of CDR1 in the heavy-chain variable region of the GA-20 antibody is depicted in SEQ ID NO: 8, the amino acid sequence of CDR2 is depicted in SEQ ID NO: 9, the amino acid sequence of CDR3 is depicted in SEQ ID NO: 10, the amino acid sequence of CDR1 in the light-chain variable region is depicted in SEQ ID NO: 11, the amino acid sequence of CDR2 is depicted in SEQ ID NO: 12, and the amino acid sequence of CDR3 is depicted in SEQ ID NO: 13.

The nucleotide sequence of the heavy-chain variable region of the GA-21 antibody is depicted in SEQ ID NO: 14, the amino acid sequence of that heavy-chain variable region is depicted in SEQ ID NO: 15, the nucleotide sequence of the light-chain variable region is depicted in SEQ ID NO: 16, and the amino acid sequence of the light-chain variable region is depicted in SEQ ID NO: 17. The amino acid sequence of CDR1 in the heavy-chain variable region of the GA-21 antibody is depicted in SEQ ID NO: 18, the amino acid sequence of CDR2 is depicted in SEQ ID NO: 19, the amino acid sequence of CDR3 is depicted in SEQ ID NO: 20, the amino acid sequence of CDR1 in the light-chain variable region is depicted in SEQ ID NO: 21, the amino acid sequence of CDR2 is depicted in SEQ ID NO: 22, and the amino acid sequence of CDR3 is depicted in SEQ ID NO: 23.

3-2-2. Evaluation of FACs Binding Activity for Other Cancer Types

Figure 3:
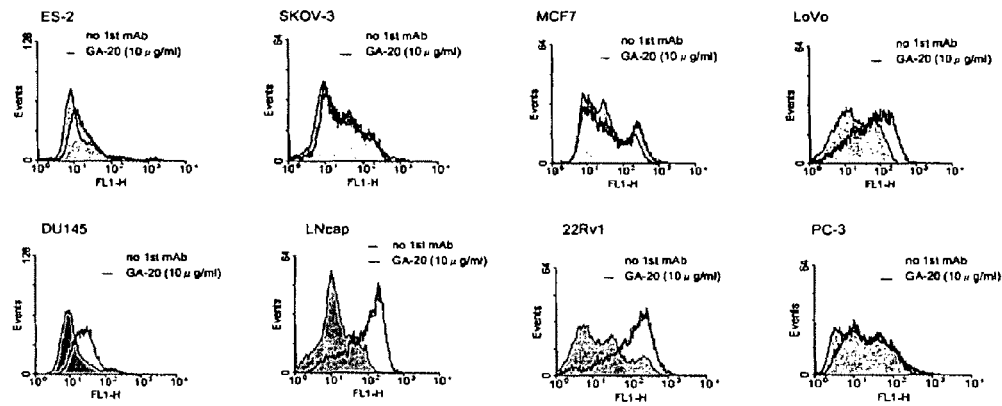
FIG. 3 is a set of diagrams showing the results of FACS analysis of the binding activities of the GA-20 antibody to the cell surface of various cancer cells.

In the next place, the GA-20 antibody capable of recognizing GRP78 localized on the cell surface was evaluated for its FACS reactivity with other cancer types. Ovary cancer cell lines (ES-2 and SKOV3), a breast cancer cell line (MCF7), a colon cancer cell line (LoVo), and prostate cancer cell lines (DU145, Lncap, 22Rv1 and PC3) were purchased from ATCC and cultured under the ATCC recommended culture conditions. These cells were stained with the GA-20 antibody (10 μg/ml) and subjected to FACS analysis in the above-described manner. As a result, it was confirmed that the GA-20 antibody stained not only DU145 but also other types of cancer cell such as LoVo, LNcap and 22Rv1 (FIG. 3).

3-2-3. Evaluation of FACs Binding Activity for Non-Cancer Cells

Figure 4:
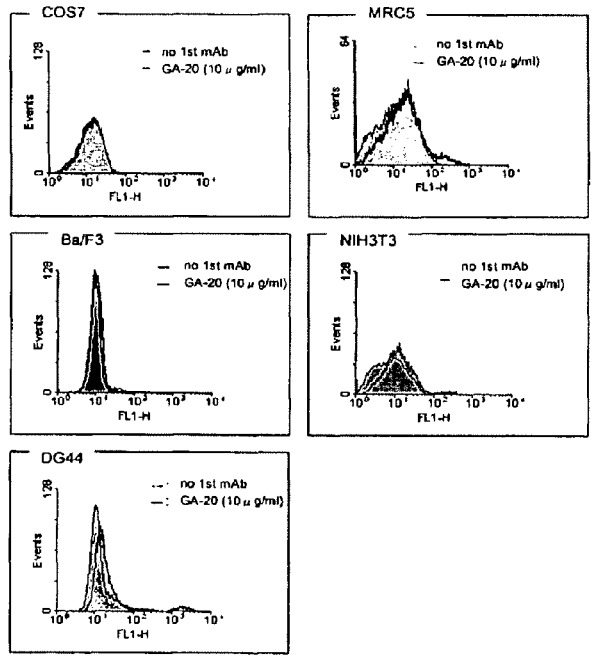
FIG. 4(A) is a set of diagrams showing the results of FACS analysis of the binding activities of the GA-20 antibody to the cell surface of various normal or immortalized cell lines.
FIG. 4(B) is a diagram showing the results of western blot analysis of the expression of the protein GRP78 in the various normal or immortalized cell lines using GA-20.
Figure 4:
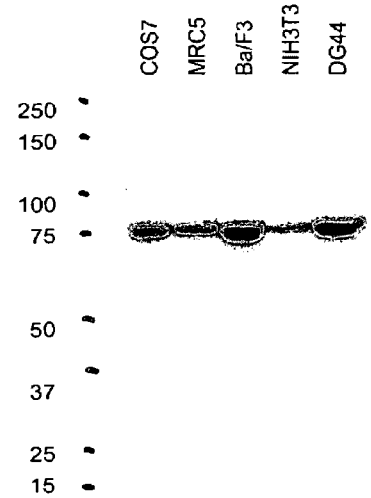

In the next place, the activity for FACS binding to cell lines other than cancer cells was analyzed. Monkey kidney cells (COS7), human normal fibroblast cells (MRC5), mouse pro-B cells (Ba/F3), mouse fibroblast cells (NIH3T3), and hamster ovary cells (DG44) were purchased from ATCC and cultured under the ATCC recommended culture conditions. These cells were stained with the GA-20 antibody (10 μg/ml) and subjected to FACS analysis. At the same time, the cells were lysed with an NP40 lysis buffer and subjected to western blot with the GA-20 antibody (2 μg/ml). As a result, those cells, although they all expressed GRP78 (FIG. 4B), were not stained with FACS (FIG. 4A). From this result, it was speculated that only certain types of cells such as cancer cells would express GRP78 and allow it be localized on the cell surface.

3-3. Analysis for Internalizing Activity
3-3-1. Analysis by FACS

To determine whether the anti-GRP78 recognizing antibodies that stained the cell surface (GA-20 antibody and GA-21 antibody) had an internalizing activity, the following experiment was conducted.

DU145 cells were stripped with 1 mM of EDTA and divided into two groups; the cells in one group were reacted with each antibody (10 μg/ml) in an FACS buffer (PBS containing 2% FCS and 0.05% NaN$_3$) at 0° C. for 2 hours, and the cells in the other group were incubated with each antibody (10 μg/ml) in a culture medium (RPMI1640 containing 10% FCS) at 37° C. for 2 hours. Thereafter, FACS analysis was performed with FITC-labeled mouse IgG to detect any antibodies that remained on the cell surface.

Figure 5:
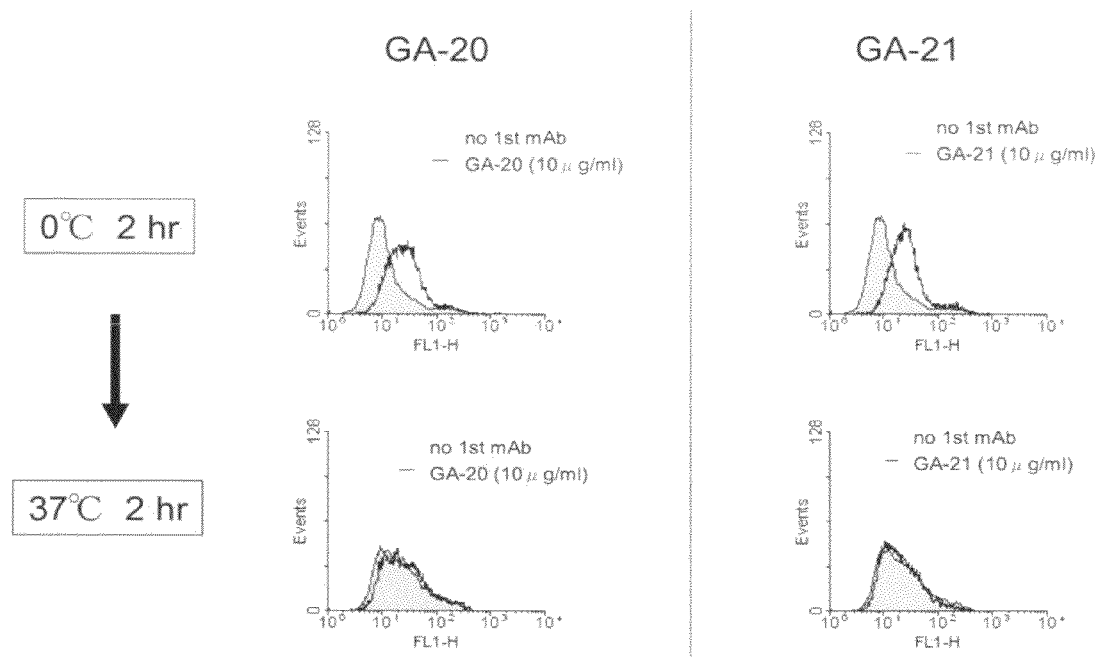
FIG. 5 is a set of diagrams showing the results of FACS analysis of the activities of the antibodies GA-20 and GA-21 for internalization into cells; each antibody was incubated with DU145 cells at 0° C. or 37° C. for 2 hours, followed by detecting with a secondary antibody (FITC labeled anti-mouse IgG antibody).

As a result, it was confirmed that either antibody had disappeared from the cell surface upon 2-hr reaction at 37° C. (FIG. 5).

3-3-2. Analysis by Immunocytostaining

To confirm that the phenomenon described above was not extracellular release of the antibodies, the following experiment was conducted. To DU145 cells being cultured in a dish, the GA-20 antibody or the GA-31 antibody (negative control, no binding activity to the cell surface) was added in 20 μg/ml and cultured at 37° C. for 3 hours. After washing with PBS, the cells were washed twice with a glycine buffer (0.1 M glycine, pH 2.7) to remove the antibodies binding to the cell surface. Thereafter, 4% paraformaldehyde was allowed to act on the cells at room temperature for 10 minutes to immobilize them and, subsequently, 0.1% Triton X100 was allowed to act at room temperature for 5 minutes. The cells were stained with FITC-labeled mouse IgG and the antibodies incorporated into the cells were examined with a fluorescence microscope (KEYENCE).

Figure 6:
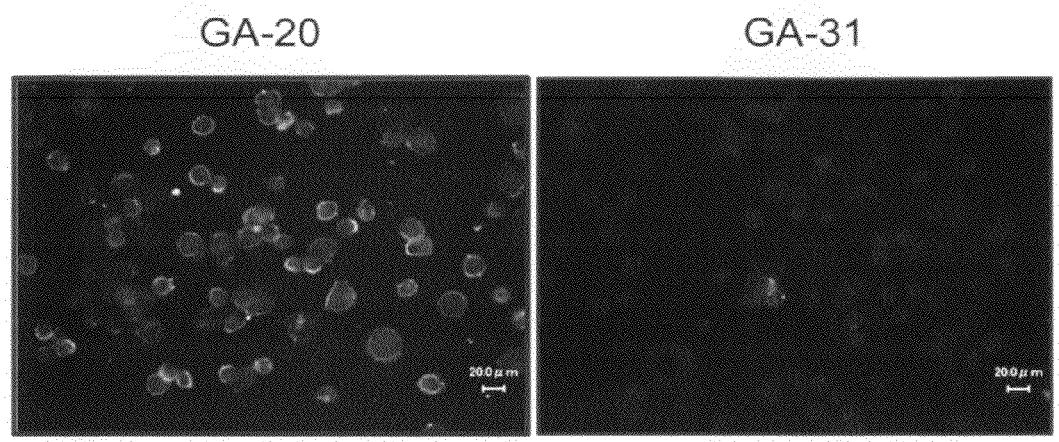
FIG. 6 is a set of diagrams showing the results of analysis conducted by immunocytostain to determine whether the two different anti-GRP78 antibodies (GA-20 and GA-31) would be incorporated into the cells; each antibody was added to DU145 cells under culture, and incubated for 3 hours at 37° C.; thereafter, the cells were treated in accordance with the scheme outlined below, and the antibodies incorporated into cells were analyzed.
Figure 6:
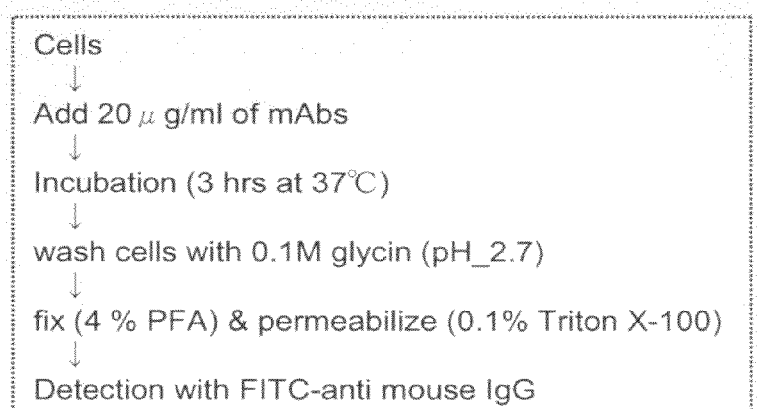

As a result, the GA-20 antibody having an activity for binding to the cell surface was detected within the cells but the GA-31 antibody not binding to the cell surface was not detected within the cells (FIG. 6). Thus, it was confirmed that the GA-20 antibody bound to the cell surface had been incorporated into the cells as the result of 3-hr culture at 37° C.

Example 4

Epitope Analysis 4-1. Preparation of GST-Fused Proteins for Epitope Mapping
4-1-1. Construction of Vectors for Expressing GST-Fused Proteins for Epitope Mapping As the first step in the process of identifying the epitopes of various antibodies, E. coli expression vector encoding each part of GRP78 fused to glutathione S-transferase (GST) protein was constructed as bellows.

4-1-1-1. Constructing a GST-GRP78-N (19-350) Expressing Vector

With pGEX-GRP78-full used as a template, and with GRP-GST-1 (SEQ ID NO: 28) as a sense primer and GRP-GST-3 (SEQ ID NO: 30) as an antisense primer, PCR was performed in 25 cycles, each consisting of 94° C. for 30 sec, 64° C. for 30 sec, and 72° C. for 120 sec, to give a cDNA fragment coding for GRP78 (amino acids 19-350) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78-N (19-350)).

4-1-1-2. Constructing a GST-GRP78-C (289-654) Expressing Vector

With pGEX-GRP78-full used as a template, and with GRP-GST-4 (SEQ ID NO: 31) as a sense primer and GRP-GST-2 (SEQ ID NO: 29) as an antisense primer, PCR was performed in 25 cycles, each consisting of 94° C. for 30 sec, 64° C. for 30 sec, and 72° C. for 120 sec, to give a cDNA fragment coding for GRP78 (amino acids 289-654) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78-C (289-654)).

4-1-1-3. Constructing a GST-GRP78-C (289-350) Expressing Vector

With pGEX-GRP78-full used as a template, and with GRP-GST-4 (SEQ ID NO: 31) as a sense primer and GRP-GST-3 (SEQ ID NO: 30) as an antisense primer, PCR was performed in 25 cycles, each consisting of 94° C. for 30 sec and 72° C. for 30 sec, to give a cDNA fragment coding for GRP78 (amino acids 289-350) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78-C (289-350)).

4-1-1-4. Constructing a GST-GRP78-C (289-445) Expressing Vector

With pGEX-GRP78-full used as a template, and with GRP-GST-4 (SEQ ID NO: 31) as a sense primer and GRP-GST-5 (SEQ ID NO: 32) as an antisense primer, PCR was performed in 25 cycles, each consisting of 94° C. for 30 sec and 72° C. for 30 sec, to give a cDNA fragment coding for GRP78 (amino acids 289-445) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78-C (289-445)).

4-1-1-5. Constructing a GST-GRP78-C (289-538) Expressing Vector Expressing Vector With pGEX-GRP78-full used as a template, and with GRP-GST-4 (SEQ ID NO: 31) as a sense primer and GRP-GST-6 (SEQ ID NO: 33) as an antisense primer, PCR was performed in 25 cycles, each consisting of 94° C. for 30 sec and 72° C. for 30 sec, to give a cDNA fragment coding for GRP78 (amino acids 289-538) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78-C (289-538)).

4-1-1-6. Constructing a GST-GRP78 (345-385) Expressing Vector

With pGEX-GRP78-full used as a template, and with GRP-GST-7 (SEQ ID NO: 34) as a sense primer and GRP-GST-8 (SEQ ID NO: 35) as an antisense primer, PCR was performed in 25 cycles, each consisting of 94° C. for 30 sec, 64° C. for 30 sec, and 72° C. for 30 sec, to give a cDNA fragment coding for GRP78 (amino acids 345-385) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78 (345-385)).

4-1-1-7. Constructing a GST-GRP78 (376-415) Expressing Vector

With pGEX-GRP78-full used as a template, and with GRP-GST-9 (SEQ ID NO: 36) as a sense primer and GRP-GST-10 (SEQ ID NO: 37) as an antisense primer, PCR was performed in 25 cycles, each consisting of 94° C. for 30 sec, 64° C. for 30 sec, and 72° C. for 30 sec, to give a cDNA fragment coding for GRP78 (amino acids 376-415) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78 (376-415)).

4-1-1-8. Constructing a GST-GRP78 (406-445) Expressing Vector

With pGEX-GRP78-full used as a template, and with GRP-GST-11 (SEQ ID NO: 38) as a sense primer and GRP-GST-5 (SEQ ID NO: 32) as an antisense primer, PCR was performed in 25 cycles, each consisting of 94° C. for 30 sec, 64° C. for 30 sec, and 72° C. for 30 sec, to give a cDNA fragment coding for GRP78 (amino acids 406-445) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78 (406-445)).

4-1-1-9. Constructing a GST-GRP78 (345-445) Expressing Vector

With pGEX-GRP78-full used as a template, and with GRP-GST-7 (SEQ ID NO: 34) as a sense primer and GRP-GST-5 (SEQ ID NO: 32) as an antisense primer, PCR was performed in 25 cycles, each consisting of 94° C. for 30 sec, 64° C. for 30 sec, and 72° C. for 30 sec, to give a cDNA fragment coding for GRP78 (amino acids 345-445) with BamHI and XhoI cleavage sequences attached to the 5' and 3' ends, respectively.

The fragment was cleaved with BamHI and XhoI and inserted downstream of the GST coding region of an *E. coli* expression vector (pGEX-6P-1) that had been similarly cleaved with BamHI and XhoI to construct a GRP78-GST fusion protein expressing vector (pGEX-GRP78 (345-445)).

The sequences of the primers used in constructing the various expression vectors are depicted below.

```
GRP-GST-1:
                                        (SEQ ID NO: 28)
aaaggatccg aggaggagga caagaaggag gacgtggg GRP-GST-2:
                                        (SEQ ID NO: 29)
tttctcgagc tacaactcat ctttttctgc tgtatcctc GRP-GST-3:
                                        (SEQ ID NO: 30)
tttctcgagc taatcagaat cttccaacac tttctggacg ggc GRP-GST-4:
                                        (SEQ ID NO: 31)
aaaggatccc ggcgcgaggt agaaaaggcc aaac GRP-GST-5:
                                        (SEQ ID NO: 32)
ttctcgagct aggtaggcac cactgtgttc cttgg GRP-GST-6:
                                        (SEQ ID NO: 33)
ttctcgagct agatttcttc aggtgtcagg cgatt GRP-GST-7:
                                        (SEQ ID NO: 34)
tttggatccg tgttggaaga ttctgatttg aaga GRP-GST-8:
                                        (SEQ ID NO: 35)
ttctcgagct aggatggttc cttgccattg aagaa GRP-GST-9:
                                        (SEQ ID NO: 36)
aaaggatcca aagagttctt caatggcaag ga GRP-GST-10:
                                        (SEQ ID NO: 37)
ttctcgagct ataccaggtc acctgtatct tgatc GRP-GST-11:
                                        (SEQ ID NO: 38)
aaaggatcct ctggtgatca agatacaggt gac
```

4-1-2. Inducing the Expression of the Respective GST Fused GRP78 Proteins

Using the thus constructed E. coli expression vectors, *E. coli* strain BL21 was transformed. The *E. coli* transformants were cultured in an LB medium (1 ml for each culture) and at the logarithmic growth stage, IPTG (final concentration: 1 mM) was added to induce protein expression. Four or five hours later, the *E. coli* cells were recovered and lysed in an SDS sample buffer (0.5 ml) to form a lysate; 5 µl of the lysate was taken and in accordance with the usual practice, it was subjected to SDS-PAGE and subsequently blotted on a PVDF membrane for use in western blotting.

4-2. Epitope Mapping of the Respective Antibodies

The thus prepared GST fused proteins representing the various regions of the GRP78 protein were subjected to western blotting to see which regions of the GRP78 protein would be recognized by the respective GRP78 antibodies obtained.

Figure 7:
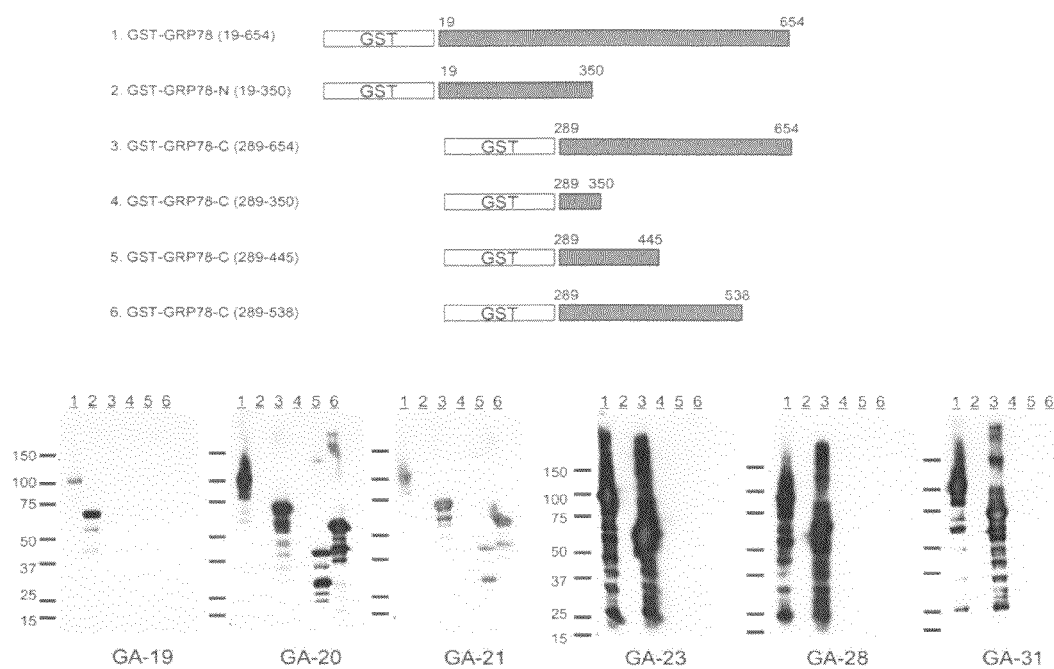
FIG. 7 is a set of diagrams showing the results of western blot analysis of the epitopes of respective anti-GRP78 antibodies; the upper panel shows schematically the GST fused truncated form of GRP78 proteins (1-6) used in epitope analysis, and the lower panel shows the results of western blot. Each recombinant GST protein fused to a truncated form of GRP78 (proteins (1-6)) expressed in E. coli were subjected to SDS-PAGE followed by immunoblotting with the respective anti-GRP78 antibodies as indicated.

The result of the first western blotting (FIG. 7) shows that GA-19 antibody, which did not stain cell surface by FACS, recognized half (19-350) of the GRP78 protein toward the N terminus, whereas GA-23 antibody, GA-28 antibody, and GA-31 antibody, which also showed inability to bind to cell surface, recognized the 538-654 region toward the C terminus.

In contrast, GA-20 antibody and GA-21 antibody that are capable of binding to cell surface by FACS were found, in view of their stain patterns in western blotting, to recognize a 350-445 region spanning nearly 100 amino acids.

Figure 8:
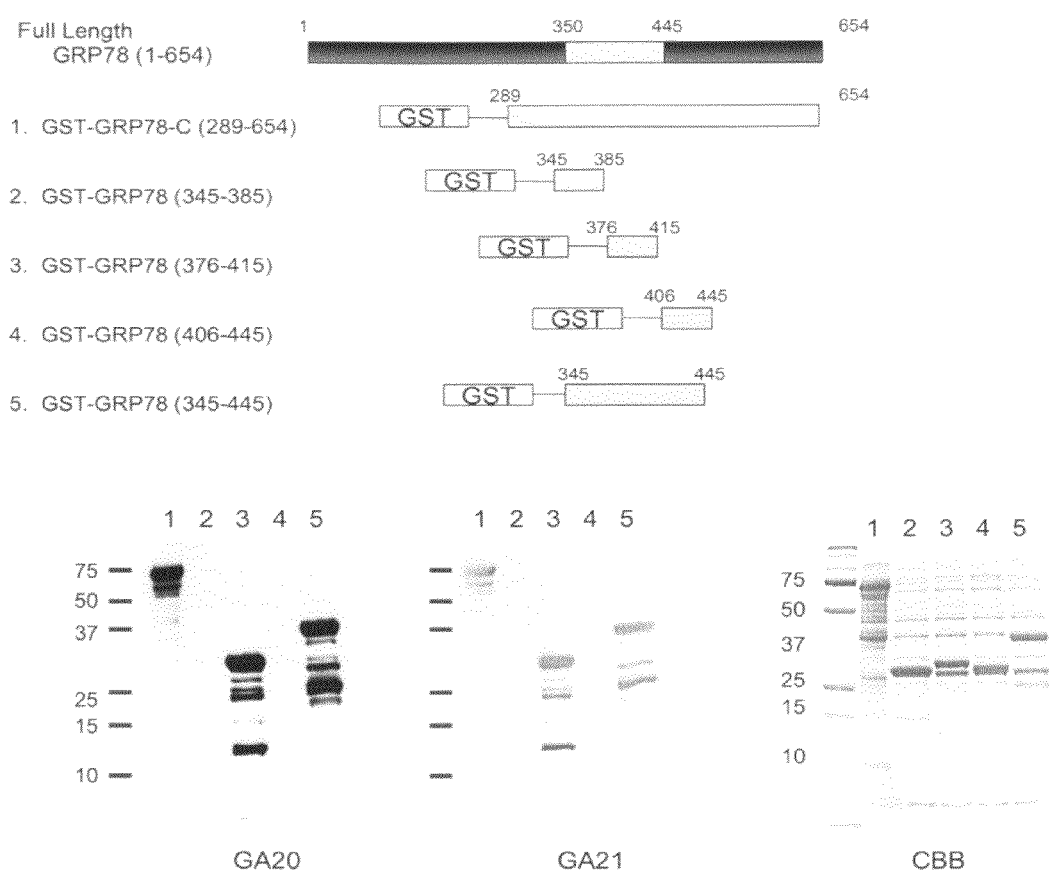
FIG. 8 is a set of diagrams showing the results of western blotting analysis carried out to narrow down the ranges of the epitopes of GA-20 and GA-21 within GRP78; the upper panel shows schematically the GST fused to GRP78 proteins as restricted to narrower ranges, and the lower panel shows the results of western blot. The respective GST fused GRP78 proteins (1-5) are subjected to SDS-PAGE followed by immunoblotting with GA-20 and GA-21 antibodies.

In the next place, GST fused proteins were constructed by dividing the 350-445 region into three areas and subjected to western blotting in the same manner as described above so as to identify the areas to which the GA-20 antibody and the GA-21 antibody would bind. As a result, the epitopes of these antibodies were found to be the 40 amino acids with amino acid numbers 376-415 in the GRP78 protein (FIG. 8).

Example 5

Constructing a Cell Death Inducer Using Extracellular Region Recognizing Anti-GRP78 Antibody (GA-20 Antibody)

5-1. Cloning the Variable Regions of GA-20 Antibody and Analyzing their Amino Acid Sequences Total RNA was purified from ca. $5 \times 10^6$ hybridomas using Trizol (#15596-018, Life technologies). From 1 µg of the total RNA obtained, full-length cDNA was synthesized using SMART RACE cDNA Amplification Kit (CLONTECH #PT3269-1) in accordance with the accompanying manual. With the obtained cDNA used as a template and using Advantage 2 PCR Enzyme System (CLONTECH #PT3281-1), PCR was performed under the following conditions to amplify the genes coding for the heavy-chain variable region (VH) and the light-chain variable region (VL) of the GA-20 antibody.

Primer for cloning the light-chain variable region
Universal primer mix (UPM) to k(VL-k)
UPM: Attached to the Kit

```
VL-k:
gct cac tgg atg gtg gga aga tg    (SEQ ID NO: 39)
```

Primer for cloning the heavy-chain variable region
UPM to VH-M
UPM: Attached to the Kit

```
VH-M:
cca cca gat tct tat cag aca gg    (SEQ ID NO: 40)
```

94° C.×5 sec and 72° C.×2 min, 5 cycles;
94° C.×5 sec, 70° C.×10 sec, and 72° C.×2 min, 5 cycles;
94° C.×5 sec, 68° C.×10 sec, and 72° C.×2 min, 27 cycles.

The gene fragments amplified by the above procedure were TA-cloned in pCRII-TOPO (Invitrogen TOPO TA-cloning kit, #45-0640) and, thereafter, the respective inserts were checked for their nucleotide sequences by an ABI3730 sequencer.

5-2. Constructing Toxin-Labeled GA-20-Single-Chain Fv Antibody (GA20_PE40)

5-2-1. Constructing a GA20_PE40 Expressing Vector 5-2-1-1. Constructing pET22b_-His_PE40

Based on the GA-20 antibody specifically recognizing GRP78 localized on the cell surface, an attempt was made to construct cell death inducing antibodies labeled with an immunotoxin (PE40).

First, an expression vector was constructed that coded for a toxin labeled antibody (GA20_PE40) having a toxin (PE40) attached to a single-chain Fv (scFv) derived from GA-20 antibody. The immunotoxin PE40 gene was amplified by PCR under the following conditions with plasmid DNA (pJH8) purchased from ATCC and used as a template.

Using a sense primer (PE-1) having an EcoRI recognition sequence and a linker sequence (18 amino acids) attached in that order to the 5' end and an antisense primer (PE-2) having a NotI recognition sequence, a termination codon, an ER transition signal sequence (KDEL) and a FLAG tag sequence attached in that order to the 5' end, PCR amplification was performed in a KOD-Plus buffer (2 mM dNTPs, 25 mM MgSO$_4$, and KOD-Plus) (Takara) under the following conditions:

98° C.×10 sec, 72° C.×5 sec, 68° C.×4 min, 5 cycles;
98° C.×10 sec, 70° C.×5 sec, 68° C.×4 min, 5 cycles;
98° C.×10 sec, 68° C.×4 sec, 25 cycles.

The primer sequences are as depicted below.

```
PE-1:
                                      (SEQ ID NO: 41)
taagaattcg gtggcgcgcc ggagttcccg aaaccgtcca ccccgccggg ttcttctggt ttagagggcg gcagcctggc cgcgctg PE-2:
                                      (SEQ ID NO: 42)
acttagcggc cgctcactac agttcgtctt tcttatcgtc gtcatccttg tagtccggcg gtttgccggg ctggc
```

The product amplified by PCR was inserted into pGEM-T easy using pGEM-T Easy Vector System I (Promega). The sequence of the product was confirmed by an ABI3730 sequencer.

In the next place, a His tag sequence, a HindIII recognition sequence, an EcoRI recognition sequence, and a NotI recognition sequence were inserted downstream of a PelB signal sequence in an *E. coli* expression vector pET22b vector (product of Novagen) to construct pET22b_His.

Then, the PE40 gene fragment cloned in pGEM-T easy was digested with EcoRI and NotI, and was sliced out of an agarose gel, followed by insertion of the resulting gene fragment between EcoRI and NotI in pET22b_His to construct pET22b_His_PE40.

5-2-1-2. Constructing pET22b_His_GA20scFv-PE40

A gene fragment coding for a single-chain Fv derived from the GA-20 antibody, namely, the heavy-chain variable region of the GA-20 antibody is ligated to its light-chain variable region by a linker sequence composed of 15 amino acids ((GlyGlyGlyGlySer)$_3$) (SEQ ID NO: 43), was amplified by performing PCR under the following conditions.

First, with the heavy-chain variable region of the GA-20 antibody being used as a template after it was TA-cloned in pCRII-TOPO, and using the sense primer GA20-1 (SEQ ID NO: 44) and the antisense primer GA20-2 (SEQ ID NO: 45) for the heavy-chain variable region while using the sense primer GA20-3 (SEQ ID NO: 46) and the antisense primer GA20-4 (SEQ ID NO: 47) for the light-chain variable region, PCR amplification was performed by carrying out a reaction with pyrobest DNA polymerase (TAKARA #R005) at 94° C. for one minute, followed by 25 cycles of 94° C. for 30 min and 72° C. for 30 min.

In the next place, the thus obtained PCR products of the heavy- and light-chain variable regions were purified on an S-300 HR column (Amersham Biosciences #27-5130-01); the respective products were mixed in 1 µl portions in the same tube and after performing a reaction with pyrobest DNA polymerase at 94° C. for one minute, an annealing reaction was carried out in 5 cycles of 94° C. for 30 min and 72° C. for 30 min.

After annealing, 1-µL of the reaction solution was subjected to PCR amplification using the primers GA20-1 (SEQ ID NO: 44) and GA20-4 (SEQ ID NO: 47) under the following conditions by first performing a reaction with pyrobest DNA polymerase at 94° C. for one minute, then repeating 25 cycles of 94° C. for 30 min and 72° C. for 1 min.

The amplified fragment was purified on an S-400 HR column (Amersham Biosciences #27-5140-01), cleaved with EcoRI-HindIII, and sliced out of an agarose gel. The sliced fragment was inserted between HindIII and EcoR in the pET22b_His_PE40 constructed in 5-2-1-1; following confirmation of its nucleotide sequence, pET22b_His_GA20scFv-PE40 was constructed.

The sequences of the primers used in PCR amplification are depicted below.

```
GA20-1:
                                      (SEQ ID NO: 44)
aaaagcttga ggtccagctg caacagtctg g GA20-2:
                                      (SEQ ID NO: 45)
cccgaaccac caccacccga accaccacca cctgaggaga cggtgactga ggttcc GA20-3:
                                      (SEQ ID NO: 46)
tggttcgggt ggtggtggtt cgggtggtgg cggatcggac attgtgatgt cacagtctcc atcct GA2-4:
                                      (SEQ ID NO: 47)
ttgaattctt tgatttccag cttggtgcct c
```

The nucleotide sequence of the obtained GA20-PE40 is depicted in SEQ ID NO: 24 and the amino acid sequence prescribed by that nucleotide sequence is depicted in SEQ ID NO: 25.

5-2-2. Purifying Toxin-Labeled GA-20_Single-Chain Fv Antibody (GA20-PE40)

*E. coli* strain BL21 transformed with pET22b_His_GA20scFv-PE40 was seeded in an LB agar plate containing 50 µg/ml of ampicilin. Grown single colonies were picked up and cultured in an LB medium (3 ml) containing 50 µg/ml of carbenicillin (COSMO BIO). After 4-hr culture, the grown cells were extended in 200 ml of an LB medium containing carbenicillin (50 µg/ml) and cultured continuously. When the growth reached a logarithmic stage, the culture medium was replaced by a new LB medium (200 ml, supplemented with carbenicillin) and IPTG (final 1 mM) was added to induce protein expression. After 5-hr culture, the cells were recovered by centrifugation.

In the presence of a protease inhibitor, Complete EDTA Free (Roche), the cells were suspended in 20 ml of B-BER (PIERCE) for lysis; subsequently, the insoluble proteins were removed by centrifugation to prepare a cell lysate. This sample of lysed cells was applied to a HisTrap column (HiTrap chelating HP 1 ml; Amersham Pharmacia) and GA20_PE40 was purified in accordance with the accompanying protocol. To be more specific, the proteins adsorbed on the column were washed with a binding buffer (20 mM sodium phosphate, 0.5 M NaCl, 10 mM imidazole, pH 7.4) and eluted with an elution buffer (20 mM sodium phosphate, 0.5 M NaCl, 500 mM imidazole, pH 7.4) to give a total of 7 fractions each weighing 500 µl.

To determine which of the eluted fractions contained the desired toxin-labeled GA20 antibody, they were subjected to ELISA assay, with the activity for binding to GRP78 being used as an index, for investigating the binding activities of the eluted fractions. ELISA was practiced in the following manner. To a plate (NUNC) coated with either GST-GRP78 purified from E. coli or a negative control HB-EGF protein (R&D) in an amount of 1 µg/ml, each of the fractions as diluted 40-fold with a diluent buffer (1% BSA, 50 mM Tris, 1 mM $MgCl_2$, 150 mM NaCl, 0.05% Tween 20) was added. After reaction at room temperature for 1 hour, the plate was washed three times with TBS-T (TBS-0.05% Tween 20) and an anti-flag antibody (M2 antibody, Sigma) was added in an amount of 1 µg/ml, followed by incubation at room temperature for 1 hour. After three additional washings with TBS-T, reaction with an alkali phosphatase-labeled anti-mouse IgG (ZYMED) was conducted for 1 hour and a substrate (Sigma) was added in an amount of 1 mg/ml to develop color.

Figure 9:
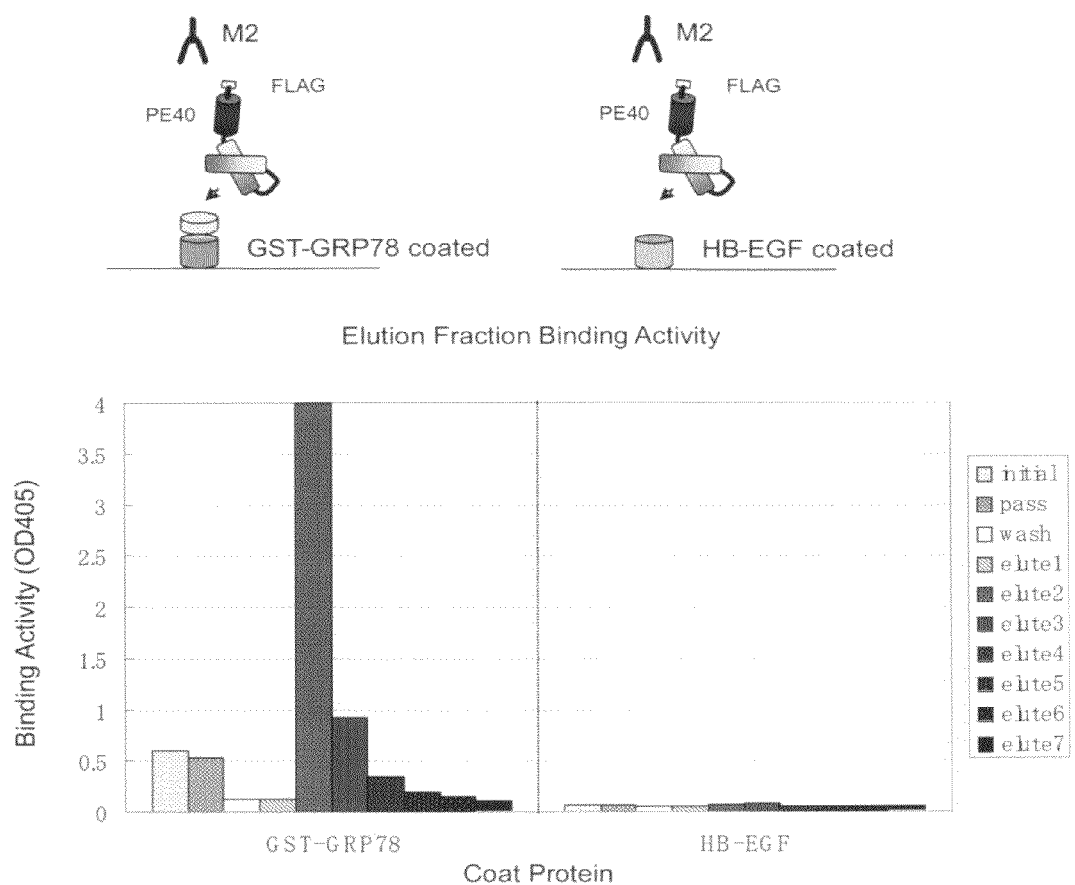
FIG. 9 shows the results of an analysis to detect a toxin-labeled GA-20 scFv antibody (GA20-PE40) in eluted fractions during HisTrap column purification, by an ELISA system using the GRP78 binding activity as a marker; the upper panel shows schematically the ELISA system for detecting the GRP78 binding activity of GA20-PE40, and the lower panel shows the binding activities of the eluted fractions obtained as the result of ELISA; "INITIAL" refers to the E. coli lysate induced to express GA20-PE40; "pass" refers to the fraction of the lysate that simply passed through a HisTrap column after it was applied to the column; "wash" refers to the wash fraction from the column; and "elute 1" to "elute 7" refer to the fractions eluted from the column.

As a result, binding activity specific for GRP78 was recognized in eluted fractions 2 and 3 (elutes 2 and 3), confirming the enrichment of GA20-PE40 protein in elutes 2 and 3 (FIG. 9, lower panel).

Hence, elutes 2, 3 and 4 were loaded on a PD-10 column (GE Healthcare) for buffer replacement by PBS in accordance with the accompanying instruction manual. The elutes were then passed through a 0.22-µm filter (Millipore) for sterilization and subjected to a study of cytotoxic activity.

5-3. Analyzing the Antitumor Activity of the Toxin-Labeled Anti-GRP78 Antibody (GA20-PE40)

The GA20-PE40 obtained was analyzed for cell death inducing activity.

Hamseter ovary cell line DG44 and prostate cancer cell lines DU145 and 22Rv1 were seeded in amounts of 90 µl/well on 96-well plates ($1\times10^3$/well for DG44, and $6\times10^3$/well for DU145 and 22Rv1). On the next day, GA20-PE40 fractions (elutes 2, 3, and 4) and PBS were added to the plates in amounts of 10 µl/well, and culture was performed at 37° C. Five days later, viable cell counts were taken with the reagent WST-8 (DOJINDO LABORATORIES) and compared with the data for the control (PBS treated group); the results were numerically represented in graphs.

Figure 10:
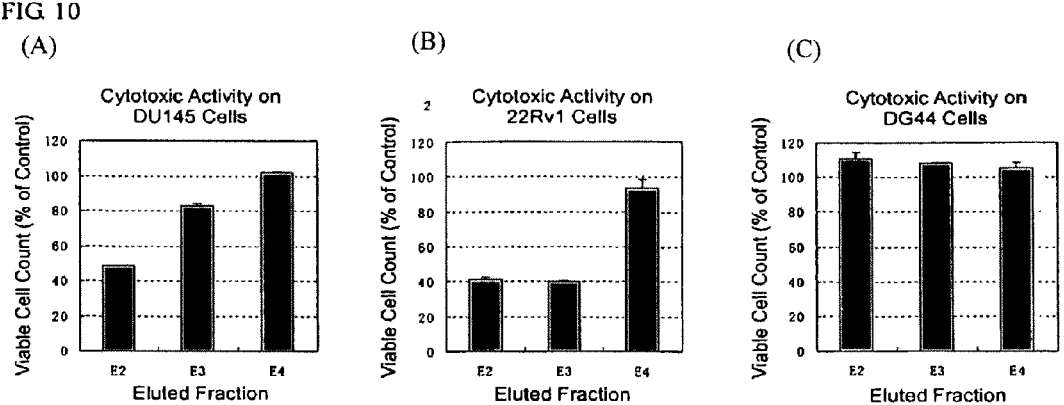
FIG. 10 is a set of digrams showing the cytotoxic activities of purified GA20-PE40 against DU145 cells (FIG. 10A), 22Rv1 cells (FIG. 10B), and DG44 cells (FIG. 10C); to each type of cells, eluted fractions (elutes 2, 3 or 4) were added at a concentration of 10% and, thereafter, the number of viable cells was counted and compared with the cell count in a PBS treated group to determine their percentage.

As it turned out, the cell growth of DG44 was not at all affected by GA20-PE40 (FIG. 10C); on the other hand, elutes 2 and 3 which were found to be active for binding to GRP78 were recognized to have cytotoxic activity in the two prostate cancer cell lines (DU145 and 22Rv1) (FIG. 10A for DU145 and FIG. 10B for 22Rv1).

These results revealed that the antibody against the extracellular epitope (350-445) of GRP78 is useful as an antitumor agent.

Example 6

Acquisition of Anti-GRP78 Antibodies by Re-immunization 6-1. Preparation of Immunogen GST-GRP78 (376-415) Protein From the foregoing analyses described in Example 4, it was speculated that the $376^{th}$ to $415^{th}$ amino acids in the GRP78 protein would form an extracellular region of GRP78. Hence, the present inventor re-immunized that region in an attempt to establish antibodies having strong enough affinity to recognize the extracellular region of GRP78.

First, E. Coli (BL21) cells transformed with the GST-GRP78 (376-415) expressing vector (pGEX-GRP78 (376-415)) described in Example 4 were cultured in an LB medium (250 ml) and when an $OD_{610}$ value of at least was reached, induction of protein expression was effected by means of IPTG (1 mM). After 5-hr culture, the E. coli cells were harvested and lysed in 25 ml of B-PER (PIERCE). The E. coli lysate was then diluted 10-fold with PBS; to the diluted lysate, PBS-equilibrated glutathione Sepharose 4B (Amersham Pharmacia) was added, followed by incubation at 4° C. overnight. Thereafter, the glutathione Sepharose 4B was washed with PBS several times to remove any unadsorbed proteins and the desired protein was eluted with 20 mM glutathione.

The eluted fractions were subjected to SDS-PAGE and stained with CBB to collect the fractions containing the desired protein. The sample was further separated from impure proteins in PBS by gel filtration chromatography (Superdex 200 16/60, GE Healthcare) and only the desired protein was purified to higher purity. The purified protein was used as an immunogen in the following experiment.

6-2. Immunization of GST-GRP78 (376-415) Protein

The GST-GRP78 (376-415) purified in 6-1 was applied by the same technique as used in Example 1 (1-2) to immunize mice in the following groups [(MRL/lpr, male, 4-wk old) (Balb/c, female, 6-wk old): all purchased from charles river, Japan]. Hybridomas were constructed as described in Example 1 (1-3).

6-3. Screening for Anti-GRP78 Antibodies 6-3-1. Purification of MBP-GRP78 (376-415) Protein A fusion protein (MBP-GRP78 (376-415)) was prepared from GRP78 ($376^{th}$ to $415^{th}$ amino acids) and a maltose binding protein (MBP) in the following manner.

The pGEX-GRP78 (376-415) constructed in Example 4 was cleaved with BamHI-SalI to slice a gene fragment coding for GRP78 (376-415). The fragment was inserted between BamHI and SalI in pMAL-c2X (New England BioLabs) to construct the MBP-GRP78 (376-415) expressing vector pMAL-c2X-GRP78 (376-415).

In the next place, E. coli strain BL21 transformed with this vector was cultured in an LB medium (250 ml) and when an $OD_{610}$ value of at least 0.5 was reached, IPTG (1 mM) was used to induce protein expression. After 5-hr culture, the E. coli cells were harvested by centrifugation and lysed with 25 ml of B-PER (PIERCE). Then, the E. coli lysate was diluted 5-fold with a column buffer (20 mM Tris, pH 7.5, 200 mM NaCl, 1 mM EDTA); to the diluted lysate, an amylose resin (New England BioLabs) equilibrated with the column buffer was added and incubated at 4° C. overnight. Subsequently, the amylose resin was washed with the column buffer several times to remove any unadsorbed proteins, and the desired protein was eluted with an elution buffer (the column buffer containing 10 mM maltose). The eluted fractions were subjected to SDS-PAGE and the fractions containing the desired protein were identified by CBB stain, combined into one fraction, and loaded on a PD10 column to effect buffer replacement with PBS. The thus purified MBP-GRP78 (376-415) was used in the following experiment as a sample for ELISA screening for binding antibodies.

6-3-2. Elisa Screening for GRP78 Binding Antibodies (Primary Screening)

An ELISA plate coated with 1 µg/ml of the MBP-GRP78 (376-415) purified in 6-3-1 was used to screen for antibodies that would bind to the region consisting of the $376^{th}$ to $415^{th}$ amino acids in the GRP78 protein.

The screening method was as described in Example 2 (2-1). The GRP78 binding antibodies obtained by primary screening, with the activity for binding to the MBP-GRP78 (376-415) protein used as an index, were subjected to subsequent secondary screening, as described below.

6-3-3. FACs Screening for Anti-GRP78 Antibodies Localized on the Cell Surface (Secondary Screening)

The GRP78 binding antibodies obtained by the primary screening were then subjected to secondary screening, with the activity for binding to prostate cancer cell lines (DU145 and 22Rv1 (ATCC CRL-2505)) being used as an index. The method was as described in Example 2 (2-2).

As a result, four additional antibodies, GC-18 antibody, GC-20 antibody, GD-4 antibody, and GD-17 antibody, were found to be capable of staining the prostate cancer cell lines by FACS.

These antibodies were subjected to limiting dilution by the method described in Example 2 (2-3) to form monoclones. The antibodies were subtyped by the method described in Example 2 (2-4). The subtypes of the respective antibodies are as shown below.

TABLE 2

| Antibody | Subtype |
|---|---|
| GC-18 | G1 |
| GC-20 | G1 |
| GD-4 | G1 |
| GD-17 | G1 |

Subsequently, the antibodies were purified by the method described in Example 2 (2-5), and analyzed for their properties in detail as follows.

6-4. Analyzing the Additional Antibodies Obtained by Re-Immunization 6-4-1. FACs Analysis To confirm that the purified four antibodies would stain cell surfaces of cancer cells, FACS analysis was carried out using a prostate cancer cell line (22Rv1). The cells were stained with each antibody (10 μg/ml) and subjected to FACS analysis by the method described in Example 3 (3-2-1).

Figure 11:
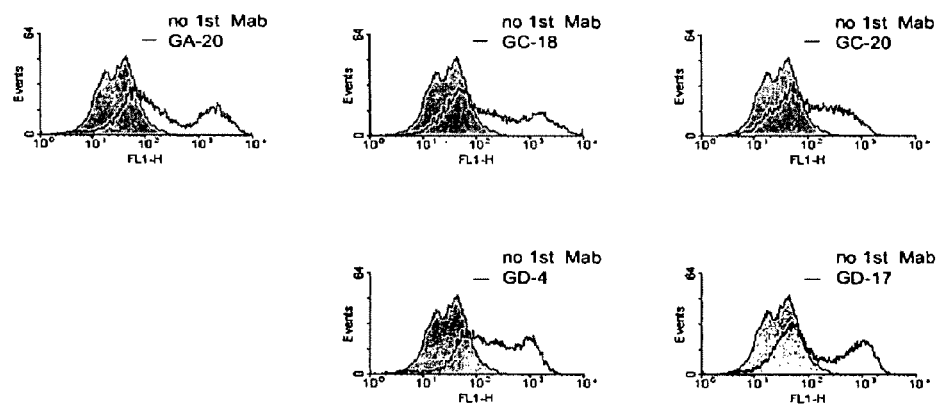
FIG. 11 is a set of digrams showing the results of FACS analysis of the binding activities of the obtained anti-GRP78 antibody for the cell surface of 22Rv1 cells.

As a result, all those antibodies were confirmed to bind to cell surfaces of 22Rv1 cells (FIG. 11).

6-4-2. Epitope Mapping

Since the four antibodies obtained above were established by immunizing the GST-GRP78 (376-415) protein, they are antibodies that recognize the partial region between the $376^{th}$ and $415^{th}$ amino acids in GRP78. Thus, this region was further divided into four areas, namely, the $376^{th}$ to $391^{st}$ amino acids (i.e., amino acids 1-16 in SEQ ID NO: 3), the $384^{th}$ to $399^{th}$ amino acids (i.e., amino acids 9-24 in SEQ ID NO: 3), the $392^{nd}$ to $407^{th}$ amino acids (i.e., amino acids 17-32 in SEQ ID NO: 3), and the $400^{th}$ to $415^{th}$ amino acids (i.e., amino acids 25-40 in SEQ ID NO: 3), and an analysis was made to see which part of the sequence composed by the $376^{th}$ to $415^{th}$ amino acids in GRP78 was recognized by each of those four antibodies.

6-4-2-1. Preparing GST Fused Proteins for Epitope Mapping
6-4-2-1-1. Constructing Vectors for Expressing the GST Fused Proteins for Epitope Mapping DNA fragments coding for the $376^{th}$ to $391^{st}$ amino acids, $384^{th}$ to $399^{th}$ amino acids, $392^{nd}$ to $407^{th}$ amino acids, and the $400^{th}$ to $415^{th}$ amino acids, respectively, in the GRP78 protein were constructed in the following manner.

A DNA fragment coding for GRP78 (376-391) (i.e., amino acids 1-16 in SEQ ID NO: 3) was constructed by annealing the oligomers GEP1/GEP2 (as depicted in SEQ ID NOS:48 and 49, respectively), a DNA fragment coding for GRP78 (384-399) (i.e., amino acids 9-24 in SEQ ID NO: 3) was constructed by annealing the oligomers GEP3/GEP4 (as depicted in SEQ ID NOS:50 and 51, respectively), a DNA fragment coding for GRP78 (392-407 (i.e., amino acids 17-32 in SEQ ID NO: 3) was constructed by annealing the oligomers GEP5/GEP6 (as depicted in SEQ ID NOS:52 and 53, respectively), and a DNA fragment coding for GRP78 (400-415) (i.e., amino acids 25-40 in SEQ ID NO: 3) was constructed by annealing the oligomers GEP7/GEP8 (as depicted in SEQ ID NOS:54 and 55, respectively).

The sequences of the oligomers used to construct those DNA fragments are shown below.

```
GEP1:
                                         (SEQ ID NO: 48)
gatccaaaga gttcttcaat ggcaaggaac catcccgtgg cataaaccca gatc GEP2:
                                         (SEQ ID NO: 49)
tcgagatctg ggtttatgcc acgggatggt tccttgccat tgaagaactc tttg GEP3:
                                         (SEQ ID NO: 50)
gatccccatc ccgtggcata aacccagatg aagctgtagc gtatggtgct gctc GEP4:
                                         (SEQ ID NO: 51)
tcgagagcag caccatacgc tacagcttca tctgggttta tgccacggga tggg GEP5:
                                         (SEQ ID NO: 52)
gatccgaagc tgtagcgtat ggtgctgctg tccaggctgg tgtgctctct ggtc GEP6:
                                         (SEQ ID NO: 53)
tcgagaccag agagcacacc agcctggaca gcagcaccat acgctacagc ttcg GEP7:
                                         (SEQ ID NO: 54)
gatccgtcca ggctggtgtg ctctctggtg atcaagatac aggtgacctg gtac GEP8:
                                         (SEQ ID NO: 55)
tcgagtacca ggtcacctgt atcttgatca ccagagagca caccagcctg gacg
```

Each of the DNA fragments thus constructed was inserted downstream of the GST coding region of an *E. coli* expression vector (pGEX-6P-1) cleaved with BamHI and XhoI, thereby constructing GRP78-GST fused protein expressing vectors (respectively designated pGEX-GRP78 (376-391), pGEX-GRP78 (384-399), pGEX-GRP78 (392-407), and Pgex-GRP78 (400-415)).

6-4-2-1-2. Inducing the Expression of the Respective GST Fused GRP78 Proteins

Figure 12:
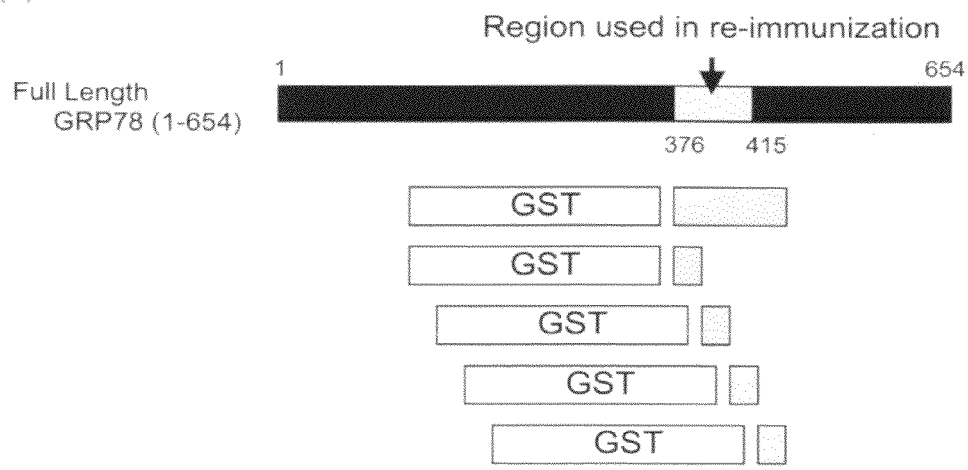
FIG. 12(A) shows schematically the GST fused GRP78 proteins used for epitope analysis on the GA-20 antibody, as well as four additional antibodies obtained by re-immunization (antibodies GC-18, GC-20, GD-4, and GD-17)
FIG. 12(B) shows the results of SDS-PAGE and CBB staining as performed to confirm that expression of the respective GST fused GRP78 proteins was induced in E. coli by IPTG supplementation.
Figure 12:
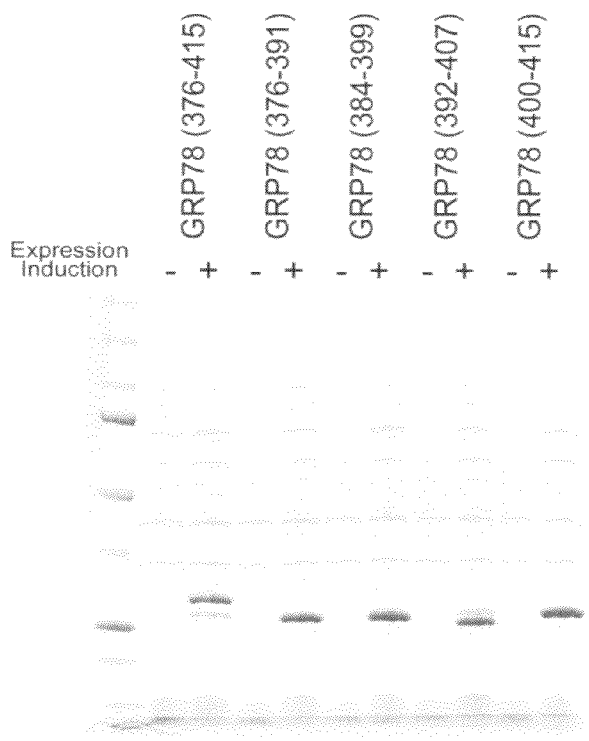

The thus constructed *E. coli* expression vectors were used to transform *E. coli* strain BL21 and protein expression was inducted by the method described in Example 4 (4-1-2). As a result, it was confirmed that the desired protein was expressed in *E. coli*, as shown in FIG. 12B. Hence, this protein was used in epitope mapping as follows.

6-4-2-2. Epitope Mapping of the Respective Antibodies

The thus prepared GST fused proteins were subjected to western blotting to see which regions of the GRP78 protein would be recognized by the respective GRP78 antibodies obtained.

Figure 13:
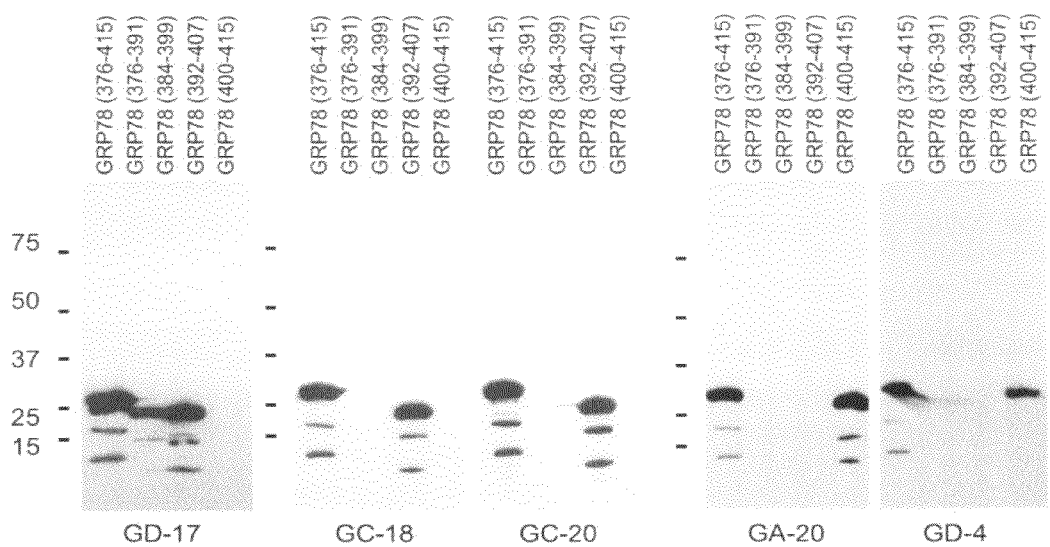
FIG. 13 is a set of diagrams showing the results of western blot analysis of the epitopes of various antibodies, in which various GST fused GRP78 proteins were subjected to SDS-PAGE for analyzing the reactivities of the respective antibodies; the table at the bottom lists the epitopes of the respective antibodies as identified from the results of western blotting analysis.

The stain patterns of western blot (FIG. 13) revealed that the GD-17 antibody recognized the region spanning the $384^{th}$ to $391^{st}$ amino acids in GRP78, the GC-18 and GC-20 antibodies recognized the region spanning the $392^{nd}$ to $407^{th}$ amino acids, and the GD-4 antibody recognized the region of the $400^{th}$ to $415^{th}$ amino acids. It was also found that the GA-20 antibody obtained at the earlier stage recognized the same region as the GD-4 antibody (FIG. 13).

6-4-3. Cloning the Variable Regions and Determining their Amino Acid Sequences

The variable regions of the additionally obtained antibodies (GC-18 antibody, GC-20 antibody, GD-4 antibody, and GD-17 antibody) were cloned and analyzed for their amino acid sequences by the methods described in Example 5 (5-1). It should, however, be noted that since all those antibodies were IgG$_1$, the variable regions of their heavy chains were cloned using the following VH-G1 primer (SEQ ID NO: 56):

VH-G1: cca cca gat tct tat cag aca gg (SEQ ID NO: 56)

The amplified light-chain and heavy-chain gene fragments were TA-cloned in pCRII-TOPO (Invitrogen TOPO TA-cloning kit, #45-0640) and, thereafter, the respective inserts were checked for their nucleotide sequences.

The nucleotide sequence of the heavy-chain variable region of the GC-18 antibody binding to the region spanning the $392^{nd}$ to $407^{th}$ amino acids in GRP78 is depicted in SEQ ID NO: 57, the amino acid sequence of that heavy-chain variable region is depicted in SEQ ID NO: 58, the nucleotide sequence of the light-chain variable region is depicted in SEQ ID NO: 59, and the amino acid sequence of that light-chain variable region is depicted in SEQ ID NO: 60. The amino acid sequence of CDR1 in the heavy-chain variable region of the GC-18 antibody is depicted in SEQ ID NO: 61, the amino acid sequence of CDR2 is depicted in SEQ ID NO: 62, the amino acid sequence of CDR3 is depicted in SEQ ID NO: 63, the amino acid sequence of CDR1 in the light-chain variable region is depicted in SEQ ID NO: 64, the amino acid sequence of CDR2 is depicted in SEQ ID NO: 65, and the amino acid sequence of CDR3 is depicted in SEQ ID NO: 66.

The nucleotide sequence of the heavy-chain variable region of the GC-20 antibody binding to the region spanning the $392^{nd}$ to $407^{th}$ amino acids in GRP78 is depicted in SEQ ID NO: 67, the amino acid sequence of that heavy-chain variable region is depicted in SEQ ID NO: 68, the nucleotide sequence of the light-chain variable region is depicted in SEQ ID NO: 69, and the amino acid sequence of that light-chain variable region is depicted in SEQ ID NO: 70. The amino acid sequence of CDR1 in the heavy-chain variable region of the GC-20 antibody is depicted in SEQ ID NO: 71, the amino acid sequence of CDR2 is depicted in SEQ ID NO: 72, the amino acid sequence of CDR3 is depicted in SEQ ID NO: 73, the amino acid sequence of CDR1 in the light-chain variable region is depicted in SEQ ID NO: 74, the amino acid sequence of CDR2 is depicted in SEQ ID NO: 75, and the amino acid sequence of CDR3 is depicted in SEQ ID NO: 76.

The nucleotide sequence of the heavy-chain variable region of the GD-4 antibody binding to the region of the $400^{th}$ to $415^{th}$ amino acids in GRP78 is depicted in SEQ ID NO: 77, the amino acid sequence of that heavy-chain variable region is depicted in SEQ ID NO: 78, the nucleotide sequence of the light-chain variable region is depicted in SEQ ID NO: 79, and the amino acid sequence of that heavy-chain variable region is depicted in SEQ ID NO: 80. The amino acid sequence of CDR1 in the heavy-chain variable region of the GD-4 antibody is depicted in SEQ ID NO: 81, the amino acid sequence of CDR2 is depicted in SEQ ID NO: 82, the amino acid sequence of CDR3 is depicted in SEQ ID NO: 83, the amino acid sequence of CDR1 in the light-chain variable region is depicted in SEQ ID NO: 84, the amino acid sequence of CDR2 is depicted in SEQ ID NO: 85, and the amino acid sequence of CDR3 is depicted in SEQ ID NO: 86.

The nucleotide sequence of the heavy-chain variable region of the GD-17 antibody binding to the region spanning the $384^{th}$ to $391^{st}$ amino acids in GRP78 is depicted in SEQ ID NO: 87, the amino acid sequence of that heavy-chain variable region is depicted in SEQ ID NO: 88, the nucleotide sequence of the light-chain variable region is depicted in SEQ ID NO: 89, and the amino acid sequence of that light-chain variable region is depicted in SEQ ID NO: 90. The amino acid sequence CDR1 in the heavy-chain variable region of the GD-17 antibody is depicted in SEQ ID NO: 91, the amino acid sequence of CDR2 is depicted in SEQ ID NO: 92, the amino acid sequence of CDR3 is depicted in SEQ ID NO: 93, the amino acid sequence of CDR1 in the light-chain variable region is depicted in SEQ ID NO: 94, the amino acid sequence of CDR2 is depicted in SEQ ID NO: 95, and the amino acid sequence of CDR3 is depicted in SEQ ID NO: 96.

Example 7

Analyzing the Drug Efficacy of Toxin-Labeled GD17 Single-Chain Antibody (GA17_scFv-PE40)

7-1. Constructing GD17_scFv-PE40 Expression Vector

A gene fragment coding for a single-chain Fv derived from the GD-17 antibody, namely, the heavy-chain variable region of the GD-17 antibody as ligated to its light-chain variable region by a linker sequence composed of 15 amino acids ((GlyGlyGlyGlySer)$_3$) (SEQ ID NO: 43), was amplified by performing PCR under the following conditions.

First, with the heavy-chain variable region of the GD-17 antibody being used as a template after it was TA-cloned in pCRII-TOPO, and using the sense primer GD17-1 (SEQ ID NO: 97) and the antisense primer GD17-2 (SEQ ID NO: 98) for the heavy-chain variable region while using the sense primer GD17-3 (SEQ ID NO: 99) and the antisense primer GD17-4 (SEQ ID NO: 100) for the light-chain variable region, PCR amplification was performed by carrying out a reaction with pyrobest DNA polymerase (TAKARA#R005) at 94° C. for one minute, followed by 25 cycles of 94° C.×30 min and 72° C.×30 min.

In the next place, the thus obtained PCR products of the heavy- and light-chain variable regions were purified on an S-300 HR column (Amersham Biosciences #27-5130-01); the respective products were mixed in 1 µl portions in the same tube and after performing a reaction with pyrobest DNA polymerase at 94° C. for one minute, an annealing reaction was carried out in 5 cycles of 94° C.×30 min and 72° C.×30 min.

After annealing, 1-µL of the reaction solution was subjected to PCR amplification using the primers GD17-1 (SEQ ID NO: 97) and GD17-4 (SEQ ID NO: 100) under the following conditions by first performing a reaction with pyrobest DNA polymerase at 94° C. for one minute, then repeating 25 cycles of 94° C.×30 min and 72° C.×1 min.

The amplified fragment was purified on an S-400 HR column (Amersham Biosciences #27-5140-01), cleaved with EcoRI-HindIII, and sliced out of an agarose gel. The sliced fragment was inserted between HindIII and EcoR in the pET22b_His_PE40 constructed in Example 5 (5-2-1-1); following confirmation of its nucleotide sequence, pET22b_His_GD17scFv-PE40 was constructed.

The sequences of the primers used in PCR amplification are shown below.

```
GD17-1:
                                    (SEQ ID NO: 97)
aaaagcttca ggttcagctc cagcagtctg g GD17-2:
                                    (SEQ ID NO: 98)
cccgaaccac caccacccga accaccacca cctgaggaga ctgtgagagt ggtgcct GD17-3:
                                    (SEQ ID NO: 99)
tggttcgggt ggtggtggtt cgggtggtgg cggatcggat gttgtgatga cccaaactcc ac GD17-4:
                                    (SEQ ID NO: 100)
ttgaattctt tcagctccag cttggtccc
```

The nucleotide sequence of the obtained GD17scFv_PE40 is depicted in SEQ ID NO: 101 and the amino acid sequence prescribed by that nucleotide sequence is depicted in SEQ ID NO: 102.

7-2. Mass Purification of Toxin-Labeled Single-Chain Antibody

E. coli strain BL21 transformed with pET22b_His_GD17scFv-PE40 was cultured in an LB medium containing carbenicillin (50 μg/ml). When the growth reached a logarithmic stage, IPTG (final dose, 1 mM) was added and culture was effected at room temperature (24° C.) overnight to induce protein expression. The E. coli cells recovered by centrifugation were suspended in a binding buffer (20 mM sodium phosphate, 500 mM NaCl, 20 mM imidazole, pH 7.4), disrupted by sonication, and the lysed fragments were applied to a HisTrap FF cride column (GE Heathcare). Thereafter, the desired protein was eluted with an elution buffer (20 mM sodium phosphate, 500 mM NaCl, 500 mM imidazole, pH 7.4), diluted about 10-fold with a TBS buffer, then applied to an affinity gel packed with an M2 agarose (Sigma). Using an AKTA Explorer (GE Healthcare), the desired protein was eluted with an M2 elution buffer (0.1 M glycine-HCl, pH. 3.5), immediately followed by buffer replacement with PBS on a PD10 column (GE Healthcare) to prepare a final specimen.

Figure 14:
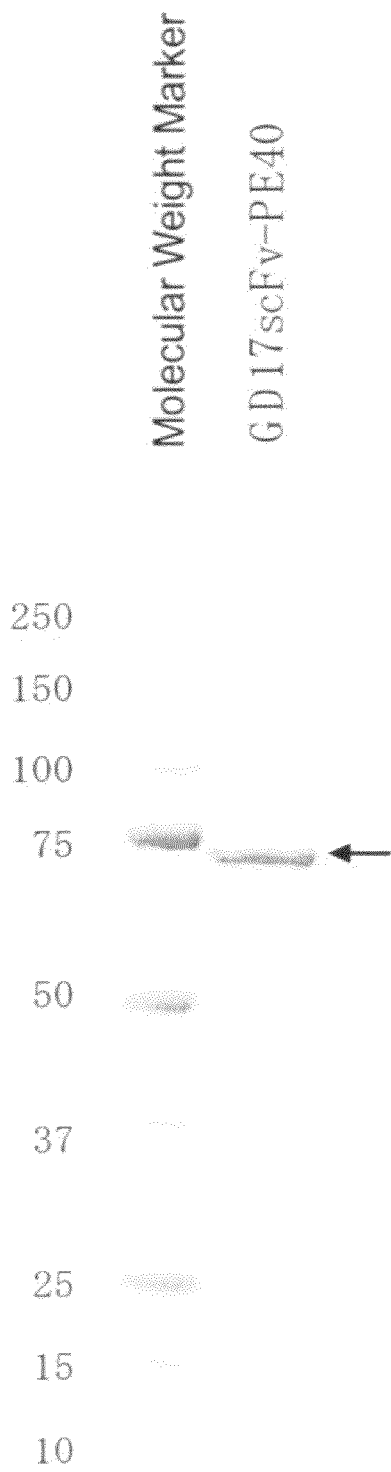
FIG. 14 is a diagram showing the result of SDS-PAGE followed by CBB staining conducted on purified GD17scFv-PE40 to determine its purity.

The purified GD17scFv-PE40 was subjected to SDS-PAGE, then CBB stain was performed to confirm that it had been purified to 100% purity (FIG. 14).

7-3. Analyzing the Activity for Binding to the GRP78 Protein

In the next place, the purified GD17scFv-PE40 protein was analyzed for its GRP78 binding activity. Three specimens were prepared, one stored at 4° C., another left to stand at 37° C. overnight, and the third frozen and thawed; their activities for binding to GRP78 in solid phase were measured by ELISA and compared to each other.

Each specimen was diluted with a diluent buffer (1% BSA, 50 mM Tris, 1 mM $MgCl_2$, 150 mM NaCl, 0.05% Tween 20) and the dilution was added to a plate (NUNC) coated with the GST-GRP78 (1 μg/ml) purified from E. coli. After reaction at room temperature for 1 hour, the plate was washed three times with TBS-T (TBS-0.05% Tween 20) and an anti-flag antibody (M2 antibody, Sigma) was added in an amount of 1 μg/ml, followed by incubation at room temperature for 1 hour. After three additional washings with TBS-T, reaction with an alkali phosphatase-labeled anti-mouse IgG (ZYMED) was conducted for 1 hour and a substrate (Sigma) was added in an amount of 1 mg/ml to develop color.

Figure 15:
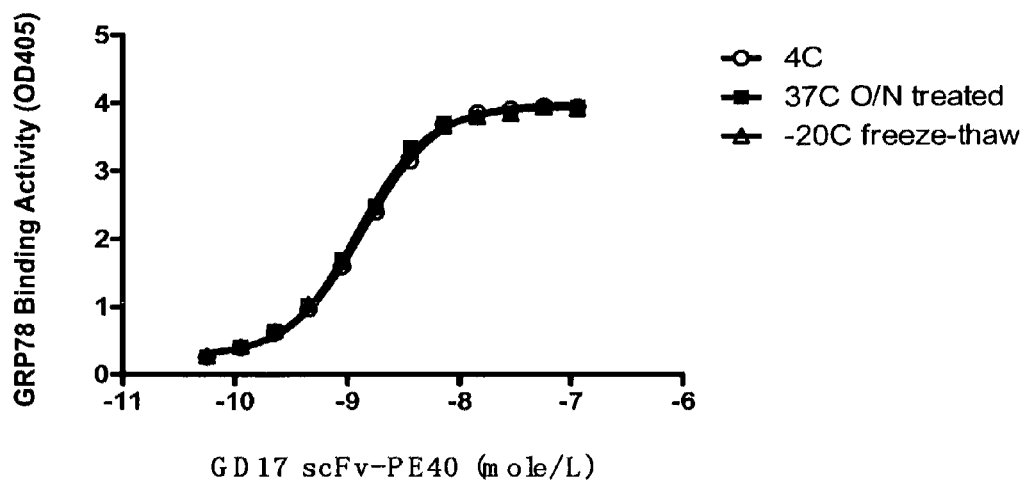
FIG. 15 shows the results of ELISA conducted to analyze both the GRP78 protein binding activities of the purified GD17scFv-PE40 and the stability of the protein; GD17scFv-PE40 stored at 4° C., or let to stand overnight at 37° C., or subjected to a freeze-thaw cycle was diluted to various concentrations and its activity for binding to GST-GRP78 was analyzed by ELISA; the table at the bottom shows the GRP78 protein binding activities of the respective specimens as $EC_{50}$ values.

As it turned out, the GD17scFv-PE40 protein, whether it was stored at 4° C. or left to stand at 37° C. overnight or subjected to a freeze-thaw cycle, had a GRP78 protein binding activity on the order of $EC_{50}$=1.3 nM, demonstrating that the purified specimens are comparatively stable proteins (FIG. 15).

7-4. Analysis of In Vitro Cell Death Inducing Activity

In the next place, the activity of the purified GD17scFv-PE40 for inducing cell death was analyzed on cancer cell lines (22Rv1, LNcap, MCF7, BxPC3, PANC1, and SKOV3) or human derived normal cell lines (HUVEC and MRC5) and mouse derived normal cell lines (CHO, NIH3T3, and BaF3).

Among the cell lines used in the experiment, HUVEC was purchased from CAMBREX and the other cell lines were purchased from ATCC, and they were cultured in accordance with the instruction manuals provided by the suppliers.

The cells of each type were seeded on a 96-well plate and, on the next day, GD17scFv-PE40 was diluted at various concentrations in a 10% FCS containing RPMI1640 medium (Invitrogen) and added to the cells. After 5-day culture, the number of viable cells was counted with WST-8 (nakalai).

Figure 16A:
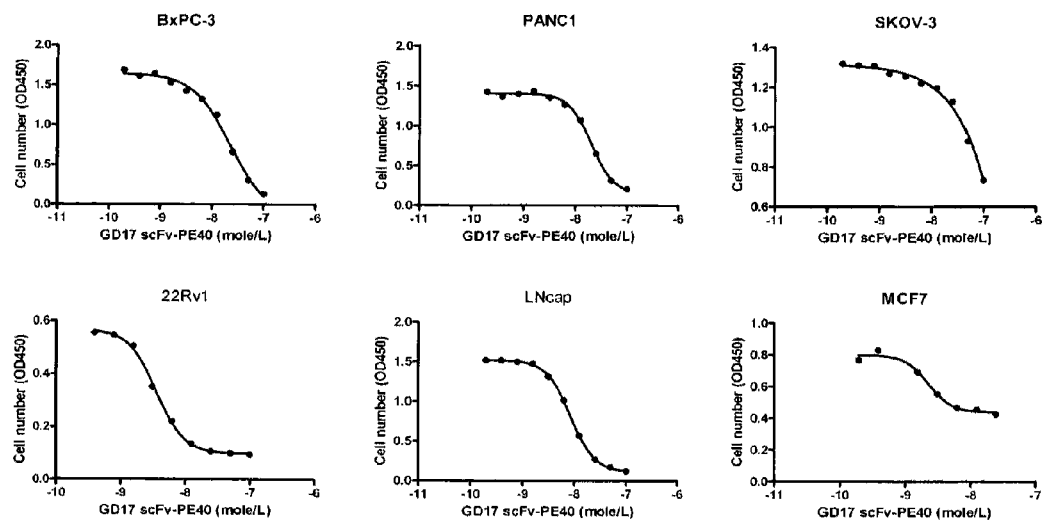
FIG. 16A shows the results of evaluating the cytotoxic activities of the purified GD17scFv-PE40 on various cell lines; GD17scFv-PE40 was diluted to various concentrations and added to cancer cell lines (FIG. 16A) which were cultured for several days, and the number of viable cells was counted; antibody concentrations ($EC_{50}$) that conferred an activity equivalent to 50% of a maximum activity are listed in the table at the bottom.
Figure 16B:
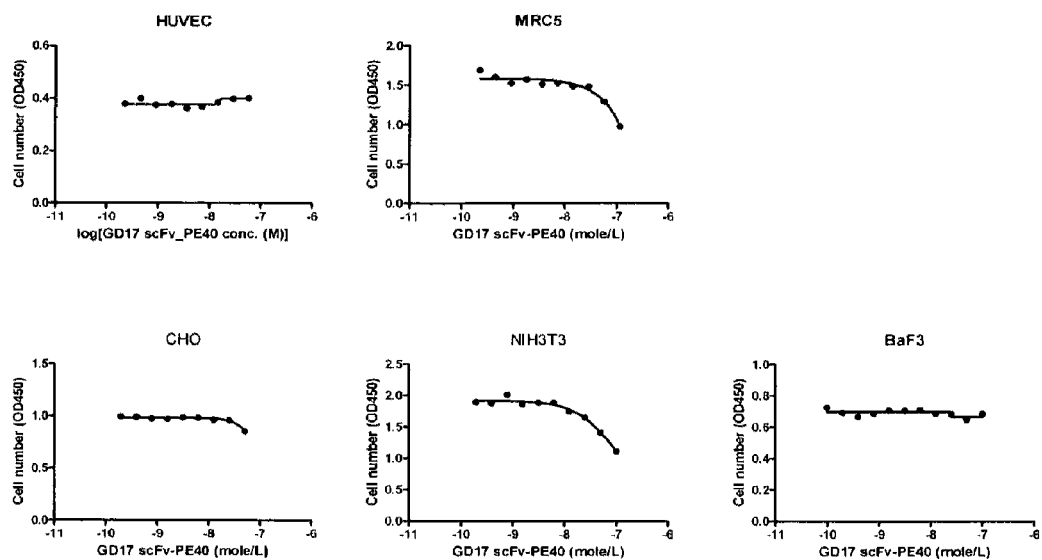
FIG. 16B shows the results of evaluating the cytotoxic activities of the purified GD17scFv-PE40 on various cell lines; GD17scFv-PE40 was diluted to various concentrations and added to normal cell lines (FIG. 16B) which were cultured for several days, and the number of viable cells was counted; antibody concentrations ($EC_{50}$) that conferred an activity equivalent to 50% of a maximum activity ($EC_{50}$) are listed in the table at the bottom.

As it turned out, the sensitivity of GD17scFv-PE40 for the cancer cells varied somewhat but it was confirmed to have strong cell death inducing activities of approximately 2-20 nM in terms of $EC_{50}$ value, or the concentration at which it showed 50% of a maximum activity (FIG. 16A). In particular, the $EC_{50}$ values for MCF7 and 22Rv1 cells were on the order of 2-4 nM, thus confirming the potent cytotoxic activity of GD17scFv-PE40. On the other hand, GD17scFv-PE40 was either totally inactive against the human and mouse normal cells or found to have only low cytotoxic activities when it was added at high concentrations (FIG. 16B).

Figure 17:
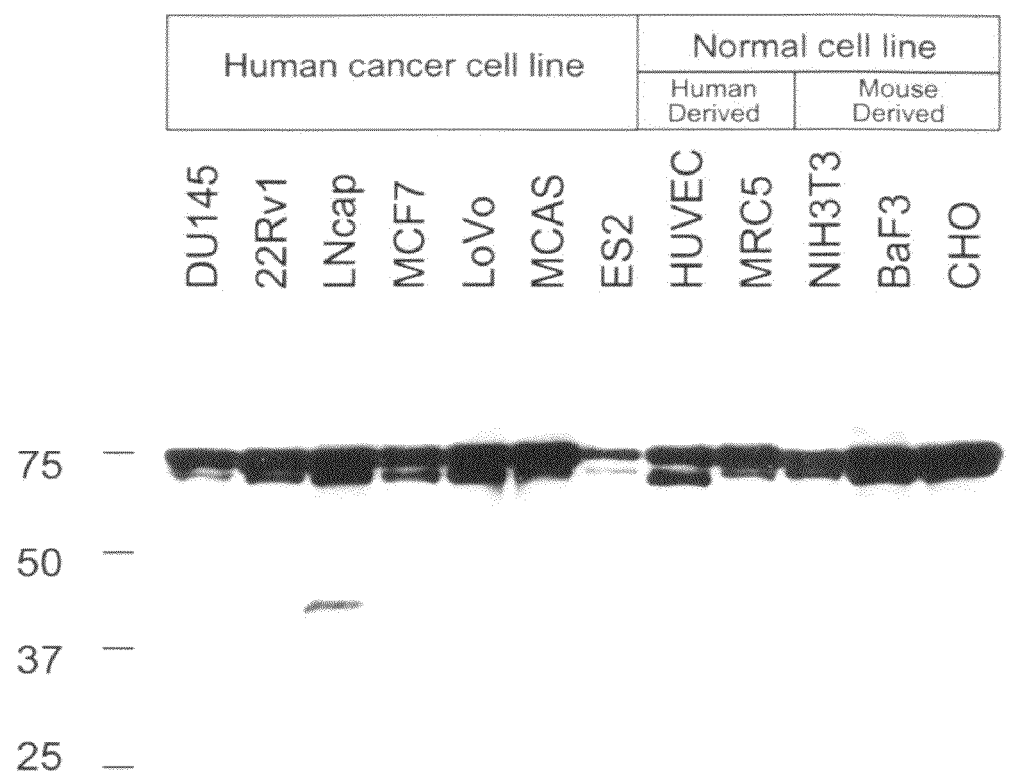
FIG. 17 is a diagram showing the results of analyzing the expression of the GRP78 protein in various cell lines by western blot analysis using the GD-17 antibody.

To confirm that this difference in sensitivity was independent of the fact that the GRP78 protein was expressed in the cancer cells but not in the normal cells, western blotting was performed with the GD-17 antibody. Cell lysates were prepared from the respective types of cells in accordance with the conventional practice and after SDS-PAGE, western blotting was conducted with the GD-17 antibody (2 μg/ml). The result is shown in FIG. 17, from which it is clear that bands specifically stained by the GD-17 were detected in those cell lines on which GD17scFv-PE40 showed no cytotoxic activity; thus, it was assumed that the cancer cell specific cytotoxic activity of GD17scFv-PE40 was not due to the fact that the GRP78 protein was expressed in the cancer cells and not in the normal cells but due to the difference between the two types of cells in terms of localization of the GRP78 protein.

7-5. Analysis of In Vivo Antitumor Activity

The cells of human prostate cancer cell line 22Rv1 (ATCC CRL-2505) were recovered into a 0.05% trypsin supplemented 0.02% EDTA solution and grafted to nude mice [male, 7-wk old (CAnN.Cg-Foxn1<nu>/CrlCrlj (BALB-nu/nu)): charles river, Japan] under the skin of the abdomen in a cell count of $1×10^7$ cells/0.2 mL HBSS (SIGMA Cat. No. H 9269). After confirming tumor implantation, the animals were divided into seven groups (one control group, and six drug administered groups) by tumor volume and body weight on the $16^{th}$ day of grafting (day 16).

On the day after the grouping (day 17), as well as at days 21, 23, 26, and 29, the control group was administered with physiological saline whereas the drug administered groups were administered with GD17scFv-PE40 at a dose of 0.5 mg/kg; both physiological saline and GD17scFv-PE40 were intravenously administered instantaneously in an amount of 10 mL/kg. The tumor volume was measured over time until a final measurement was made two days after the final administration (day 31).

Figure 18:
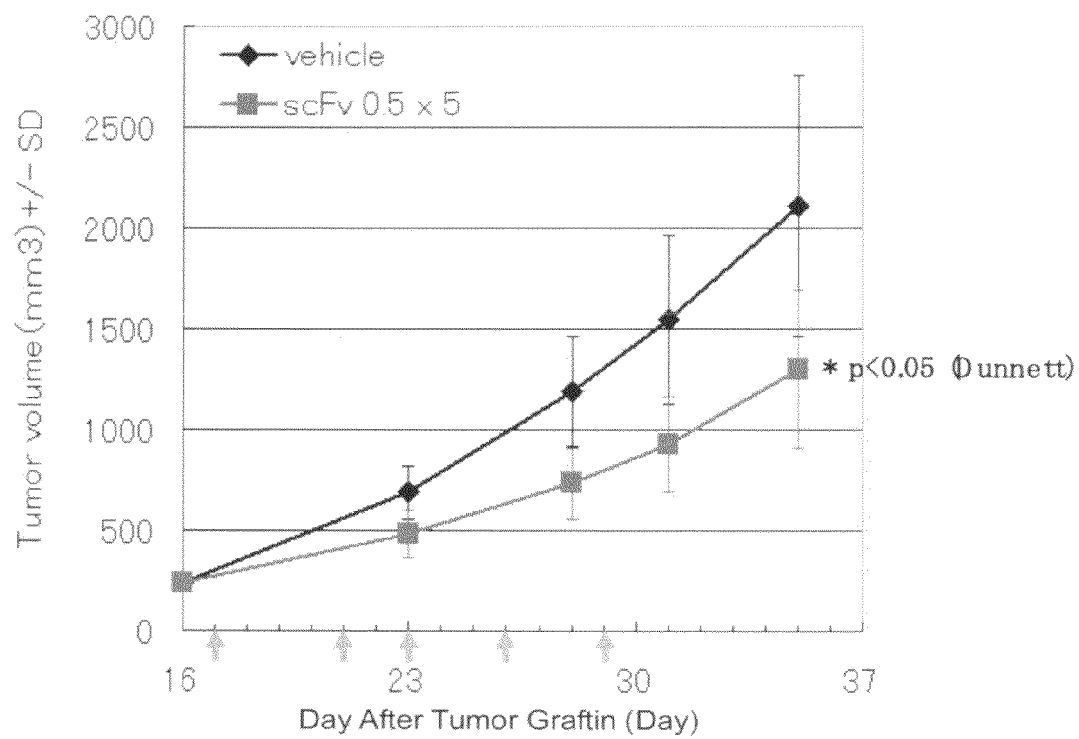
FIG. 18 shows the results of analyzing the antitumor activity of GD17scFv-PE40 in an in vivo mouse xenograft model; immediately after grafting of 22Rv1 (at day 0), or at days 17, 21, 23, 26 and 29, PBS (vehicle) or 0.5 mg/kg of GD17scFv-PE40 was administered (as indicated by the arrows) and, thereafter, the tumor volume was measured over time.

The result is shown in FIG. 18. The percent tumor growth suppression at the final measurement was 47% and an analysis of the tumor volume data by nonparametric Dunnet multiple comparison revealed a significant tumor growth suppressing effect in the groups administered with 0.5 mg/kg of GD17scFv-PE40. This result, showing the in vivo efficacy of GD17scFv-PE40 agains the target GRP78, demonstrated the usefulness of the GRP78 targeting antibodies in cancer treatment.

INDUSTRIAL APPLICABILITY

It has been shown hereinabove that the present invention, by providing novel antibodies that have an activity for binding to GRP78 and which can internalize, can offer novel pharmaceutical compositions that can be used to treat various tumors and cancers that have GRP78 exposed on the cell surface. In addition, by using the antibodies having such characteristics, methods of diagnosing various tumors and cancers can be provided.

The invention claimed is:

1. A pharmaceutical composition containing an antibody that binds to a glucose-regulated protein 78 (GRP78), wherein the antibody binds to the epitope depicted in SEQ ID NO: 3.

2. The composition according to claim 1 which is an anti-cancer agent.

3. The composition according to claim 1, wherein the antibody is a monoclonal antibody.

4. The composition according to claim 1, wherein the antibody is internalized into cells expressing GRP78.

5. The composition according to claim 1, wherein the antibody is conjugated with a cytotoxic substance.

6. A monoclonal antibody that binds to GRP78, wherein the antibody binds to the epitope depicted in SEQ ID NO: 3.

7. The antibody according to claim 6 which is internalized into cells expressing GRP78.

8. The antibody according to claim 6 which recognizes the same epitope as the one that is recognized by an antibody selected from among the following (a) to (f):
(a) an antibody comprising a heavy-chain variable region and a light-chain variable region, the heavy-chain variable region having the amino acid sequence depicted in SEQ ID NO: 8 as CDR1, the amino acid sequence depicted in SEQ ID NO: 9 as CDR2, and the amino acid sequence depicted in SEQ ID NO: 10 as CDR3, and the light-chain variable region having the amino acid sequence depicted in SEQ ID NO: 11 as CDR1, the amino acid sequence depicted in SEQ ID NO: 12 as CDR2, and the amino acid sequence depicted in SEQ ID NO: 13 as CDR3;

(b) an antibody comprising a heavy-chain variable region and a light-chain variable region, the heavy-chain variable region having the amino acid sequence depicted in SEQ ID NO: 18 as CDR1, the amino acid sequence depicted in SEQ ID NO: 19 as CDR2, and the amino acid sequence depicted in SEQ ID NO: 20 as CDR3, and the light-chain variable region having the amino acid sequence depicted in SEQ ID NO: 21 as CDR1, the amino acid sequence depicted in SEQ ID NO: 22 as CDR2, and the amino acid sequence depicted in SEQ ID NO: 23 as CDR3;

(c) an antibody comprising a heavy-chain variable region and a light-chain variable region, the heavy-chain variable region having the amino acid sequence depicted in SEQ ID NO: 61 as CDR1, the amino acid sequence depicted in SEQ ID NO: 62 as CDR2, and the amino acid sequence depicted in SEQ ID NO: 63 as CDR3, and the light-chain variable region having the amino acid sequence depicted in SEQ ID NO: 64 as CDR1, the amino acid sequence depicted in SEQ ID NO: 65 as CDR2, and the amino acid sequence depicted in SEQ ID NO: 66 as CDR3;

(d) an antibody comprising a heavy-chain variable region and a light-chain variable region, the heavy-chain variable region having the amino acid sequence depicted in SEQ ID NO: 71 as CDR1, the amino acid sequence depicted in SEQ ID NO: 72 as CDR2, and the amino acid sequence depicted in SEQ ID NO: 73 as CDR3, and the light-chain variable region having the amino acid sequence depicted in SEQ ID NO: 74 as CDR1, the amino acid sequence depicted in SEQ ID NO: 75 as CDR2, and the amino acid sequence depicted in SEQ ID NO: 76 as CDR3;

(e) an antibody comprising a heavy-chain variable region and a light-chain variable region, the heavy-chain variable region having the amino acid sequence depicted in SEQ ID NO: 81 as CDR1, the amino acid sequence depicted in SEQ ID NO: 82 as CDR2, and the amino acid sequence depicted in SEQ ID NO: 83 as CDR3, and the light-chain variable region having the amino acid sequence depicted in SEQ ID NO: 84 as CDR1, the amino acid sequence depicted in SEQ ID NO: 85 as CDR2, and the amino acid sequence depicted in SEQ ID NO: 86 as CDR3; and (f) an antibody comprising a heavy-chain variable region and a light-chain variable region, the heavy-chain variable region having the amino acid sequence depicted in SEQ ID NO: 91 as CDR1, the amino acid sequence depicted in SEQ ID NO: 92 as CDR2, and the amino acid sequence depicted in SEQ ID NO: 93 as CDR3, and the light-chain variable region having the amino acid sequence depicted in SEQ ID NO: 94 as CDR1, the amino acid sequence depicted in SEQ ID NO: 95 as CDR2, and the amino acid sequence depicted in SEQ ID NO: 96 as CDR3.

9. The antibody according to claim 6 which has cytotoxic activity against cells expressing GRP78.

10. The antibody according to claim 9 which is conjugated with a cytotoxic substance.

11. An anti-GRP78 antibody conjugated with a labeling substance, where the antibody binds to the epitome depicted in SEQ ID NO: 3.

12. A method of delivering a cytotoxic substance into cells using an anti-GRP78 antibody comprising contacting cells with the anti-GRP78 antibody of claim 5.

13. A method of suppressing the growth of cells using a cytotoxic substance bound to an anti-GRP78 antibody comprising contacting cells with the cytotoxic substance bound to the anti-GRP78 antibody of claim 6.

14. The method according to claim 12 or 13, wherein the cells are cancer cells.

15. The method according to claim 14, wherein the cancer cells are selected from the group consisting of prostate cancer cells, breast cancer cells, colon cancer cells, and ovary cancer cells.

16. A process for producing a pharmaceutical composition comprising the following steps:
   (a) the step of providing GRP78 antibodies according to claim 6;
   (b) the step of validating whether the antibodies of (a) have an internalizing activity;
   (c) the step of selecting antibodies having an internalizing activity; and
   (d) the step of binding a cytotoxic substance to the antibodies selected in (c).

17. The process according to claim 16, wherein the pharmaceutical composition is an anticancer agent.

18. A method of diagnosing a cancer expressing GRP78 using the anti-GRP78 antibody of claim 6.

19. The method of diagnosing according to claim 18 which uses an anti-GRP antibody conjugated with a labeling substance.

20. The method of diagnosing according to claim 18 which detects the anti-GRP78 antibody incorporated into cells.

* * * * *